United States Patent
Hubbell et al.

(10) Patent No.: US 9,428,807 B2
(45) Date of Patent: *Aug. 30, 2016

(54) PHASE-PROTECTING REAGENT FLOW ORDERINGS FOR USE IN SEQUENCING-BY-SYNTHESIS

(75) Inventors: Earl Hubbell, Palo Alto, CA (US); Jonathan Schultz, Oxford, MA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 13/440,849

(22) Filed: Apr. 5, 2012

(65) Prior Publication Data

US 2012/0264621 A1    Oct. 18, 2012

Related U.S. Application Data

(60) Provisional application No. 61/473,721, filed on Apr. 8, 2011, provisional application No. 61/544,924, filed on Oct. 7, 2011, provisional application No. 61/549,407, filed on Oct. 20, 2011, provisional application No. 61/617,231, filed on Mar. 29, 2012.

(51) Int. Cl.
*C12Q 1/68* (2006.01)

(52) U.S. Cl.
CPC .......... *C12Q 1/6874* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,750,341 A | 5/1998 | Macevicz | |
| 5,854,033 A | 12/1998 | Lizardi | |
| 6,174,670 B1 | 1/2001 | Wittwer et al. | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,404,907 B1 | 6/2002 | Gilchrist et al. | |
| 6,780,591 B2 | 8/2004 | Williams et al. | |
| 6,828,100 B1 | 12/2004 | Ronaghi | |
| 6,833,246 B2 | 12/2004 | Balasubramanian | |
| 6,911,327 B2 | 6/2005 | McMillan et al. | |
| 7,037,687 B2 | 5/2006 | Williams et al. | |
| 7,049,645 B2 | 5/2006 | Sawada et al. | |
| 7,133,782 B2 | 11/2006 | Odedra | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,782,237 B2 | 8/2010 | Ronaghi et al. | |
| 7,785,862 B2 | 8/2010 | Kim et al. | |
| 7,835,871 B2 | 11/2010 | Kain et al. | |
| 7,875,440 B2 | 1/2011 | Williams et al. | |
| 7,948,015 B2 | 5/2011 | Rothberg et al. | |
| 8,666,678 B2 * | 3/2014 | Davey ............... | C12Q 1/6874 365/94 |
| 2003/0219797 A1 | 11/2003 | Zhao et al. | |
| 2004/0018506 A1 | 1/2004 | Koehler et al. | |
| 2004/0106138 A1 | 6/2004 | Raskind et al. | |
| 2004/0142330 A1 | 7/2004 | Nyren et al. | |
| 2004/0197793 A1 | 10/2004 | Hassibi et al. | |
| 2004/0197845 A1 | 10/2004 | Hassibi et al. | |
| 2005/0084851 A1 | 4/2005 | Ronaghi et al. | |
| 2006/0040297 A1 | 2/2006 | Leamon et al. | |
| 2006/0147935 A1 | 7/2006 | Linnarsson | |

(Continued)

FOREIGN PATENT DOCUMENTS

| | | |
|---|---|---|
| GB | 2461127 | 12/2009 |
| WO | WO-99/57321 | 11/1999 |

(Continued)

OTHER PUBLICATIONS

Rosenfeld, VR. Enumerating De Brujin sequences. Commun.Math. Comput. Chem, vol. 45, p. 71-83, 2002.*
U.S. Appl. No. 13/859,360, Hubbell et al.
U.S. Appl. No. 13/859,667, Schultz et al.
Garcia et al., "Mutation detection by pyrosequencing: sequencing of exons 5-8 of the p53 tumor suppressor gene," *Gene*, 253:249-257 (2000).
Svantesson et al., "A mathematical model of the Pyrosequencing reaction system," *Biophysical Chemistry*, 100:129-145 (2004).
Specification & Drawings of U.S. Appl. No. 61/198,222, filed Nov. 4, 2008.
Appendix to the Specification of U.S. Appl. No. 61/198,222, filed Nov. 4, 2008.
International Preliminary Report on Patentability, International Appl. No. PCT/US2012/032418, dated Oct. 8, 2013.

(Continued)

*Primary Examiner* — Prabha Chunduru
(74) *Attorney, Agent, or Firm* — Jones Robb, PLLC

(57) ABSTRACT

A method for nucleic acid sequencing includes disposing template polynucleotide strands in defined spaces on a sensor array, at least some of the template polynucleotide strands having a sequencing primer and a polymerase operably bound therewith; exposing the template polynucleotide strands to a series of flows of nucleotide species flowed according to a predetermined ordering; and determining, for each of the series of flows of nucleotide species, how many nucleotide incorporations occurred for that particular flow to determine a predicted sequence of nucleotides corresponding to the template polynucleotide strands, wherein the predetermined ordering (a) is not a series of consecutive repetitions of a 4-flow permutation of four different nucleotide species, (b) is not specifically tailored to a particular combination of a particular template polynucleotide strand to be sequenced and a particular sequencing primer to be used, and (c) comprises a phase-protecting flow ordering.

13 Claims, 39 Drawing Sheets

(56) References Cited

U.S. PATENT DOCUMENTS

| | | | |
|---|---|---|---|
| 2006/0147983 A1 | 7/2006 | O'uchi et al. | |
| 2007/0059733 A1 | 3/2007 | Sundararajan et al. | |
| 2007/0059741 A1 | 3/2007 | Kamahori et al. | |
| 2007/0092872 A1 | 4/2007 | Rothberg et al. | |
| 2007/0207471 A1 | 9/2007 | Osaka et al. | |
| 2007/0219367 A1 | 9/2007 | Shchepinov et al. | |
| 2007/0281300 A1 | 12/2007 | Russell et al. | |
| 2008/0161195 A1 | 7/2008 | Turner et al. | |
| 2008/0166727 A1 | 7/2008 | Esfandyarpour et al. | |
| 2008/0182757 A1 | 7/2008 | Heiner et al. | |
| 2008/0268454 A1 | 10/2008 | DeNise et al. | |
| 2008/0286762 A1 | 11/2008 | Miyahara et al. | |
| 2008/0286767 A1 | 11/2008 | Miyahara et al. | |
| 2009/0024331 A1 | 1/2009 | Tomaney et al. | |
| 2009/0026082 A1 | 1/2009 | Rothberg et al. | |
| 2009/0053724 A1 | 2/2009 | Roth et al. | |
| 2009/0105959 A1 | 4/2009 | Braverman et al. | |
| 2009/0127589 A1 | 5/2009 | Rothberg et al. | |
| 2009/0137404 A1 | 5/2009 | Drmanac et al. | |
| 2009/0176200 A1 | 7/2009 | Wakita et al. | |
| 2009/0312188 A1 | 12/2009 | Duer et al. | |
| 2010/0035252 A1 | 2/2010 | Rothberg et al. | |
| 2010/0035253 A1 | 2/2010 | Gordon et al. | |
| 2010/0088255 A1 | 4/2010 | Mann | |
| 2010/0105052 A1 | 4/2010 | Drmanac et al. | |
| 2010/0137143 A1 | 6/2010 | Rothberg et al. | |
| 2010/0160172 A1 | 6/2010 | Erlich et al. | |
| 2010/0173303 A1 | 7/2010 | Ronaghi et al. | |
| 2010/0188073 A1 | 7/2010 | Rothberg et al. | |
| 2010/0192032 A1 | 7/2010 | Chen et al. | |
| 2010/0197507 A1 | 8/2010 | Rothberg et al. | |
| 2010/0199155 A1 | 8/2010 | Kermani et al. | |
| 2010/0209922 A1 | 8/2010 | Williams et al. | |
| 2010/0267043 A1 | 10/2010 | Braverman et al. | |
| 2010/0282617 A1 | 11/2010 | Rothberg et al. | |
| 2010/0300559 A1 | 12/2010 | Schultz et al. | |
| 2010/0300895 A1* | 12/2010 | Nobile et al. | 205/775 |
| 2010/0301398 A1 | 12/2010 | Rothberg et al. | |
| 2010/0304447 A1 | 12/2010 | Harris | |
| 2010/0323348 A1 | 12/2010 | Hamady et al. | |
| 2010/0323350 A1 | 12/2010 | Gordon et al. | |
| 2011/0213563 A1 | 9/2011 | Chen et al. | |
| 2011/0230358 A1 | 9/2011 | Rava | |
| 2011/0246084 A1 | 10/2011 | Ronaghi et al. | |
| 2011/0257889 A1 | 10/2011 | Klammer et al. | |
| 2011/0263463 A1 | 10/2011 | Rothberg et al. | |
| 2011/0275522 A1 | 11/2011 | Rothberg et al. | |
| 2011/0281264 A1 | 11/2011 | Abitbol et al. | |
| 2011/0281737 A1 | 11/2011 | Rothberg et al. | |
| 2011/0281741 A1 | 11/2011 | Rothberg et al. | |
| 2011/0294115 A1 | 12/2011 | Williams et al. | |
| 2012/0035062 A1 | 2/2012 | Schultz et al. | |
| 2012/0037961 A1 | 2/2012 | Rothberg et al. | |
| 2012/0040844 A1 | 2/2012 | Rothberg et al. | |
| 2012/0109598 A1 | 5/2012 | Davey et al. | |
| 2012/0172241 A1 | 7/2012 | Rearick et al. | |
| 2012/0173158 A1 | 7/2012 | Hubbell | |
| 2012/0173159 A1 | 7/2012 | Davey et al. | |
| 2013/0172201 A1* | 7/2013 | Schultz et al. | 506/7 |
| 2013/0280702 A1* | 10/2013 | Schultz et al. | 435/6.1 |
| 2013/0288904 A1 | 10/2013 | Hubbell et al. | |
| 2014/0031238 A1* | 1/2014 | Schultz et al. | 506/2 |

FOREIGN PATENT DOCUMENTS

| | | |
|---|---|---|
| WO | WO-01/01015 | 1/2001 |
| WO | WO-02/20837 | 3/2002 |
| WO | 02/062825 A2 | 8/2002 |
| WO | WO-03/020895 | 3/2003 |
| WO | 2004/001015 | 12/2003 |
| WO | 2004/035741 A2 | 4/2004 |
| WO | WO-2005/040425 | 5/2005 |
| WO | WO-2007/098049 | 8/2007 |
| WO | WO-2008/076406 | 6/2008 |
| WO | WO-2008/092150 | 7/2008 |
| WO | WO-2008/092155 | 7/2008 |
| WO | WO-2009/158006 | 12/2009 |
| WO | WO-2010/047804 | 4/2010 |
| WO | 2010/075188 | 7/2010 |
| WO | WO-2010/077859 | 7/2010 |
| WO | WO 2010075188 A2 * | 7/2010 |
| WO | WO-2010/117804 | 10/2010 |
| WO | WO-2010/138182 | 12/2010 |
| WO | 2011/064319 | 6/2011 |
| WO | WO-2011/120964 | 10/2011 |
| WO | WO-2011/156707 | 12/2011 |
| WO | WO-2012/058459 | 5/2012 |

OTHER PUBLICATIONS

International Search Report and Written Opinion in PCT/US12/32418, mailed on Jul. 25, 2012.

International Search Report and Written Opinion in PCT/US11/39973, mailed on Feb. 3, 2012.

Examiner's first report in Australian Appl. No. 2011226792 based on PCT/US11/39973, dated Nov. 25, 2011.

Non-final Office Action in U.S. Appl. No. 13/157,865, mailed Jul. 30, 2012.

Ahmadian et al., "Pyrosequencing: History, biochemistry and future," *Clin. Chim. Acta*, 363:83-94 (2006).

Aksyonov et al., "Multiplexed DNA sequencing-by-synthesis," *Anal. Biochem.*, 348:127-138.

Anderson et al., "A System for Multiplexed Direct Electrical Detection of DNA Synthesis," *Sens. Actuat. B-Chem.*, 129(1):79-86 (2008).

Balzer et al., "Characteristics of 454 pyrosequencing data—enabling realistic simulation with flowsim," *Bioinformatics*, 26:i420-i425 (2010).

Berger et al., "Compact, universal DNA microarrays to comprehensively determine transcription-factor binding site specificities," *Nat. Biotechnol.*, 24(11):1429-1435 (2006).

Berstel et al., "The origins of combinatorics on words," *Eur. J. Combin.*, 28(3):996-1022.

Brockman et al., "Quality scores and SNP detection in sequencing-by-synthesis systems," *Genome Res.*, 18:763-770 (2008).

Chapter 2, "Machine-Learning Foundations: The Probabilistic Framework," in Baldi, P. & Brunak, S., "Bioinformatics: The Machine Learning Approach," $2^{nd}$ Ed., The MIT Press, 47-65 (2001).

De Bruijn, N.G., "Ackowledgement of priority to C. Flye Sainte-Marie on the counting of circular arrangements of $2^n$ zeros and ones that show each n-letter word exactly once," *T.H.-Report 75-WSK-06*, Technological University Eindhoven (1975).

Droege et al., "The Genome Sequencer FLXTM System—longer reads, more applications, straight forward bioinformatics and more complete data sets," *J. Biotechnol.*, 136:3-10 (2008).

Elahi et al., "Pyrosequencing: A Tool for DNA Sequencing Analysis," in Zhao, S. & Stodolsky, M., Eds., *Methods in Molecular Biology*, vol. 255, Humana Press Inc., pp. 211-219.

Fakhrai-Rad et al., "Pyrosequencing™: An Accurate Detection Platform for Single Nucleotide Polymorphisms," *Hum. Mutat.*, 19:479-485 (2002).

Eltoukhy et al., "Modeling and Base-Calling for DNA Sequencing-By-Synthesis," *2006 IEEE International Conference on Acoustics, Speech, and Signal Processing*, II:1032-1035 (2006).

Finotello et al., "Comparative analysis of algorithms for whole-genome assembly of pyrosequencing data," *Briefings in Bioinformatics Advance Access*, 1-12 (Oct. 21, 2011).

Fuller et al., "The challenges of sequencing by synthesis", *Nat. Biotechnol.*, 27(11):1013-23 (2009).

Guarizadeh, B., "Method Development and Applications of Pyrosequencing Technology," Doctoral Dissertation, Royal Institute of Technology, Stockholm, Sweden (2003).

Hert et al., "Advantages and limitations of next-generation sequencing technologies: a comparison of electrophoresis and non-electrophoresis methods," *Electrophoresis*, 29(23):4618-26 (2008).

Huse et al., "Accuracy and quality of massively parallel DNA pyrosequencing," *Genome Biol.*,8(7):R143.1-R143.9 (2007).

Ji et al., "BM-BC: A Bayesian method of base calling for Solexa sequence data," *Department of Biostatistics, The University of Texas*

(56) References Cited

OTHER PUBLICATIONS

M. D. Anderson Cancer Center, Houston, Texas, U.S.A. (http://odin.mdacc.tmc.edu/~ylji/BMBC/bmbc-ie2.pdf), 1-27, 2010.
Langaee et al., "Genetic variation analyses by Pyrosequencing," *Mutat. Res.*, 573:96-102 (2005).
Leamon et al., "Cramming More Sequencing Reactions onto Microreactor Chips," *Chem. Rev.*, 107:3367-3376 (2007).
Ledergerber et al., "Base-calling for next-generation sequencing platforms," *Briefings in Bioinformatics Advance Access*, 12(5):489-497 (Jan. 18, 2011).
Margulies et al., Supplementary Methods for the article "Genome sequencing in microfabricated high-density picolitre reactors," *Nature*, 437:376-380 (2005), pp. 1-34.
Margulies et al., "Genome sequencing in microfabricated high-density picolitre reactors," *Nature*, 437:376-380 (2005).
Massingham et al., "All Your Base: a fast and accurate probabilistic approach to base calling," *European Bioinformatics Institute, Wellcome Trust Genome Campus*, Hinxton, Cambridgeshire, UK (http://www.ebi.ac.uk/goldman-srv/AYB/references/ayb_revised.pdf), Oct. 26, 2011, 1-26.
Metzker, "Emerging technologies in DNA sequencing," *Genome Res.*, 15:1767-1776 (2005).
Metzker, "Sequencing Technologies—the Next Generation," *Nat. Rev. Genet.*, 11:31-46, 2010.
Pourmand et al., "Direct electrical detection of DNA synthesis," *P. Natl. Adac. Sci. USA*, 103(17):6466-6470 (2006).
Pourmand et al., "Multiplex Pyrosequencing," *Nucleic Acids Res.*, 30(7)(e31):1-5 (2002).
Ronaghi, M, "Pyrosequencing Sheds Light on DNA Sequencing", *Genome Res.*, 11:3-11 (2001).
Ronaghi et al., "A Sequencing Method Based on Real-Time Pyrophosphate," *Science*, 281(5375):363-365 (1998).
Ronaghi et al., "Discovery of single nucleotide polymorphisms and mutations by Pyrosequencing," *Comp. Funct. Genom.*, 3:51-56 (2002).
Van Aardenne-Ehrenfest et al., "Circuits and Trees in Oriented Linear Graphs," *Simon Stevin*, 28:203-217 (1951).
Final Office Action in U.S. Appl. No. 13/859,673, mailed Mar. 21, 2014 (16 pages).
Office Action in U.S. Appl. No. 13/859,673, mailed Sep. 11, 2013 (17 pages).
Office Action in U.S. Appl. No. 13/859,667, mailed Mar. 26, 2014 (18 pages).
Office Action in U.S. Appl. No. 13/859,360, dated Dec. 24, 2013 (10 pages).
Extended European Search Report in EP Appl. No. 11793237.6, mailed Jan. 9, 2014 (7 pages).
Ahmadian et al., "Single-Nucleotide Polymorphism Analysis by Pyrosequencing," *Anal. Biochem.*, 280:103-110 (2000).
U.S. Appl. No. 13/689,252, Non-Final Office Action mailed Jan. 2, 2015, 15 pages.
U.S. Appl. No. 13/859,673, Non-Final Office Action mailed Nov. 4, 2014, 21 pages.
CN 201280027883.4, Chinese Office Action mailed Sep. 22, 2014 and English translation, 12 pages.
U.S. Appl. No. 13/859,667, Non-Final Office Action mailed Mar. 5, 2015, 38 pages.
U.S. Appl. No. 13/859,360, Non-Final Office Action mailed Jan. 16, 2015, 11 pages.
U.S. Appl. No. 13/859,667, Final Office Action mailed Oct. 10, 2014, 25 pages.
Rosenfeld, "Enumerating Kautz Sequences," *Kragujevac J. Math.*, 24:19-41 (2002).
Final Office Action in U.S. Appl. No. 13/689,252 dated Jun. 30, 2015.
Extended European Search Report in Application No. 15178097.0-1403 dated Sep. 17, 2015.
Final Office Action in U.S. Appl. No. 13/859,360 dated Jul. 28, 2015.
Final Office Action in U.S. Appl. No. 13/859,673 dated Jun. 4, 2015.
Advisory Action in U.S. Appl. No. 13/859,673 dated Sep. 24, 2015.

\* cited by examiner

FIG. 12A
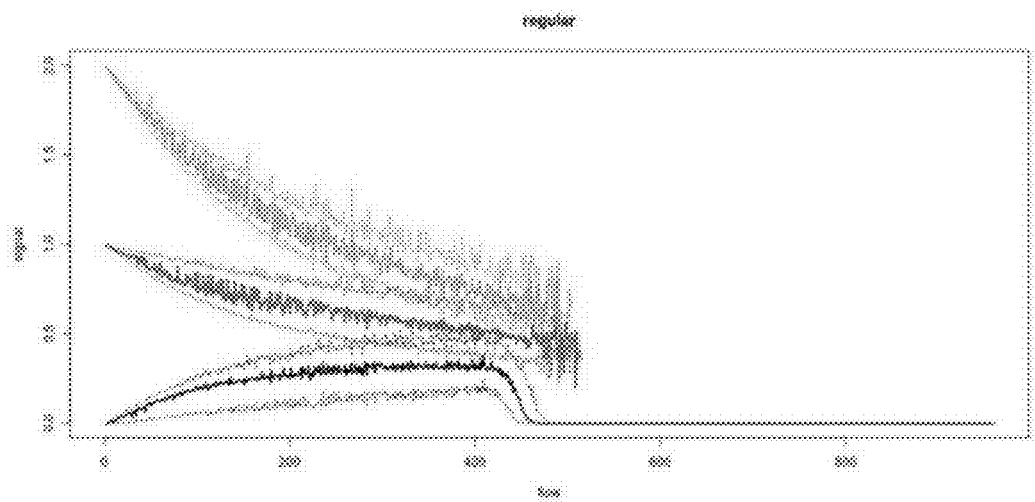
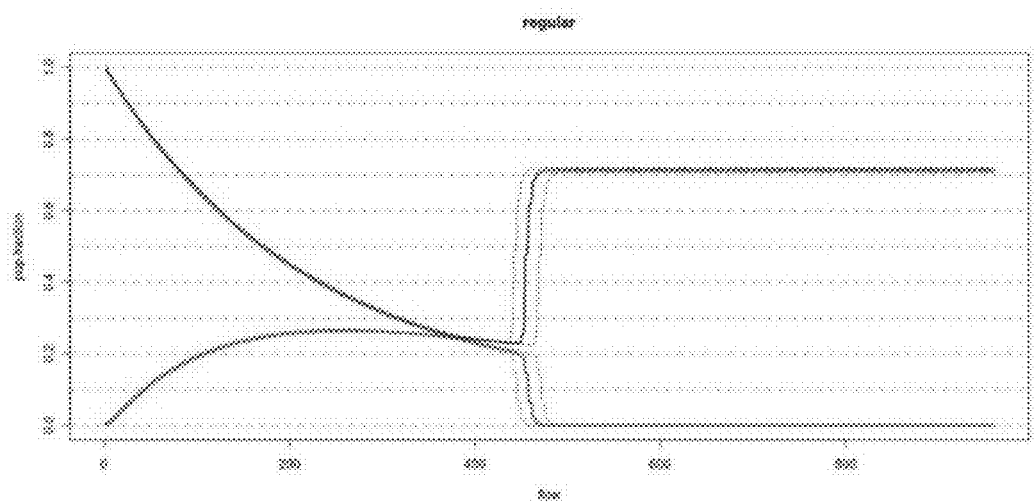
FIG. 12B

FIG. 16A
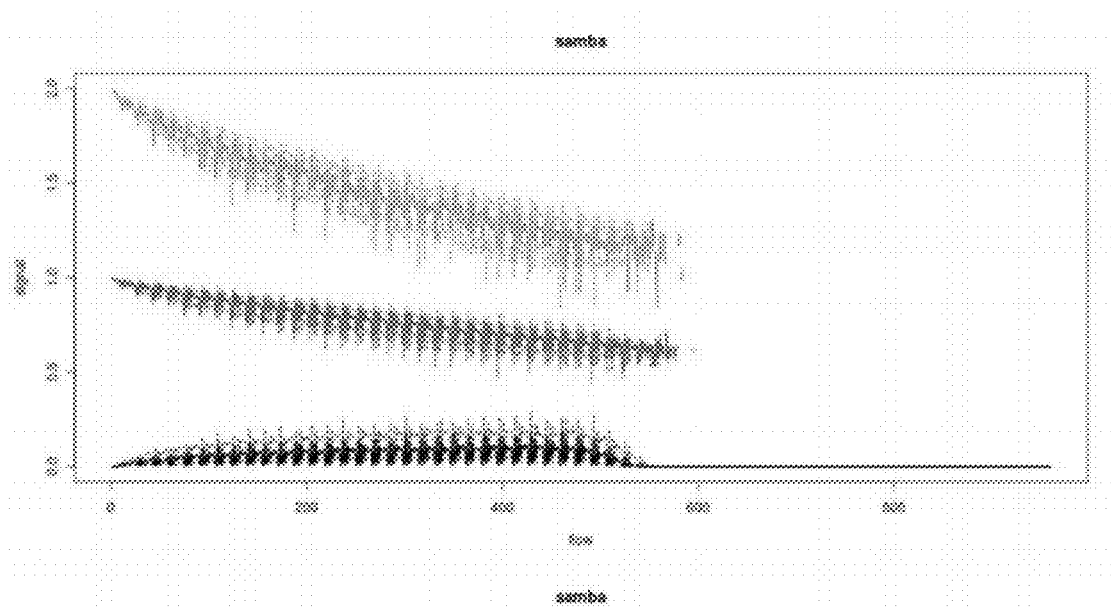
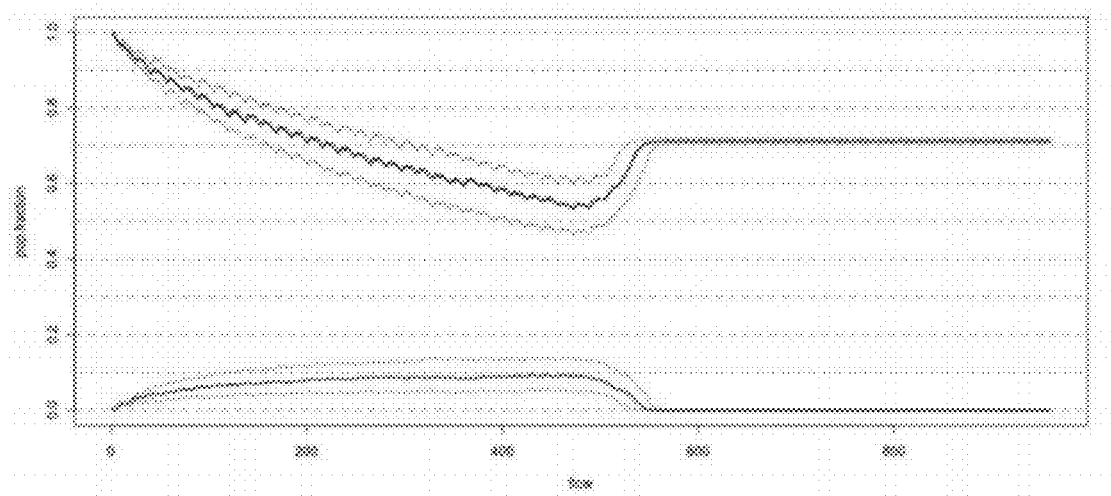
FIG. 16B

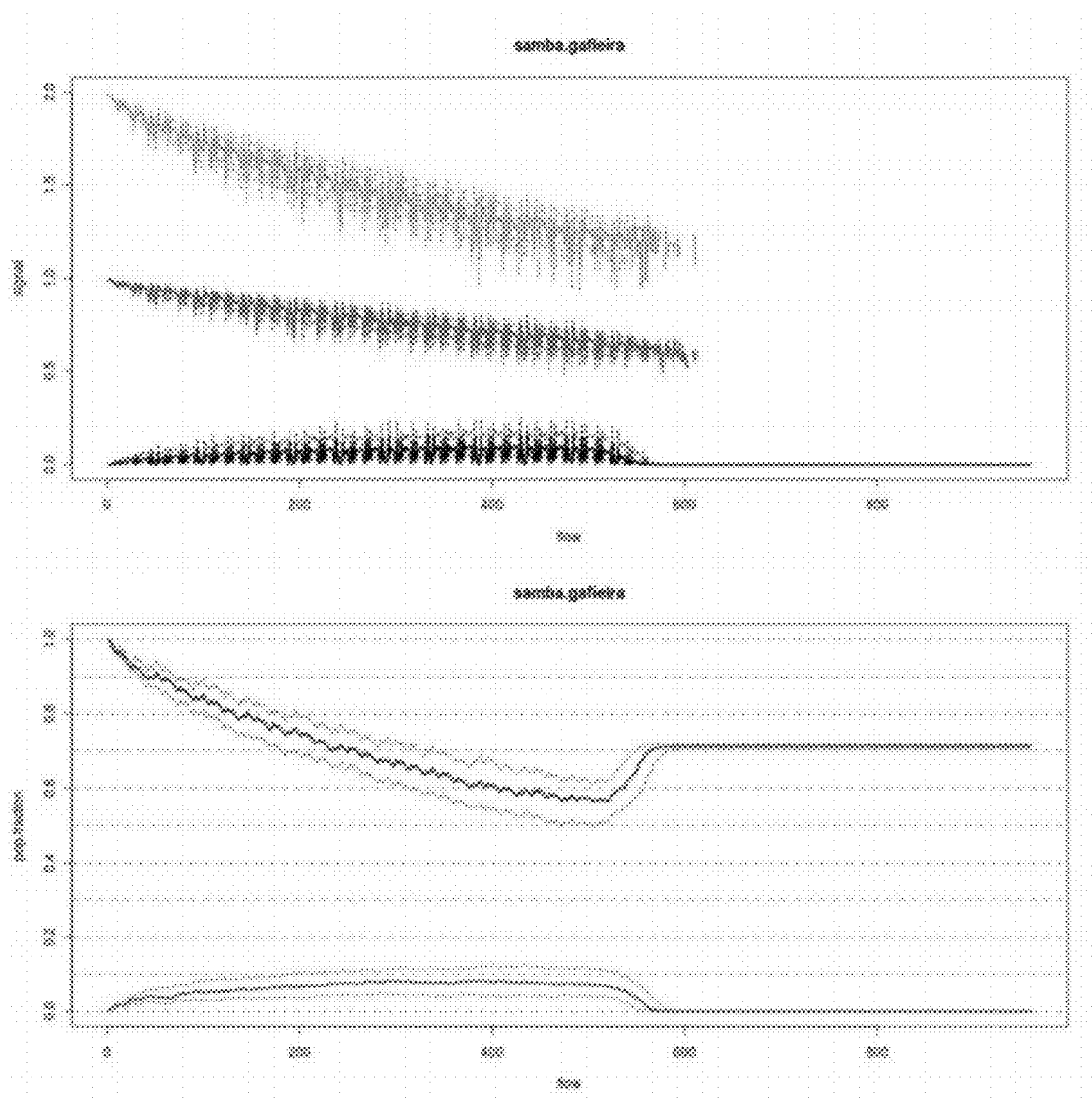

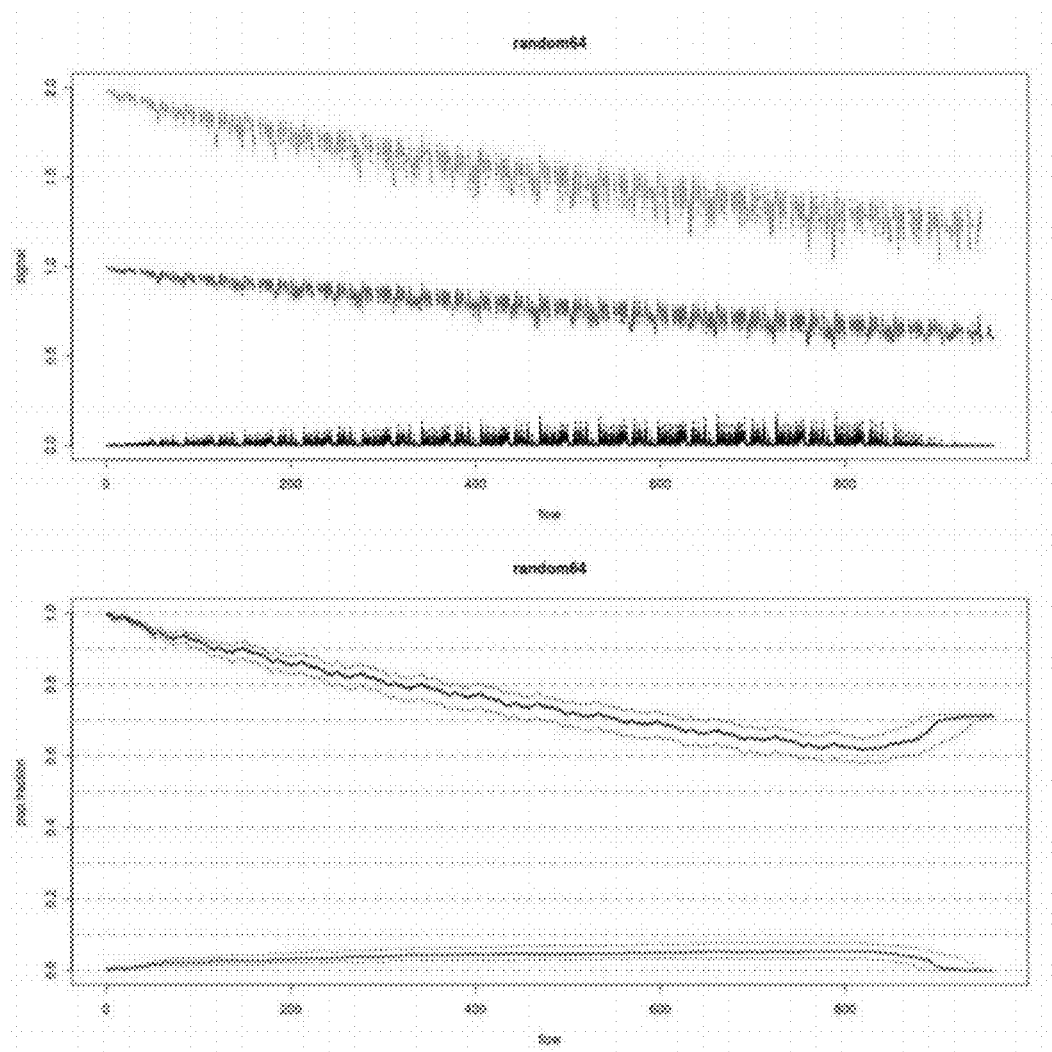

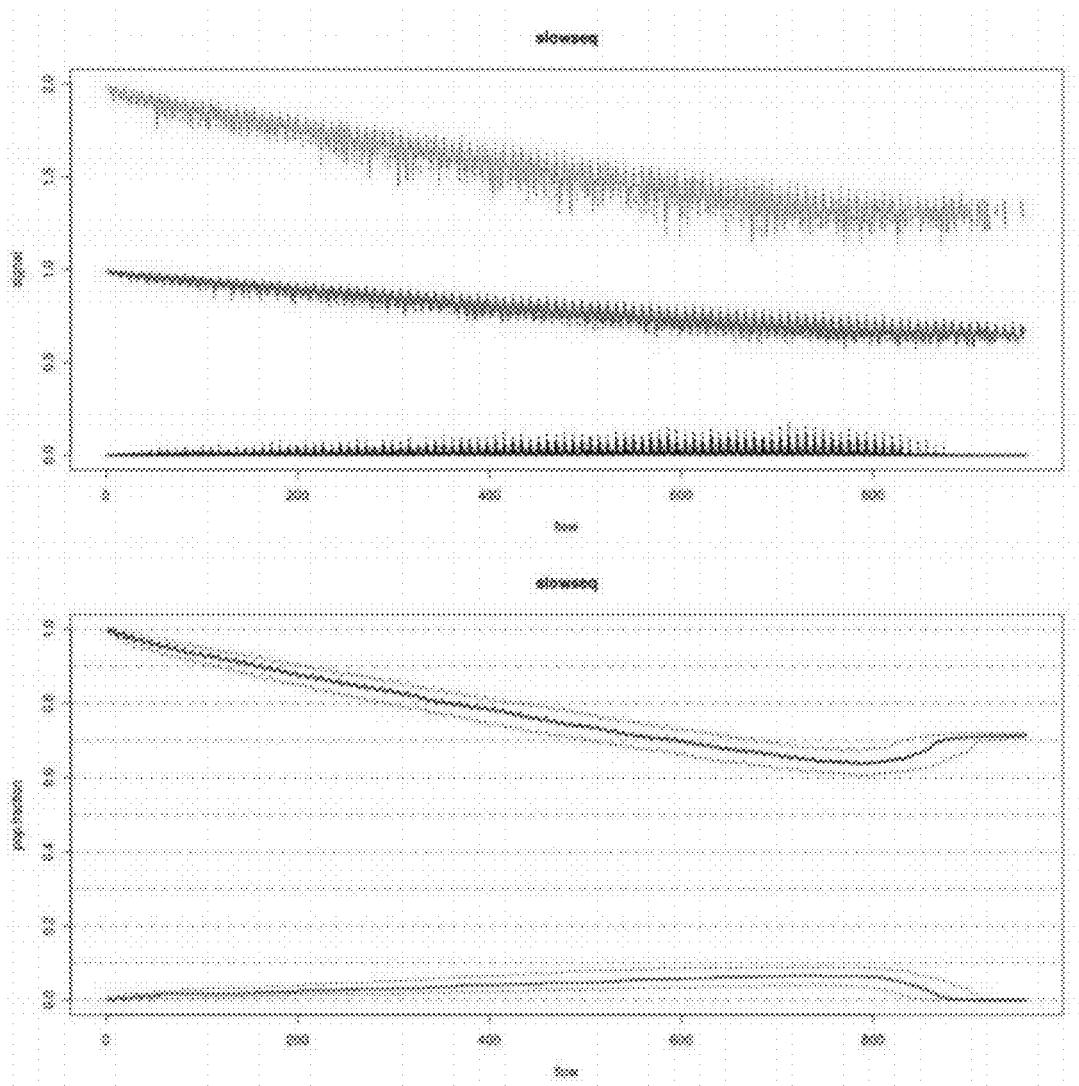

PHASE-PROTECTING REAGENT FLOW ORDERINGS FOR USE IN SEQUENCING-BY-SYNTHESIS

CROSS-REFERENCE TO RELATED APPLICATIONS

This application claims the benefit of U.S. Prov. Pat. Appl. No. 61/473,721 filed Apr. 8, 2011, U.S. Prov. Pat. Appl. No. 61/544,924 filed Oct. 7, 2011, U.S. Prov. Pat. Appl. No. 61/549,407 filed Oct. 20, 2011, and U.S. Prov. Pat. Appl. No. 61/617,231 filed Mar. 29, 2012, which are all incorporated by reference herein in their entirety.

SEQUENCE LISTING

This application contains a Sequence Listing, which has been submitted in ASCII format via EFS-Web and is hereby incorporated by reference in its entirety. Said ASCII copy is named LT00490_ST25_2.txt, was created on Oct. 8, 2014, and is 5,729 bytes in size.

FIELD

This application generally relates to methods, systems, apparatuses, and computer readable media for nucleic acid sequencing, and, more specifically, to methods, systems, apparatuses, and computer readable media involving various phase-protecting reagent flow orderings for use in sequencing-by-synthesis.

BACKGROUND

Various instruments, apparatuses, and/or systems for sequencing nucleic acids sequence nucleic acids using sequencing-by-synthesis. Such instruments, apparatuses, and/or systems may include, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion Personal Genome Machine (PGM™) and Ion Proton™ (Life Technologies Corp./Ion Torrent; see, e.g., U.S. Pat. No. 7,948,015 and U.S. Pat. Appl. Publ. Nos. 2010/0137143, 2009/0026082, and 2010/0282617, which are all incorporated by reference herein in their entirety). In order to increase sequencing efficiency and/or accuracy, there is a need for new methods, systems, apparatuses, and computer readable media that perform sequencing-by-synthesis while reducing or minimizing sequencing errors associated with various phase loss effects that may occur with sequencing-by-synthesis.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 4B discloses SEQ ID NO: 22.

FIGS. 4C-4P disclose SEQ ID NO: 23.

FIG. 5 discloses SEQ ID NO: 1.

FIG. 12A illustrates exemplary simulation data corresponding to signal response curves for an exemplary cyclical, repeating flow ordering of "TACG TACG . . . ."

FIG. 12B illustrates exemplary simulation data corresponding to template population evolution as sequencing progresses for the cyclical, repeating flow ordering of FIG. 12A.

FIG. 16A illustrates exemplary simulation data corresponding to signal response curves for an exemplary flow ordering of "TACG TACG TCTG AGCA TCGA TCGA TGTA CAGC" (SEQ ID NO: 7).

FIG. 16B illustrates exemplary simulation data corresponding to template population evolution as sequencing progresses for the flow ordering of FIG. 16A.

FIG. 17A illustrates exemplary simulation data corresponding to signal response curves for an exemplary flow ordering of "TACG TACG TCTG AGCA TCGA TCGA TGTA CAGC TGAC TGAC TATC GCAG AGCT AGCT ACAT GTCG ACTG ACTG ATAG CGTC ATGC ATGC AGAC TCGT CGTA CGTA CTCA GATG CTAG CTAG CACG TGAT CAGT CAGT CGCT ATGA GTCA GTCA GCGA TACT GCAT GCAT GAGT CTAC GATC GATC GTGC ACTA" (SEQ ID NO: 8).

FIG. 17B illustrates exemplary simulation data corresponding to template population evolution as sequencing progresses for the flow ordering of FIG. 17A.

FIG. 18A illustrates exemplary simulation data corresponding to signal response curves for an exemplary random flow ordering of "CTTG CTTA CAAC TCTC ATAT CGGT ATCC TGTG GAAA CTCC GTTA TCAG CATC CTCT CATG TTAG" (SEQ ID NO: 9).

FIG. 18B illustrates exemplary simulation data corresponding to template population evolution as sequencing progresses for the random flow ordering of FIG. 18A.

FIG. 19A illustrates exemplary simulation data corresponding to signal response curves for an exemplary flow ordering of "TACA CTCT AGTA TAGA GTCG TGTC TCGA CGCG AGAC" (SEQ ID NO: 10).

FIG. 19B illustrates exemplary simulation data corresponding to template population evolution as sequencing progresses for the flow ordering of FIG. 19A.

EXEMPLARY EMBODIMENTS

Figure 1:
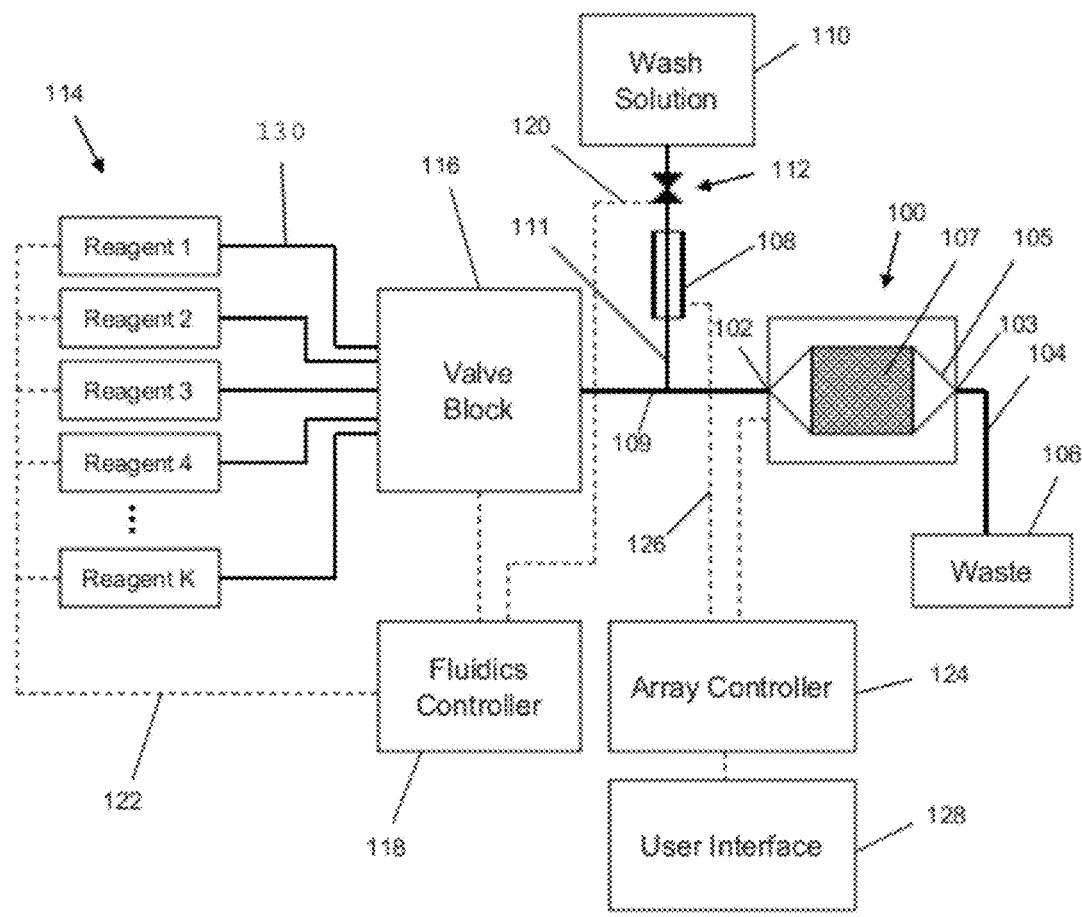
FIG. 1 illustrates components of an exemplary system for nucleic acid sequencing.

The following description and the various embodiments described herein are exemplary and explanatory only and are not to be construed as limiting or restrictive in any way.

Other embodiments, features, objects, and advantages of the present teachings will be apparent from the description and accompanying drawings, and from the claims.

In accordance with the teachings and principles embodied in this application, new methods, systems, apparatuses, and computer readable media that perform sequencing-by-synthesis while reducing or minimizing sequencing errors associated with various phase loss effects that may occur with sequencing-by-synthesis are provided.

Unless otherwise specifically designated herein, terms, techniques, and symbols of biochemistry, cell biology, genetics, molecular biology, nucleic acid chemistry, and organic chemistry (including, e.g., chemical and physical analysis of polymer particles, nucleic acid sequencing and analysis, polymerization techniques, preparation of synthetic polynucleotides, recombinant techniques, etc.) used herein follow those of standard treatises and texts in the relevant field. See, e.g., Kornberg and Baker, DNA REPLICATION, 2nd ed. (W.H. Freeman, New York, 1992); Lehninger, BIOCHEMISTRY, 2nd ed. (Worth Publishers, New York, 1975); Strachan and Read, HUMAN MOLECULAR GENETICS, 2nd ed. (Wiley-Liss, New York, 1999); Birren et al. (eds.), GENOME ANALYSIS: A LABORATORY MANUAL SERIES (Vols. I-IV), Dieffenbach and Dveksler (eds.), PCR PRIMER: A LABORATORY MANUAL, and Green and Sambrook (eds.), MOLECULAR CLONING: A LABORATORY MANUAL (all from Cold Spring Harbor Laboratory Press); and Hermanson, BIOCONJUGATE TECHNIQUES, 2nd ed. (Academic Press, 2008).

In this application, "amplifying" generally refers to performing an amplification reaction.

In this application, "amplicon" generally refers to a product of a polynucleotide amplification reaction, which includes a clonal population of polynucleotides, which may be single stranded or double stranded and which may be replicated from one or more starting sequences. The one or more starting sequences may be one or more copies of the same sequence, or they may be a mixture of different sequences that contain a common region that is amplified such as, for example, a specific exon sequence present in a mixture of DNA fragments extracted from a sample. Preferably, amplicons may be formed by the amplification of a single starting sequence. Amplicons may be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, including such reactions disclosed in one or more of Gelfand et al., U.S. Pat. No. 5,210,015; Kacian et al., U.S. Pat. No. 5,399,491; Mullis, U.S. Pat. No. 4,683,202; Mullis et al., U.S. Pat. Nos. 4,683,195; 4,965,188; and 4,800,159; Lizardi, U.S. Pat. No. 5,854,033; and Wittwer et al., U.S. Pat. No. 6,174,670, which are all incorporated by reference herein in their entirety. In an embodiment, amplicons may be produced by PCRs. Amplicons may also be generated using rolling circle amplification to form a single body that may exclusively occupy a microwell as disclosed in Drmanac et al., U.S. Pat. Appl. Publ. No. 2009/0137404, which is incorporated by reference herein in its entirety.

In this application, "solid phase amplicon" generally refers to a solid phase support, such as a particle or bead, to which is attached a clonal population of nucleic acid sequences, which may have been produced by a process such as emulsion PCR, for example.

In this application, "analyte" generally refers to a molecule or biological cell that can directly affect an electronic sensor in a region (such as a defined space or reaction confinement region or microwell, for example) or that can indirectly affect such an electronic sensor by a by-product from a reaction involving such molecule or biological cell located in such region. In an embodiment, an analyte may be a sample or template nucleic acid, which may be subjected to a sequencing reaction, which may, in turn, generate a reaction by-product, such as one or more hydrogen ions, that can affect an electronic sensor. The term "analyte" also comprehends multiple copies of analytes, such as proteins, peptides, nucleic acids, for example, attached to solid supports, such as beads or particles, for example. In an embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNA or amplicon library (which are examples of library fragments further discussed herein), or a sample emulsion PCR process creating clonally-amplified sample nucleic acid templates on particles such as IonSphere™ particles. An analyte may include particles having attached thereto clonal populations of DNA fragments, e.g., genomic DNA fragments, cDNA fragments, for example.

In this application, "primer" generally refers to an oligonucleotide, either natural or synthetic, that is capable, upon forming a duplex with a polynucleotide template, of acting as a point of initiation of nucleic acid synthesis and being extended from its 3' end along the template so that an extended duplex may be formed. Extension of a primer may be carried out with a nucleic acid polymerase, such as a DNA or RNA polymerase. The sequence of nucleotides added in the extension process may be determined by the sequence of the template polynucleotide. Primers may have a length in the range of from 14 to 40 nucleotides, or in the range of from 18 to 36 nucleotides, for example, or from N to M nucleotides where N is an integer larger than 18 and M is an integer larger than N and smaller than 36, for example. Other lengths are of course possible. Primers may be employed in a variety of amplification reactions, including linear amplification reactions using a single primer, or polymerase chain reactions, employing two or more primers, for example. Guidance for selecting the lengths and sequences of primers for particular applications may be found in Dieffenbach and Dveksler (eds.), PCR PRIMER: A LABORATORY MANUAL, 2nd ed. (Cold Spring Harbor Laboratory Press, New York, 2003).

In this application, "polynucleotide" or "oligonucleotide" generally refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, for example. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, for example. In an embodiment, oligonucleotide may refer to smaller polynucleotides, for example, having 5-40 monomeric units. Polynucleotides may include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs, e.g., including modified bases, sugars, or internucleosidic linkages. In an embodiment, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or obvious from context. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Unless otherwise noted the terminology and atom numbering conventions will follow those disclosed in Strachan and Read, HUMAN MOLECULAR GENETICS, 2nd ed. (Wiley-Liss, New York, 1999). Polynucleotides may range in size from a few monomeric units, e.g., 5-40, to several thousand monomeric units, for example.

In this application, "defined space" (or "reaction space," which may be used interchangeably with "defined space") generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an embodiment, a defined space may be a reaction chamber, such as a well or a microwell, which may be in a chip. In an embodiment, a defined space may be a substantially flat area on a substrate without wells, for example. A defined space may contain or be exposed to enzymes and reagents used in nucleotide incorporation.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, may be fabricated using any suitable microfabrication techniques, and may have volume, shape, aspect ratio (e.g., base width-to-well depth ratio), and other dimensional characteristics that may be selected depending on particular applications, including the nature of reactions taking place as well as the reagents, by-products, and labeling techniques (if any) that are employed. Reaction confinement regions may also be substantially flat areas on a substrate without wells, for example. In various embodiments, microwells may be fabricated as described in one or more of Doering and Nishi (eds.), HANDBOOK OF SEMICONDUCTOR MANUFACTURING TECHNOLOGY, 2nd ed. (CRC Press, 2007); Saliterman, FUNDAMENTALS OF BIOMEMS AND MEDICAL MICRODEVICES (SPIE Press Book, 2006); Elwenspoek et al., SILICON MICROMACHINING (Cambridge University Press, 2004); and the like. Various exemplary configurations (e.g., spacing, shape, and volume) of microwells or reaction chambers are disclosed in Rothberg et al., U.S. Pat. Publ. Nos. 2009/0127589 and 2009/0026082; Rothberg et al., U.K. Pat. Appl. Publ. No. GB 2461127; and Kim et al., U.S. Pat. No. 7,785,862, which are all incorporated by reference in their entirety.

Defined spaces or reaction confinement regions may be arranged as an array, which may be a substantially planar one-dimensional or two-dimensional arrangement of elements such as sensors or wells. The number of columns (or rows) of a two-dimensional array may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Preferably, each reaction chamber is no greater than 10 μm$^3$ (i.e., 1 pL) in volume, or no greater than 0.34 pL in volume, and more preferably no greater than 0.096 pL or even 0.012 pL in volume. A reaction chamber may be $2^2, 3^2, 4^2, 5^2, 6^2, 7^2, 8^2, 9^2$, or $10^2$ square microns in cross-sectional area at the top, for example. Preferably, the array may have at least $10^2, 10^3, 10^4, 10^5, 10^6, 10^7, 10^8, 10^9$, or more reaction chambers, for example. The reaction chambers may be capacitively coupled to chemFETs. Microwells may have any polygonal cross sections, including square, rectangular, or octagonal cross sections, for example, and may be arranged as a rectilinear array on a surface. Microwells may have hexagonal cross sections and be arranged as a hexagonal array, which permits a higher density of microwells per unit area than rectilinear arrays. An array of defined spaces or reaction confinement regions may be an array of discrete areas on a substantially flat substrate without wells.

Defined spaces or reaction confinement regions, whether arranged as an array or in some other configuration, may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement region, for example, may be represented as an electrical signal or a voltage, which may be digitalized (e.g., converted to a digital representation of the electrical signal or the voltage). Any of these measurements and representations may be considered raw data or a raw signal. The structure and/or design of sensors for use with the present teachings may vary widely and may include one or more features of the following references, which are all incorporated by reference herein in their entirety: Barbaro et al., U.S. Pat. No. 7,535,232; Esfandyarpour et al., U.S. Pat. Appl. Publ. No. 2008/0166727; Kamahori et al., U.S. Pat. Appl. Publ. No. 2007/0059741; Miyahara et al., U.S. Pat. Appl. Publ. Nos. 2008/0286767 and 2008/0286762; O'uchi, U.S. Pat. Appl. Publ. No. 2006/0147983; Osaka et al., U.S. Pat. Appl. Publ. No. 2007/0207471; Rothberg et al., U.S. Pat. Appl. Publ. No. 2009/0127589; Rothberg et al., U.K. Pat. Appl. Publ. No. GB 2461127; and Sawada et al., U.S. Pat. No. 7,049,645.

In this application, "reaction mixture" generally refers to a solution containing any necessary reactants for performing a reaction, which may include, for example, buffering agents to maintain pH at a selected level during a reaction, salts, enzymes, co-factors, scavengers, etc., for example.

In this application, "microfluidics device" generally refers to an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, etc. Microfluidics devices may further include valves, pumps, and specialized functional coatings on interior walls, e.g., to prevent adsorption of sample components or reactants, facilitate reagent movement by electroosmosis, etc. Such devices may be fabricated using micromachining techniques or precision molding, for example, in or as a solid substrate, which may be glass, plastic, or other solid polymeric materials, and may have a planar format for ease of detecting and monitoring sample and reagent movement, especially via optical or electrochemical methods. Features of a microfluidic device may have cross-sectional dimensions of less than a few hundred square micrometers, for example, and passages may have capillary dimensions, e.g., having maximal cross-sectional dimensions of from about 500 μm to about 0.1 μm, for example. Microfluidics devices may have volume capacities in the range of from 1 μL to a few nL, e.g., 10-100 nL, for example.

In various embodiments, the methods, systems, apparatuses, and computer readable media described herein may advantageously be used to determine the sequence and/or identity of one or more nucleic acid samples using sequencing-by-synthesis. In sequencing-by-synthesis, the sequence of a target nucleic acid may be determined by the stepwise synthesis of complementary nucleic acid strands on a target nucleic acid (whose sequence and/or identity is to be determined) serving as a template for the synthesis reactions (e.g., by a polymerase extension reaction that typically includes the formation of a complex comprising a template (or target polynucleotide), a primer annealed thereto, and a polymerase operably coupled or associated with the primer-template hybrid so as to be capable of incorporating a nucleotide species (e.g., a nucleoside triphosphate, a nucleotide triphosphate, a precursor nucleoside or nucleotide) to the primer). During sequencing-by-synthesis, nucleotides may be sequentially added to growing polynucleotide molecules or strands at positions complementary to template polynucleotide molecules or strands. The addition of the nucleotides to the growing complementary strands, which may be detected using a variety of methods (e.g., pyrosequencing, fluorescence detection, and label-free electronic detection), may be used to identify the sequence composition of the template nucleic acid. This process may be iterated until a complete or selected sequence length complementary to the template has been synthesized.

In various embodiments, the methods, systems, apparatuses, and computer readable media described herein may advantageously be used to generate, process, and/or analyze data and signals obtained using electronic or charged-based nucleic acid sequencing. In electronic or charged-based sequencing (such as, e.g., pH-based sequencing), a nucleotide incorporation event may be determined by detecting ions (e.g., hydrogen ions) generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured signals indicative of ion concentration during each nucleotide flow, the identity of the type, sequence and number of nucleotide(s) associated with a sample nucleic acid present in a reaction chamber can be determined.

FIG. 1 illustrates components of an exemplary system for nucleic acid sequencing. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The reagents 114 may, for example, contain dNTPs to be flowed through passages 130 and through the valve block 116, which may control the flow of the reagents 114 to flow chamber 105 (also referred to herein as a reaction chamber) via passage 109. The system may include a reservoir 110 for containing a wash solution that may be used to wash away dNTPs, for example, that may have previously been flowed. The microwell array 107 may include an array of defined spaces or reaction confinement regions, such as microwells, for example, that is operationally associated with a sensor array so that, for example, each microwell has a sensor suitable for detecting an analyte or reaction property of interest. The microwell array 107 may preferably be integrated with the sensor array as a single device or chip. The flow cell may have a variety of designs for controlling the path and flow rate of reagents over the microwell array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls. The system may be configured to let a single fluid or reagent contact the reference electrode 108 throughout an entire multi-step reaction. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an embodiment, the wash solution 110 may be selected as being in continuous contact with the reference electrode 108, which may be especially useful for multi-step reactions using frequent wash steps.

In various embodiments, the fluidics controller 118 may be programmed to control driving forces for flowing reagents 114 and the operation of valve 112 and valve block 116 with any suitable instrument control software, such as LabView (National Instruments, Austin, Tex.), to deliver reagents to the flow cell and sensor array 100 according to a predetermined reagent flow ordering. The reagents may be delivered for predetermined durations, at predetermined flow rates, and may measure physical and/or chemical parameters providing information about the status of one or more reactions taking place in defined spaces or reaction confinement regions, such as, for example, microwells. The predetermined ordering may be based on a cyclical, repeating pattern consisting of consecutive repeats of a short pre-determined reagent flow ordering (e.g., consecutive repeats of pre-determined sequence of four nucleotide reagents such as, for example, "ACTG ACTG ACTG . . . "), may be based in whole or in part on some other pattern of reagent flows (such as, e.g., any of the various phase-protecting reagent flow orderings discussed herein), and may also be based on some combination thereof.

Figure 2A:
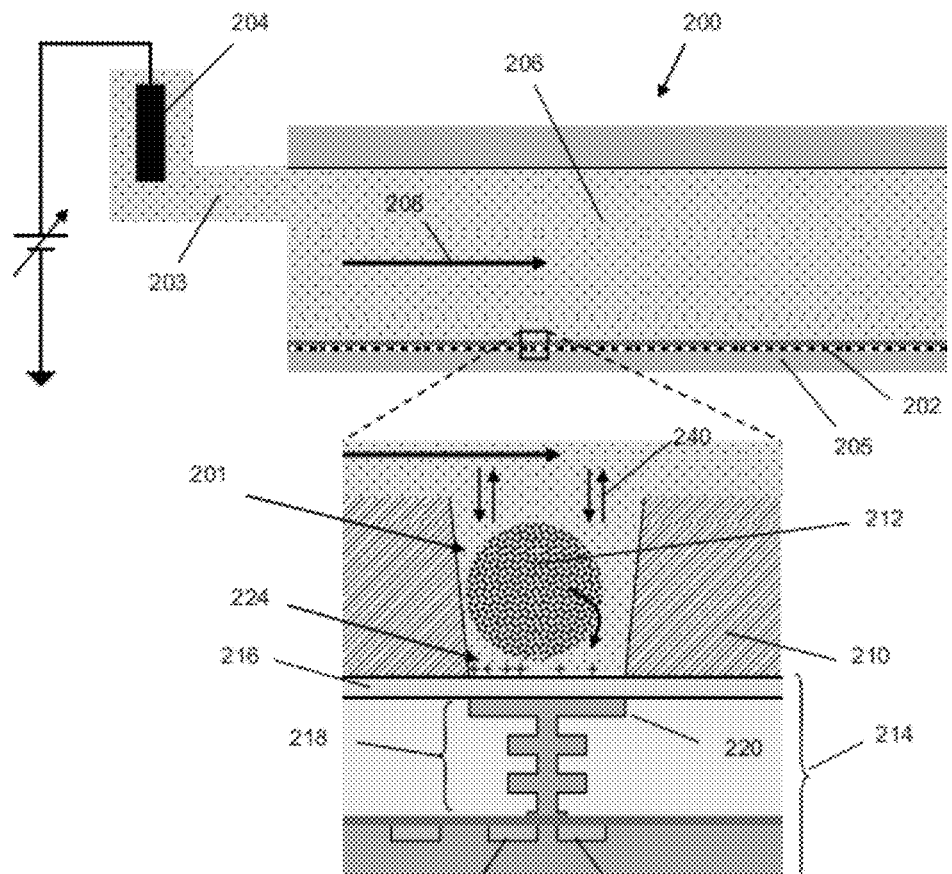
FIG. 2A illustrates cross-sectional and expanded views of an exemplary flow cell for nucleic acid sequencing.

FIG. 2A illustrates cross-sectional and expanded views of an exemplary flow cell 200 for nucleic acid sequencing. The flow cell 200 includes a microwell array 202, a sensor array 205, and a flow chamber 206 in which a reagent flow 208 may move across a surface of the microwell array 202, over open ends of microwells in the microwell array 202. The flow of reagents (e.g., nucleotide species) can be provided in any suitable manner, including delivery by pipettes, or through tubes or passages connected to a flow chamber. The duration, concentration, and/or other flow parameters may be the same or different for each reagent flow. Likewise, the duration, composition, and/or concentration for each wash flow may be the same or different. A microwell 201 in the microwell array 202 may have any suitable volume, shape, and aspect ratio, which may be selected depending on one or more of any reagents, by-products, and labeling techniques used, and the microwell 201 may be formed in layer 210, for example, using any suitable microfabrication technique. A sensor 214 in the sensor array 205 may be an ion sensitive (ISFET) or a chemical sensitive (chemFET) sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220. In an embodiment, a reference electrode 204 may be fluidly connected to the flow chamber 206 via a flow passage 203. In an embodiment, the microwell array 202 and the sensor array 205 may together form an integrated unit forming a bottom wall or floor of the flow cell 200. In an embodiment, one or more copies of an analyte may be attached to a solid phase support 212, which may include microparticles, nanoparticles, beads, gels, and may be solid and porous, for example. The analyte may include a nucleic acid analyte, including a single copy and multiple copies, and may be made, for example, by rolling circle amplification (RCA), exponential RCA, or other suitable techniques to produce an amplicon without the need of a solid support.

Figure 2B:
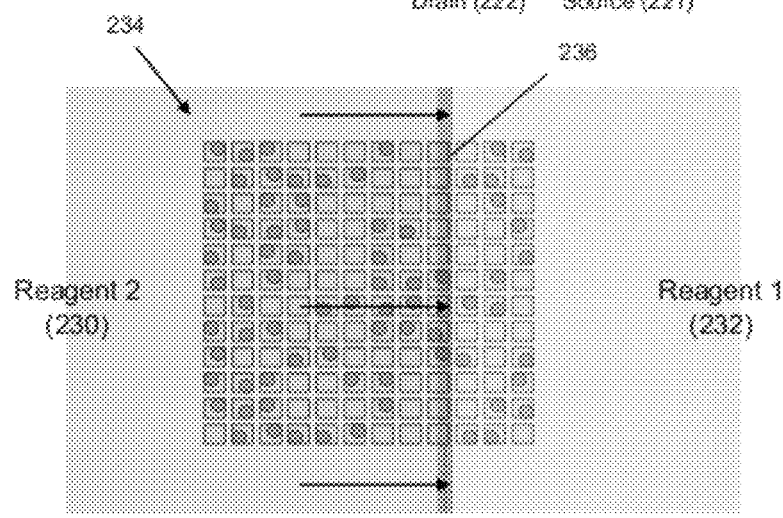
FIG. 2B illustrates an exemplary uniform flow front between successive reagents moving across a section of an exemplary microwell array.

FIG. 2B illustrates an exemplary uniform flow front between successive reagents moving across a section 234 of an exemplary microwell array. A "uniform flow front" between first reagent 232 and second reagent 230 generally refers to the reagents undergoing little or no mixing as they move, thereby keeping a boundary 236 between them narrow. The boundary may be linear for flow cells having inlets and outlets at opposite ends of their flow chambers, or it may be curvilinear for flow cells having central inlets (or outlets) and peripheral outlets (or inlets). In an embodiment, the flow cell design and reagent flow rate may be selected so that each new reagent flow with a uniform flow front as it transits the flow chamber during a switch from one reagent to another.

Figure 3A:
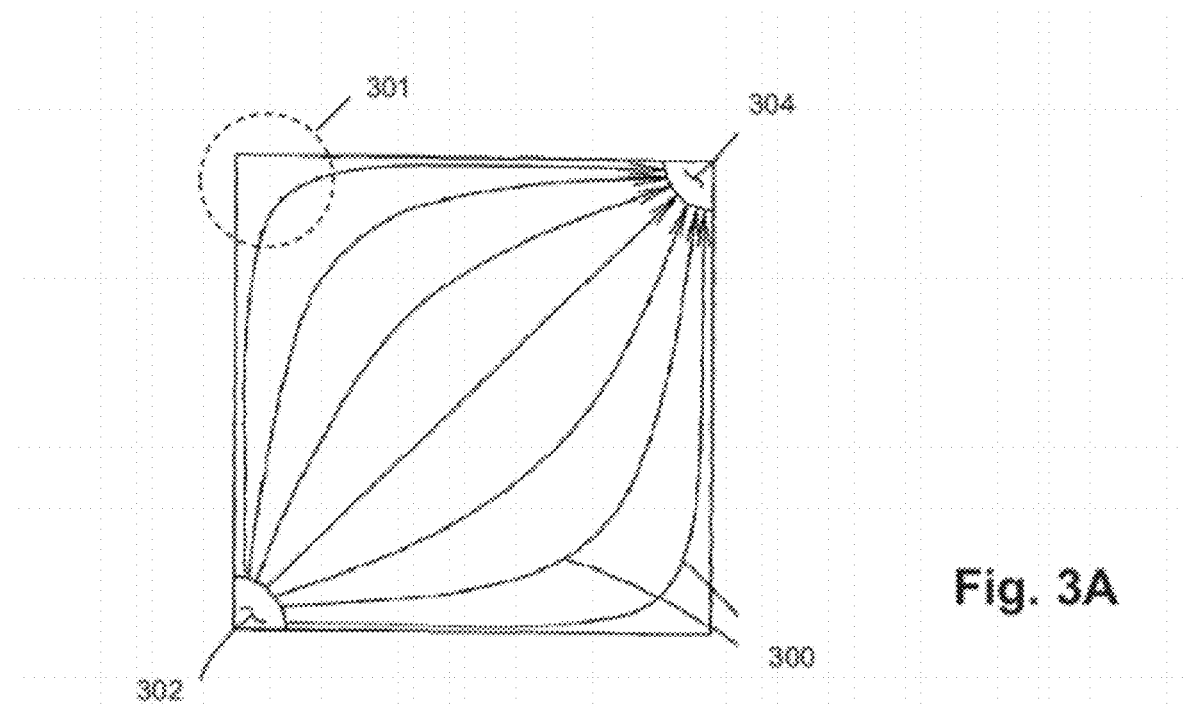
FIG. 3A illustrates exemplary flow paths through an exemplary flow chamber having diagonally opposed inlet and outlet.

FIG. 3A illustrates exemplary flow paths through a flow chamber having diagonally opposed inlet and outlet. The reagents may follow flow paths 300 as they transit along a diagonal axis of the flow chamber between an inlet 302 and an outlet 304, which paths may not reach all the way to corner 301, for example.

In an embodiment, a flow cell may direct reagent flows to an array of microwells such that each microwell is exposed to substantially the same flow conditions, such as flow rate and concentration, for example, at substantially the same time throughout the microwell array as reagents are delivered to the array. (As used herein in reference to such exposure, "substantially the same time" generally refers to the transit time through the flow chamber of a boundary between two successive reagents being small in comparison to the length of time a microwell is exposed to any one reagent.) In an embodiment, a flow cell may have inlets and outlets located diagonally in a flow chamber constrained to a rectilinear space, and in such a configuration achieving identical flow rates at each microwell may not be possible. Nonetheless, any differences in flow conditions experienced by different microwells, such as flow rate, may then preferably be minimized by a flow chamber and the flow path it defines.

Figure 3B:
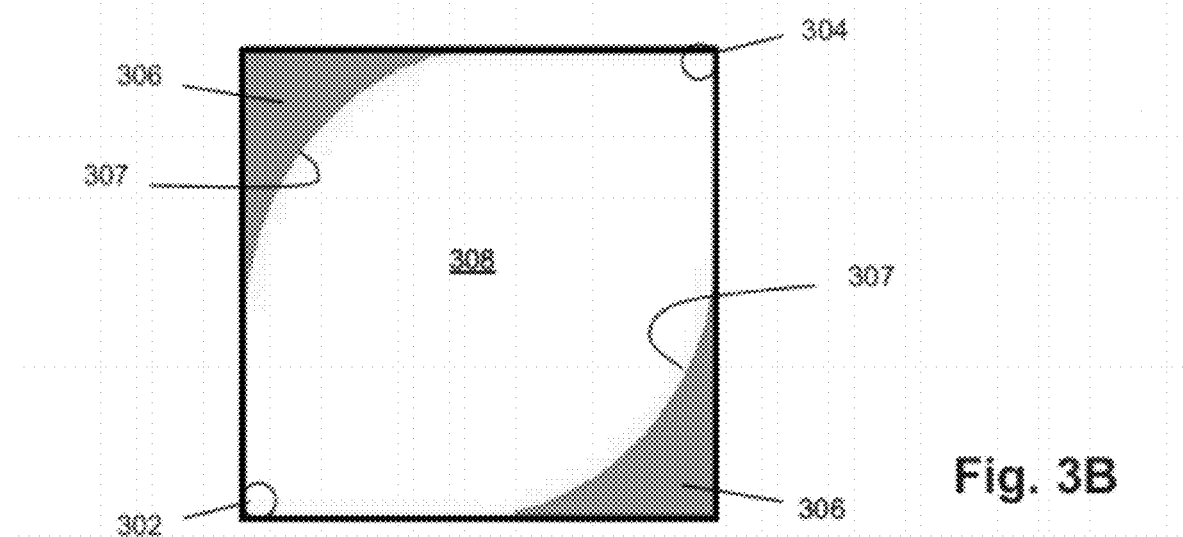
FIG. 3B illustrates an exemplary flow chamber with an exemplary sensor array area defined by reference to a reach of reagent flow paths.

FIG. 3B illustrates an exemplary flow chamber 308 with an exemplary sensor array area defined by reference to a reach of reagent flow paths. The flow chamber may include an area covered by the reagents as they transit from inlet 302 to outlet 304 (excluding an area 306 outside the boundary 307 that delimits an extent of the reagent flow reach in the flow chamber), which area may be used to locate microwells.

Figure 4A:
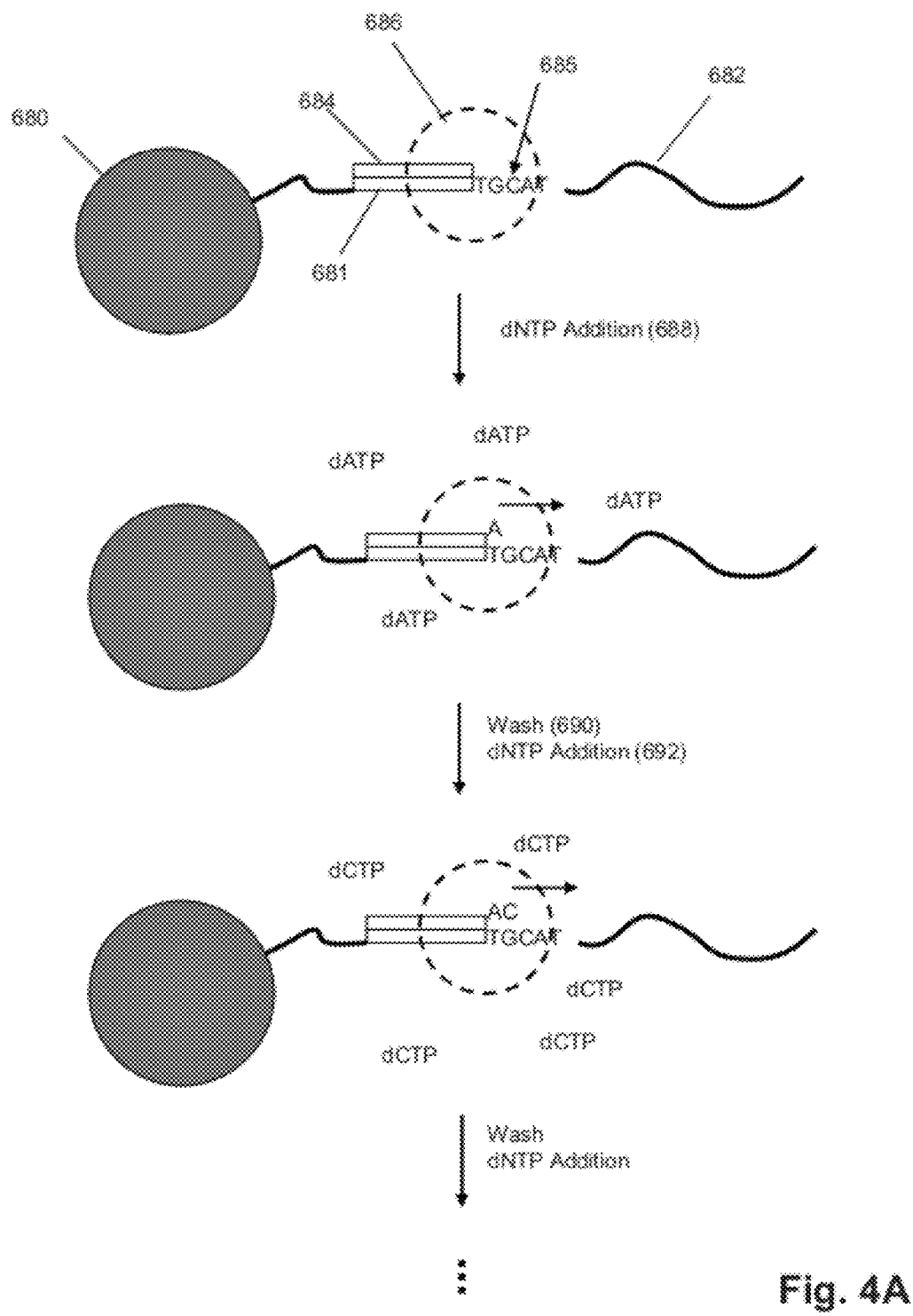
FIGS. 4A and 4B illustrate schematically an exemplary process for label-free, pH-based sequencing.
Figure 4B:
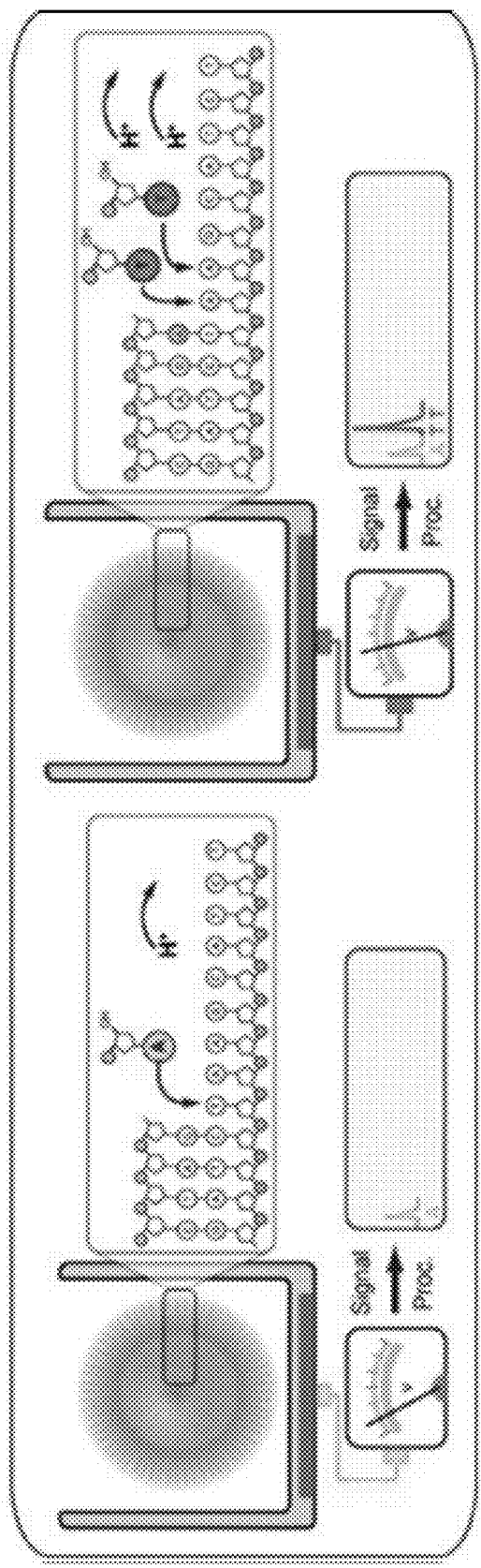

FIGS. 4A and 4B illustrate schematically an exemplary process for label-free, pH-based sequencing. A template 682 with sequence 685 and a primer binding site 681 are attached to a solid phase support 680. The template 682 may be attached as a clonal population to a solid support, such as a microparticle or bead, for example, and may be prepared as disclosed in Leamon et al., U.S. Pat. No. 7,323,305, which is incorporated by reference herein in its entirety. In an embodiment, the template may be associated with a substrate surface or present in a liquid phase with or without being coupled to a support. A primer 684 and DNA polymerase 686 are operably bound to the template 682. As used herein, "operably bound" generally refers to a primer being annealed to a template so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682 and is complementary to the flowed dATP nucleotide). In step 690, a wash is performed. In step 692, the next dNTP (shown as dCTP) is added, and the DNA polymerase 686 incorporates a nucleotide "C" (since "G" is the next nucleotide in the template 682). The pH-based nucleic acid sequencing, in which base incorporations may be determined by measuring hydrogen ions that are generated as natural by-products of polymerase-catalyzed extension reactions, may be performed using at least in part one or more features of Anderson et al., A SYSTEM FOR MULTIPLEXED DIRECT ELECTRICAL DETECTION OF DNA SYNTHESIS, Sensors and Actuators B: Chem., 129:79-86 (2008); Rothberg et al., U.S. Pat. Appl. Publ. No. 2009/0026082; and Pourmand et al., DIRECT ELECTRICAL DETECTION OF DNA SYNTHESIS, Proc. Natl. Acad. Sci., 103:6466-6470 (2006), which are all incorporated by reference herein in their entirety. In an embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles. FIG. 4B further illustrates various aspects of this process, while providing additional details regarding a first nucleotide incorporation (left) leading to a schematic signal representing a single A incorporation, and a second incorporation (right) leading to a schematic signal representing a pair of T incorporations.

In an embodiment, the primer-template-polymerase complex may be subjected to a series of exposures of different nucleotides in a pre-determined sequence or ordering. If one or more nucleotides are incorporated, then the signal resulting from the incorporation reaction may be detected, and after repeated cycles of nucleotide addition, primer extension, and signal acquisition, the nucleotide sequence of the template strand may be determined. The output signals measured throughout this process depend on the number of nucleotide incorporations. Specifically, in each addition step, the polymerase extends the primer by incorporating added dNTP only if the next base in the template is complementary to the added dNTP. If there is one complementary base, there is one incorporation; if two, there are two incorporations; if three, there are three incorporations, and so on. With each incorporation, an hydrogen ion is released, and collectively a population released hydrogen ions change the local pH of the reaction chamber. The production of hydrogen ions may be monotonically related to the number of contiguous complementary bases in the template (as well as to the total number of template molecules with primer and polymerase that participate in an extension reaction). Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer," "2-mer," "3-mer" output signals, etc.). If the next base in the template is not complementary to the added dNTP, then no incorporation occurs and no hydrogen ion is released (and the output signal is then sometimes referred to as a "0-mer" output signal). In each wash step of the cycle, an unbuffered wash solution at a predetermined pH may be used to remove the dNTP of the previous step in order to prevent misincorporations in later cycles. In an embodiment, the four different kinds of dNTP are added sequentially to the reaction chambers, so that each reaction is exposed to the four different dNTPs, one at a time. In an embodiment, the four different kinds of dNTP are added in the following sequence: dATP, dCTP, dGTP, dTTP, dATP, dCTP, dGTP, dTTP, etc., with each exposure, incorporation, and detection steps followed by a wash step. Each exposure to a nucleotide followed by a washing step can be considered a "nucleotide flow." Four consecutive nucleotide flows can be considered a "cycle." For example, a two cycle nucleotide flow order can be represented by: dATP, dCTP, dGTP, dTTP, dATP, dCTP, dGTP, dTTP, with each exposure being followed by a wash step. Different flow orders are of course possible.

Figure 4C:
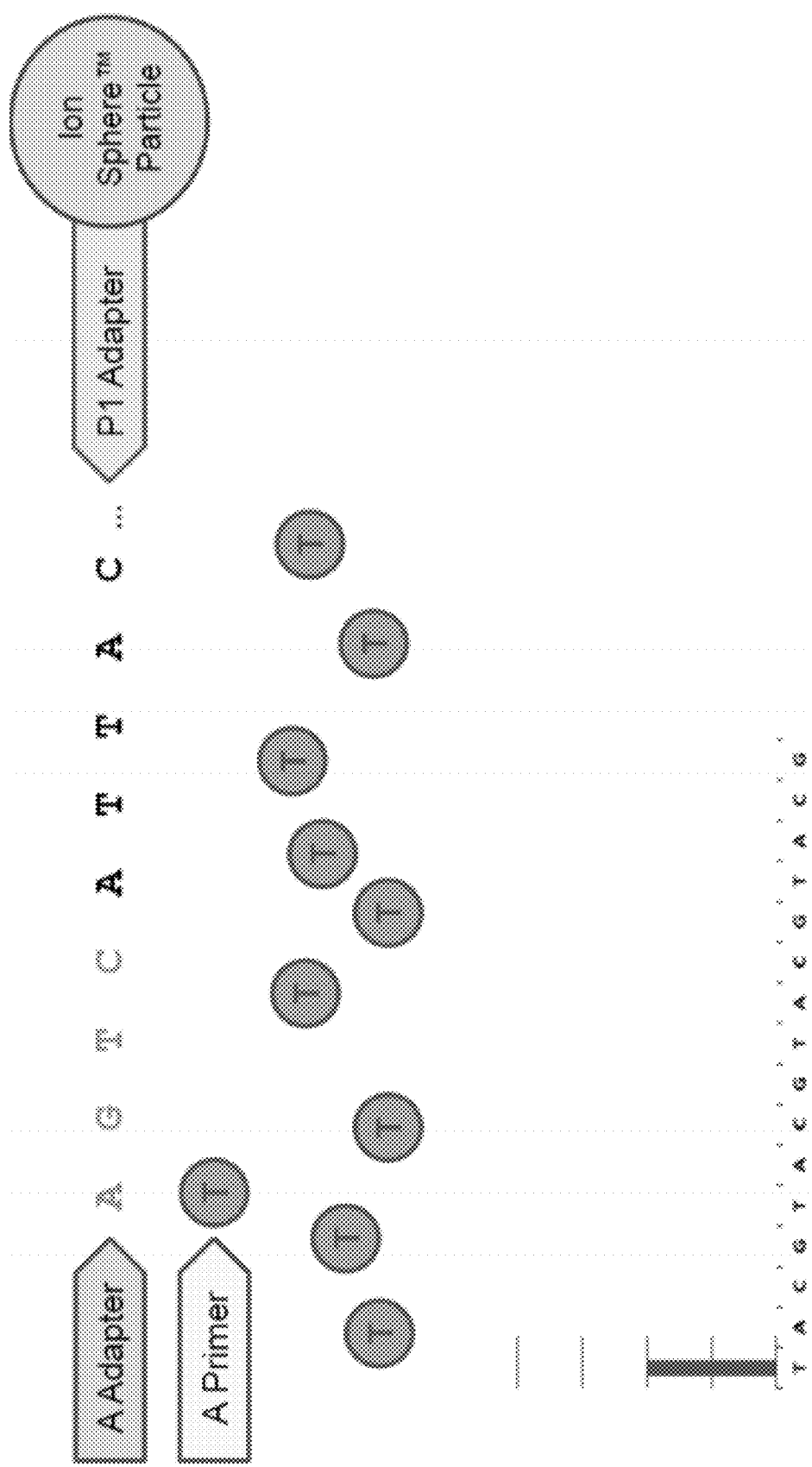
FIGS. 4C-4P illustrate schematically exemplary flow-based steps for sequencing a target using sequencing-by-synthesis.
Figure 4D:
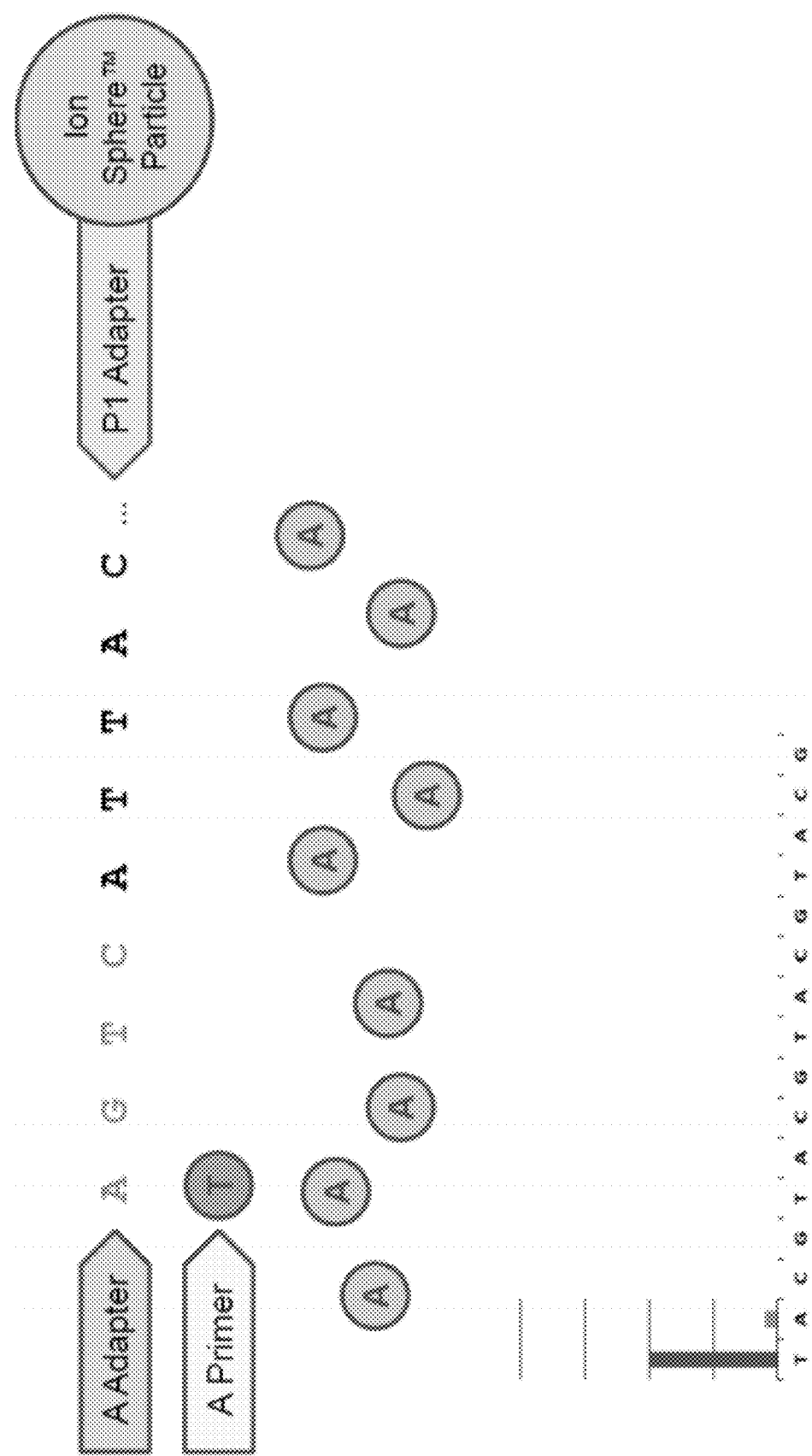
FIG. 4Q illustrates exemplary raw pH-based sequencing data corresponding to counts associated with a plurality of nucleotide flows.
FIG. 4R illustrates exemplary flow-by-flow numerical values corresponding to raw pH-based sequencing data from which homopolymer length predictions can be made.
Figure 4E:
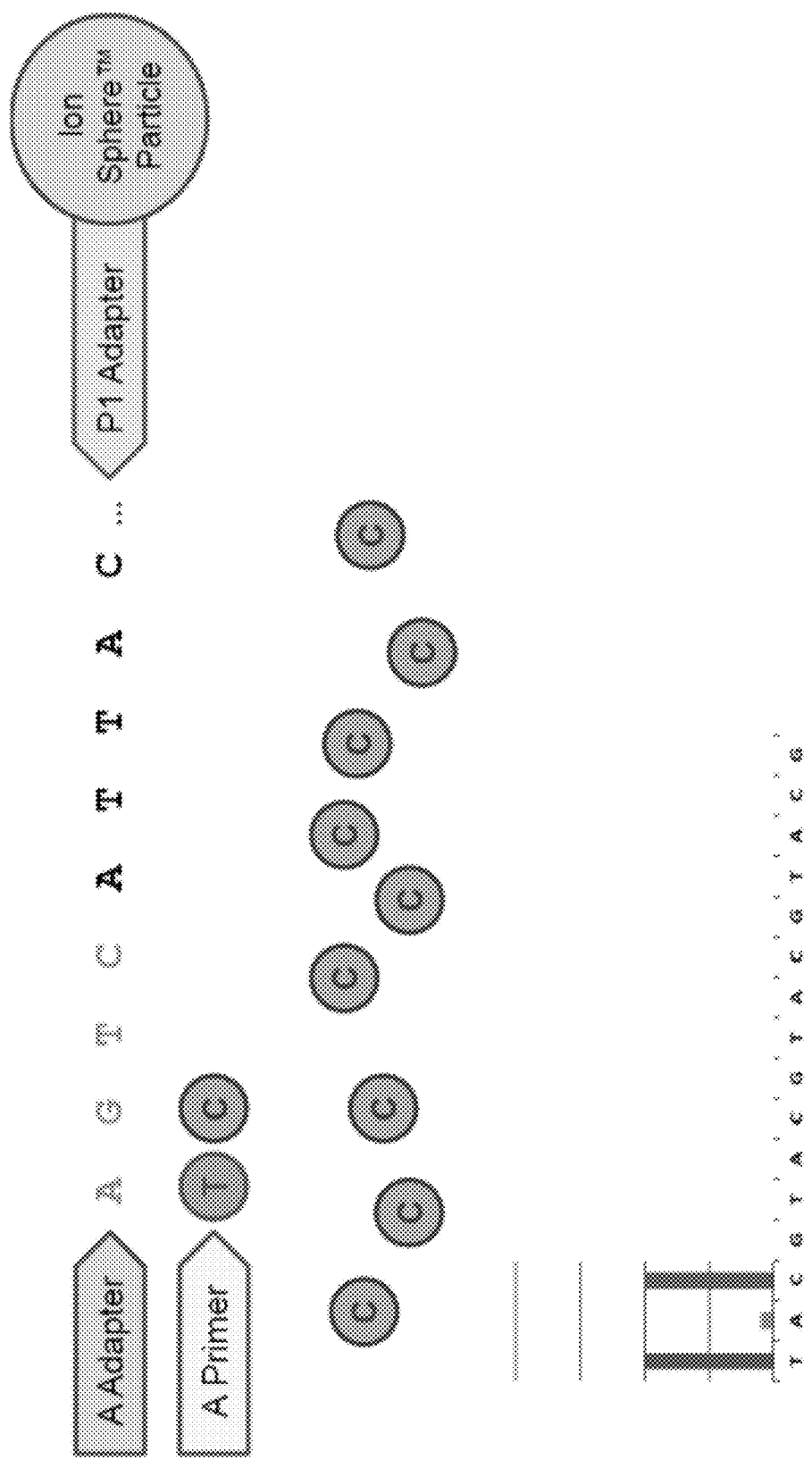
Figure 4F:
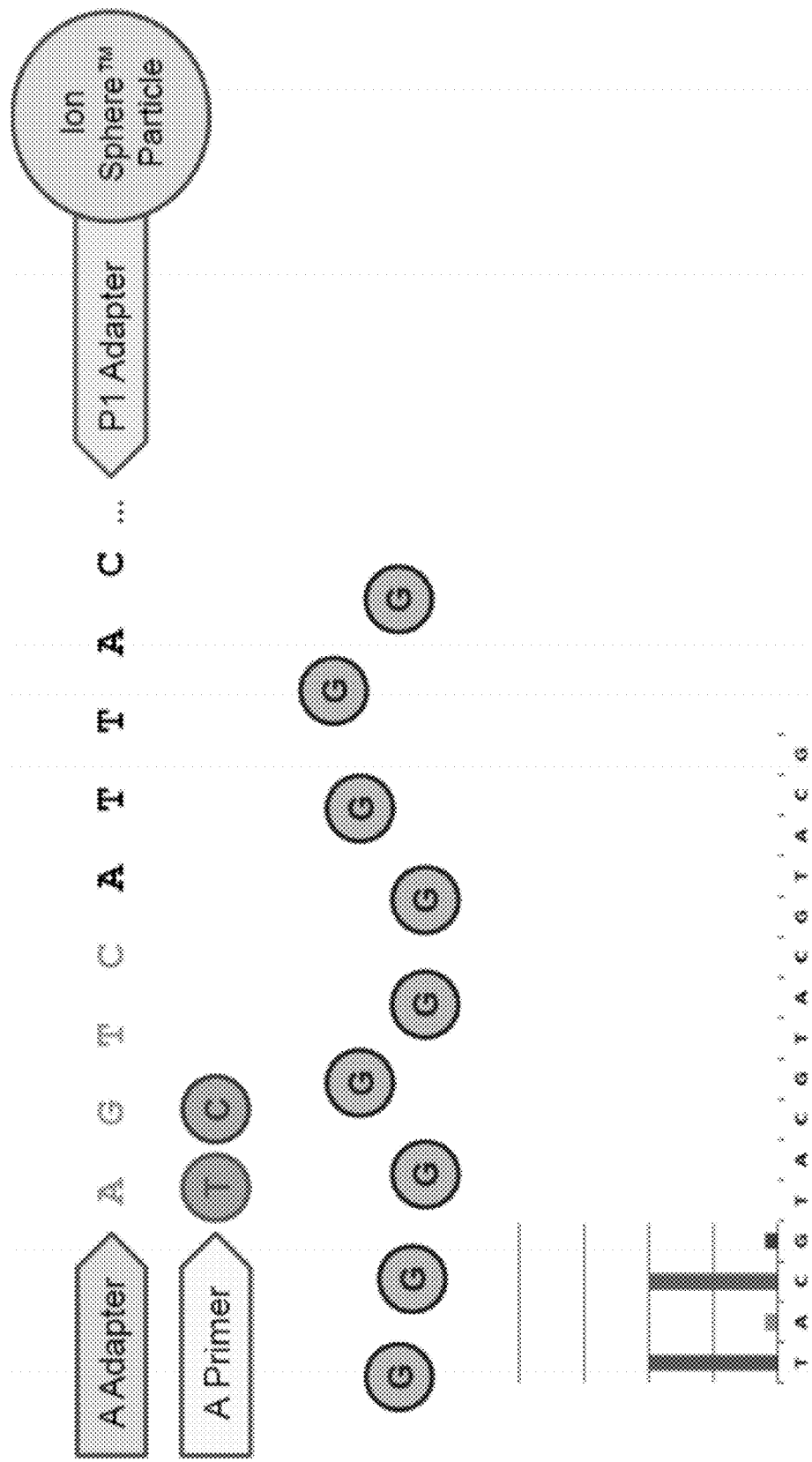
Figure 4G:
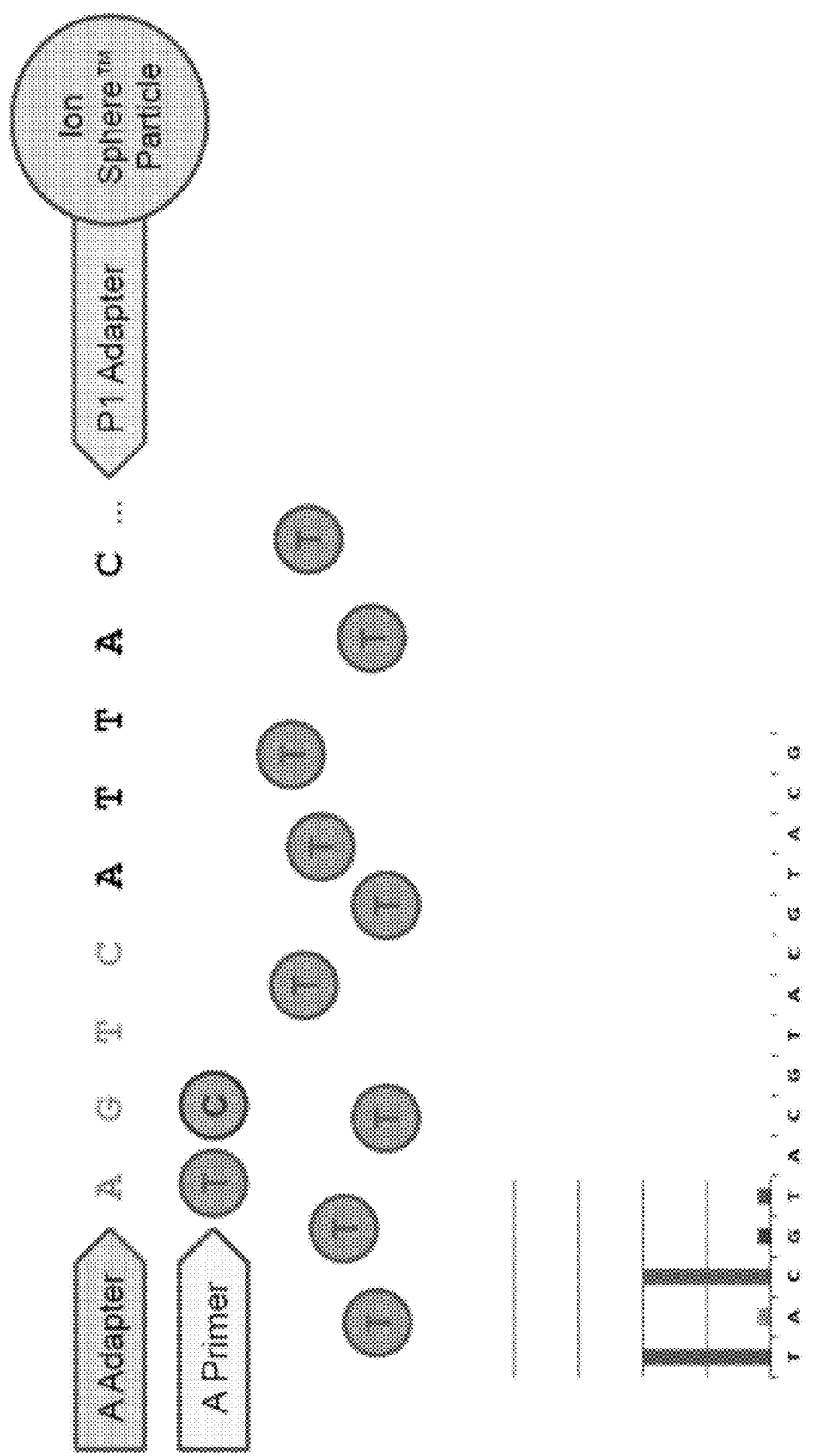
Figure 4H:
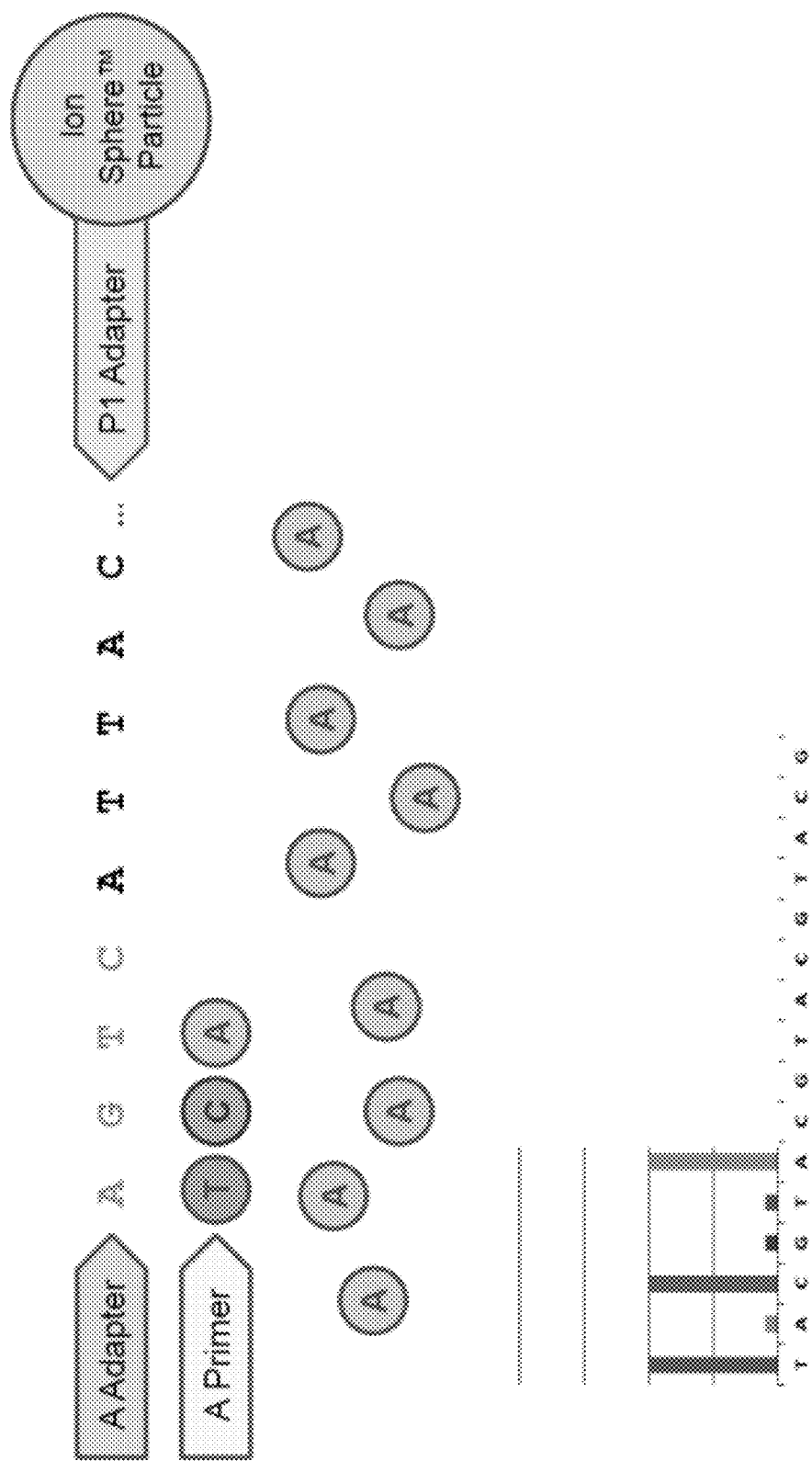
Figure 41:
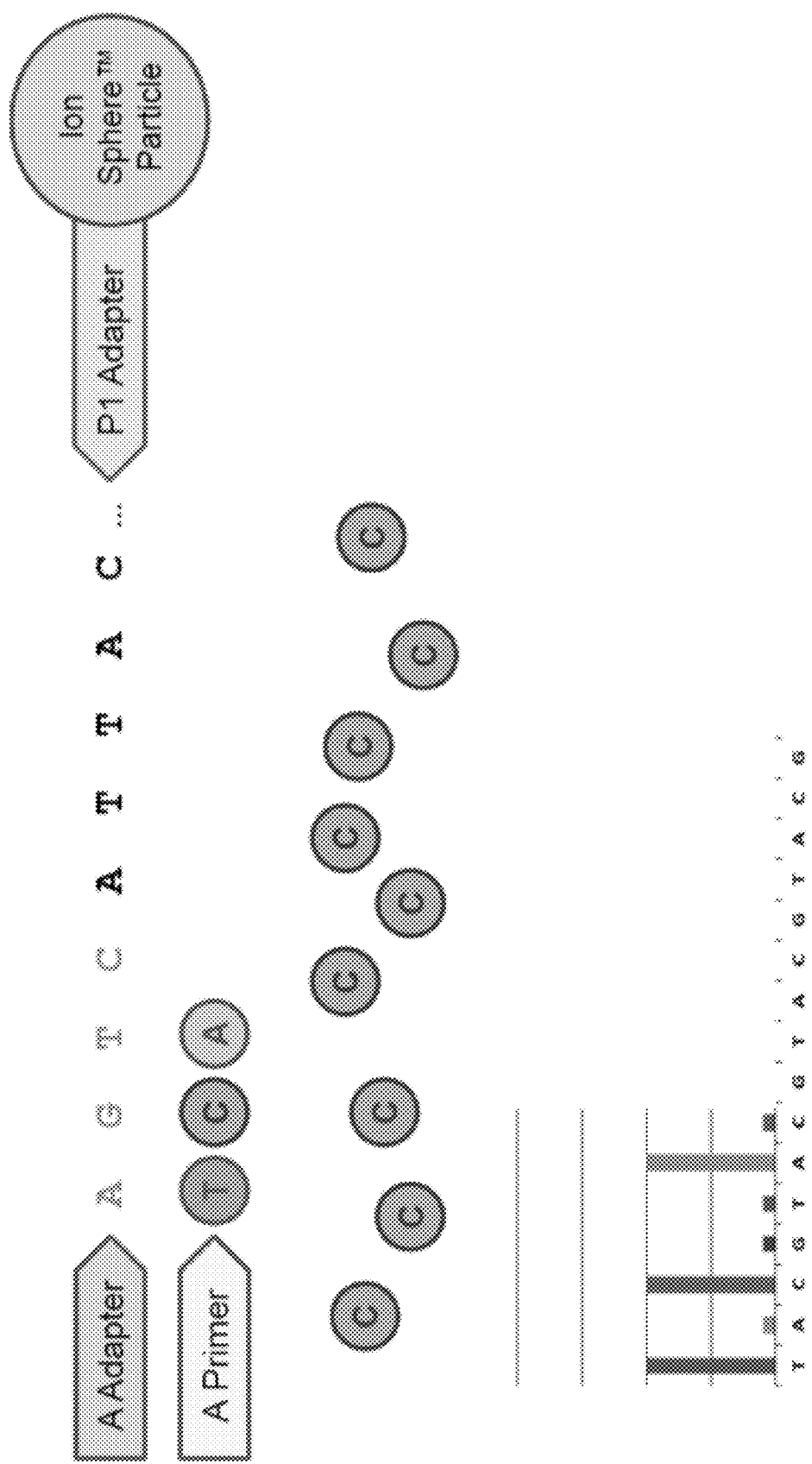
Figure 4J:
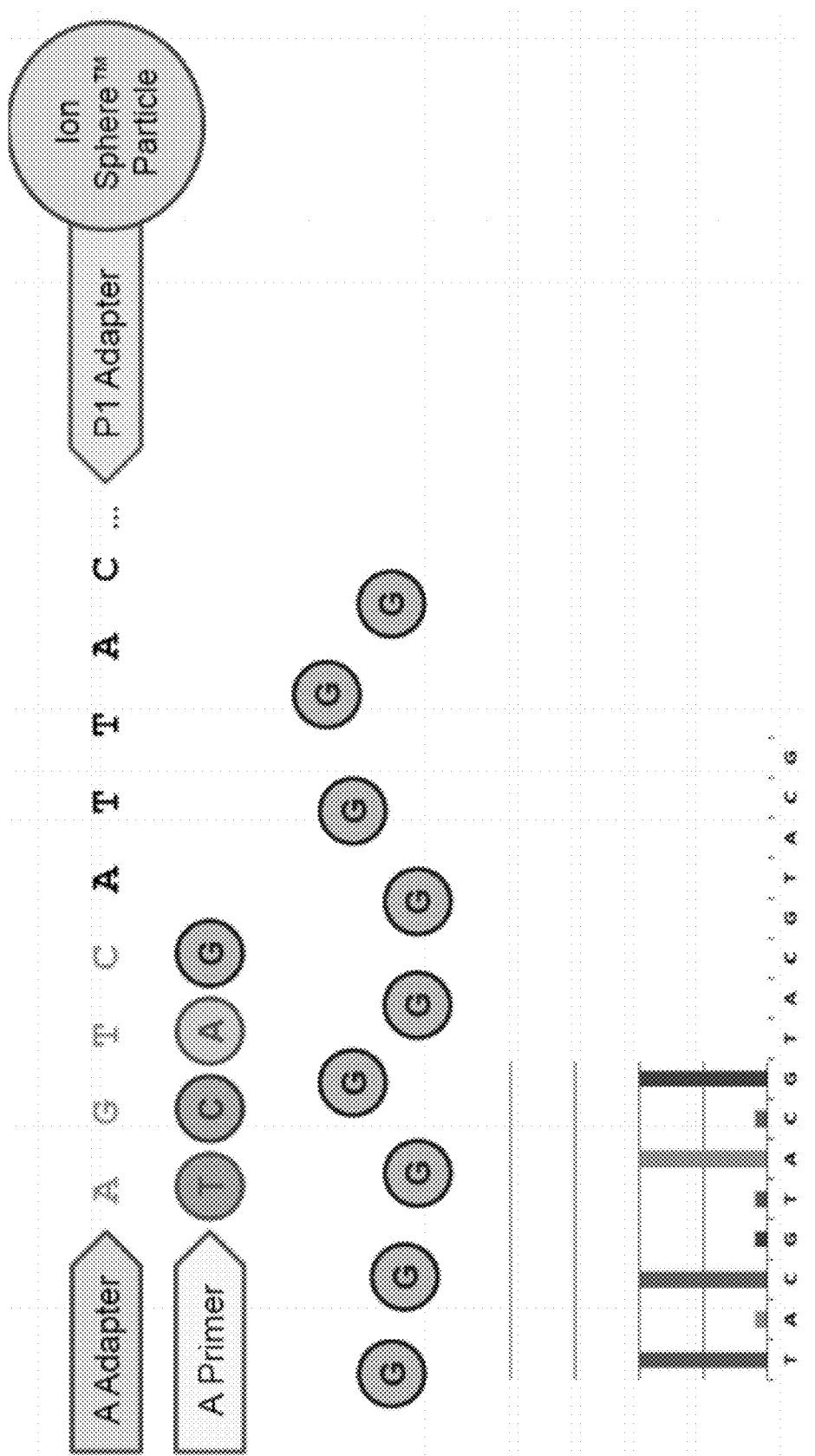
Figure 4K:
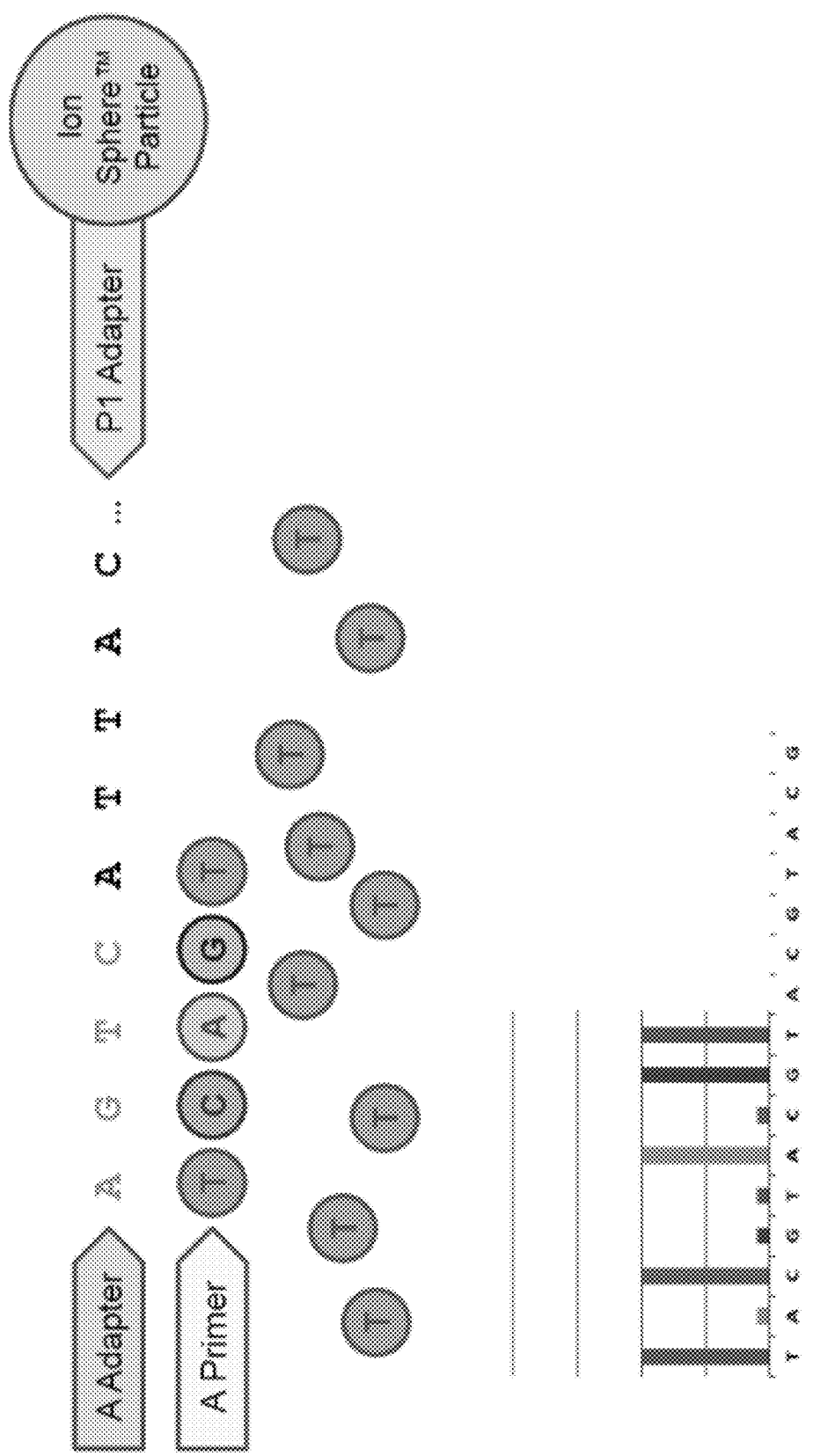
Figure 4L:
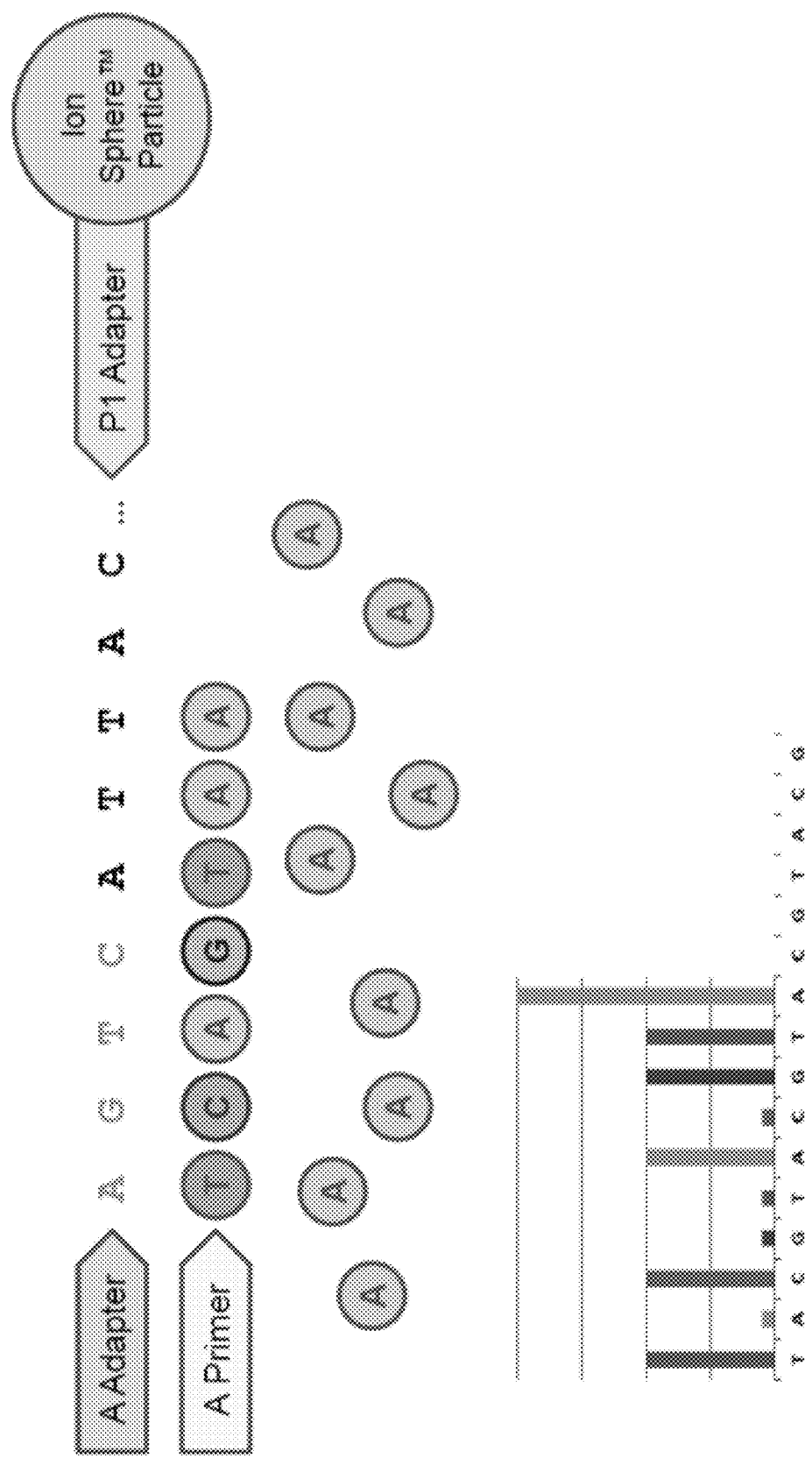
Figure 4M:
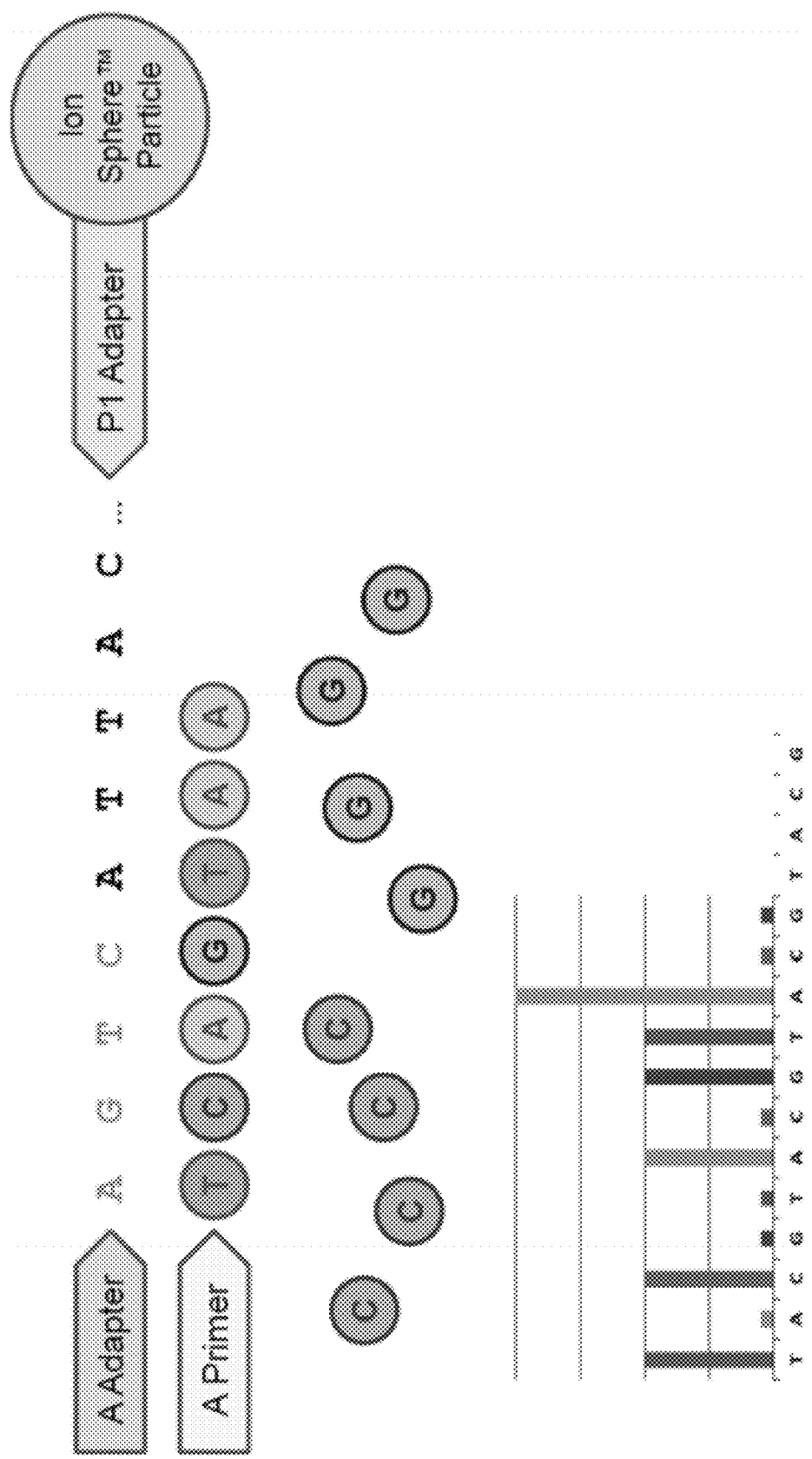
Figure 4N:
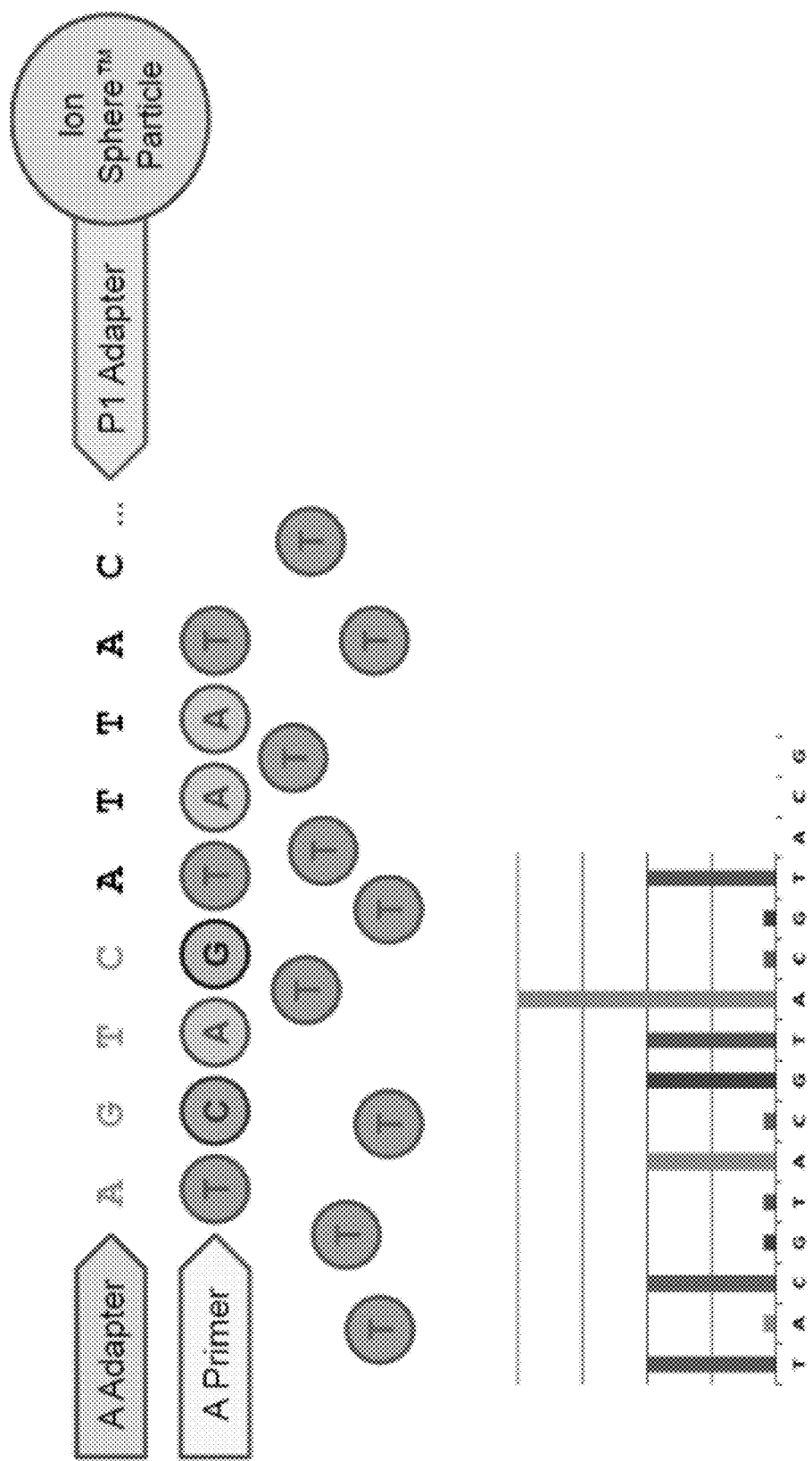
Figure 40:
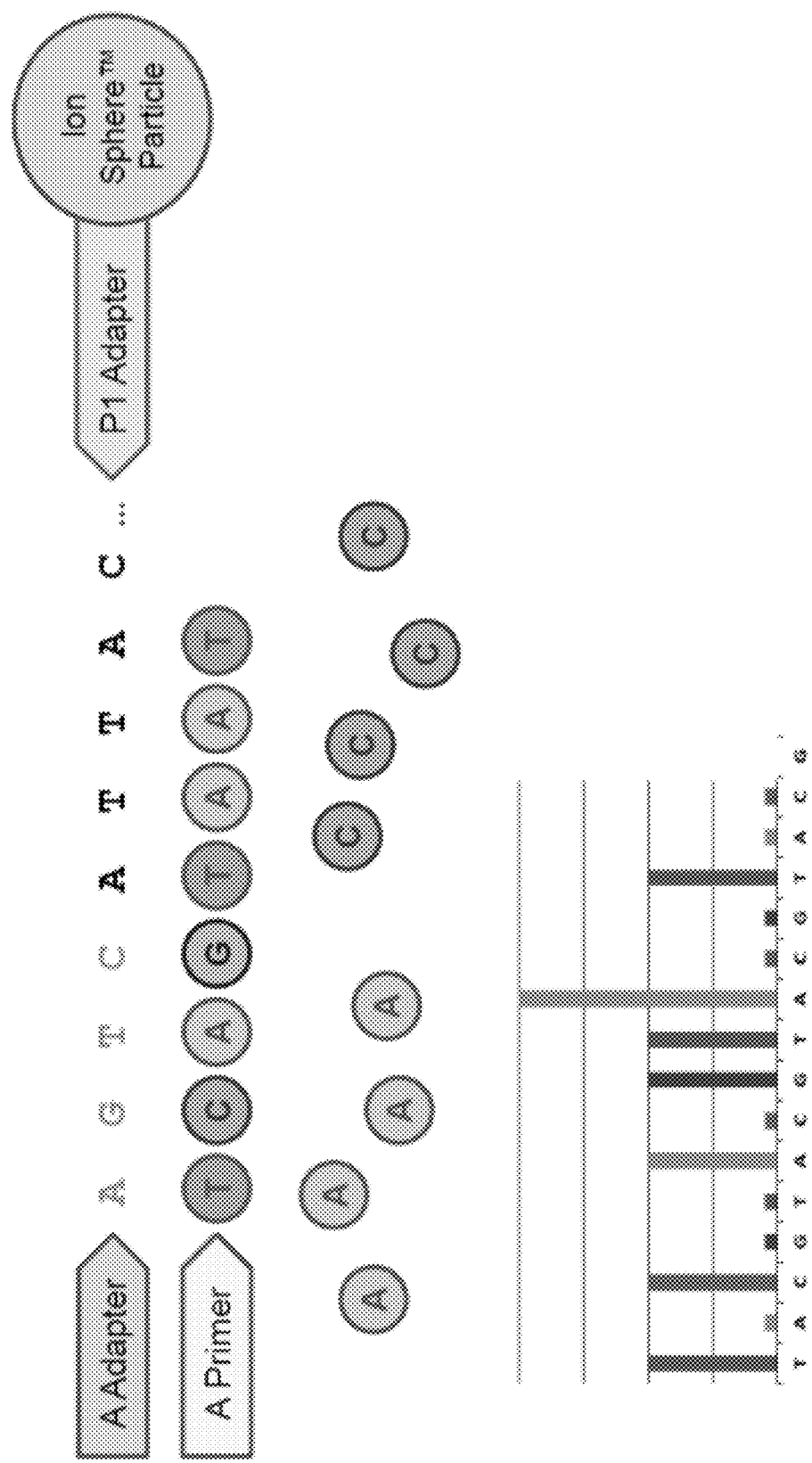
Figure 4P:
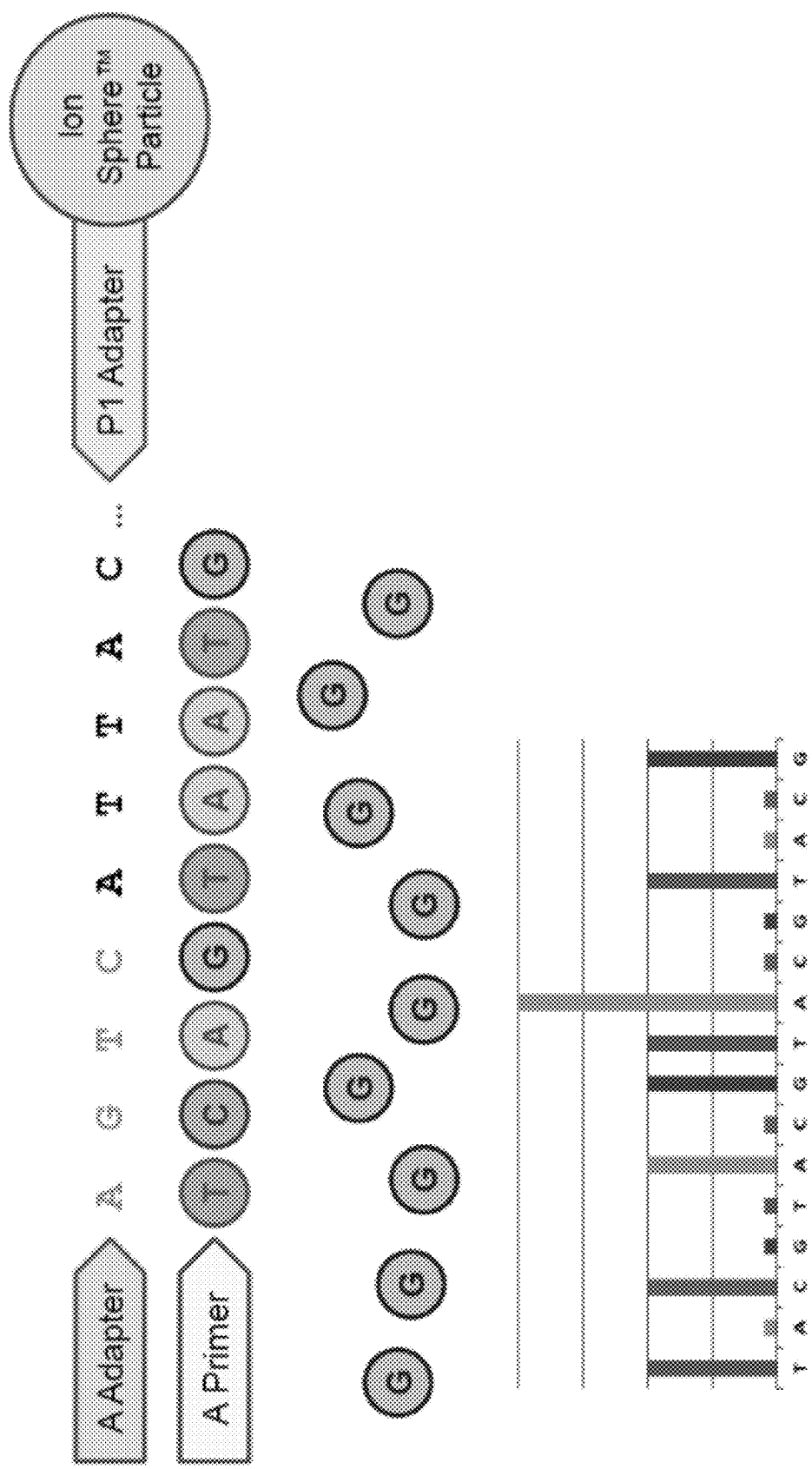

FIGS. 4C-4P illustrate schematically exemplary flow-based steps for sequencing a target using sequencing-by-synthesis. The example of target illustrated here includes, for example, an A adapter, a sequencing key or code ("AGTC" in this example), a sequence of interest ("ATTAC . . . " in this example), and a P1 adapter attached to or associated with a particle (for example). FIG. 4C illustrates a first flow of T nucleotide species, which leads to a single incorporation (a T "1-mer") because the first available base is A, which is complementary. FIG. 4D illustrates a second flow of A nucleotide species, which leads to no incorporation (an A "0-mer") because the next available base is G, which is not complementary. FIG. 4E illustrates a third flow of C nucleotide species, which leads to a single incorporation (a C "1-mer") because the next available base is G, which is complementary. FIG. 4F illustrates a fourth flow of G nucleotide species, which leads to no incorporation (a G "0-mer") because the next available base is T, which is not complementary. FIG. 4G illustrates a fifth flow of T nucleotide species, which leads to no incorporation (a T "0-mer") because the next available base is T, which is not complementary. FIG. 4H illustrates a sixth flow of A nucleotide species, which leads to a single incorporation (an A "1-mer") because the next available base is T, which is complementary. FIG. 4I illustrates a seventh flow of C nucleotide species, which leads to no incorporation (a C "0-mer") because the next available base is C, which is not complementary. FIG. 4J illustrates an eighth flow of G nucleotide species, which leads to a single incorporation (a G "1-mer") because the next available base is C, which is complementary. FIG. 4K illustrates a ninth flow of T nucleotide species, which leads to a single incorporation (a T "1-mer") because the next available base is A, which is complementary. FIG. 4L illustrates a tenth flow of A nucleotide species, which leads to a double incorporation (an A "2-mer") because the next two available bases are T, which are complementary. FIG. 4M illustrates an eleventh flow of C nucleotide species and a twelfth flow of G nucleotide species, which lead to no incorporation (C and G "0-mers") because the next available base is A, which is not complementary. FIG. 4N illustrates a thirteenth flow of T nucleotide species, which leads to a single incorporation (a T "1-mer") because the next available base is A, which is complementary. FIG. 4O illustrates a fourteenth flow of A nucleotide species and a fifteenth flow of C nucleotide species, which lead to no incorporation (A and C "0-mers") because the next available base is C, which is not complementary. Finally, FIG. 4P illustrates a sixteenth flow of G nucleotide species, which leads to a single incorporation (a G "1-mer") because the next available base is C, which is complementary. In each case, a signal proportional to the homopolymer length (e.g., 0, 1, 2, . . . ) is also illustrated. Although the flow ordering in the example of FIGS. 4C-4P was according to "TACG TACG . . . ," other flows, such as any of the various phase-protecting reagent flow orderings discussed herein, could also be used.

Figure 4Q:
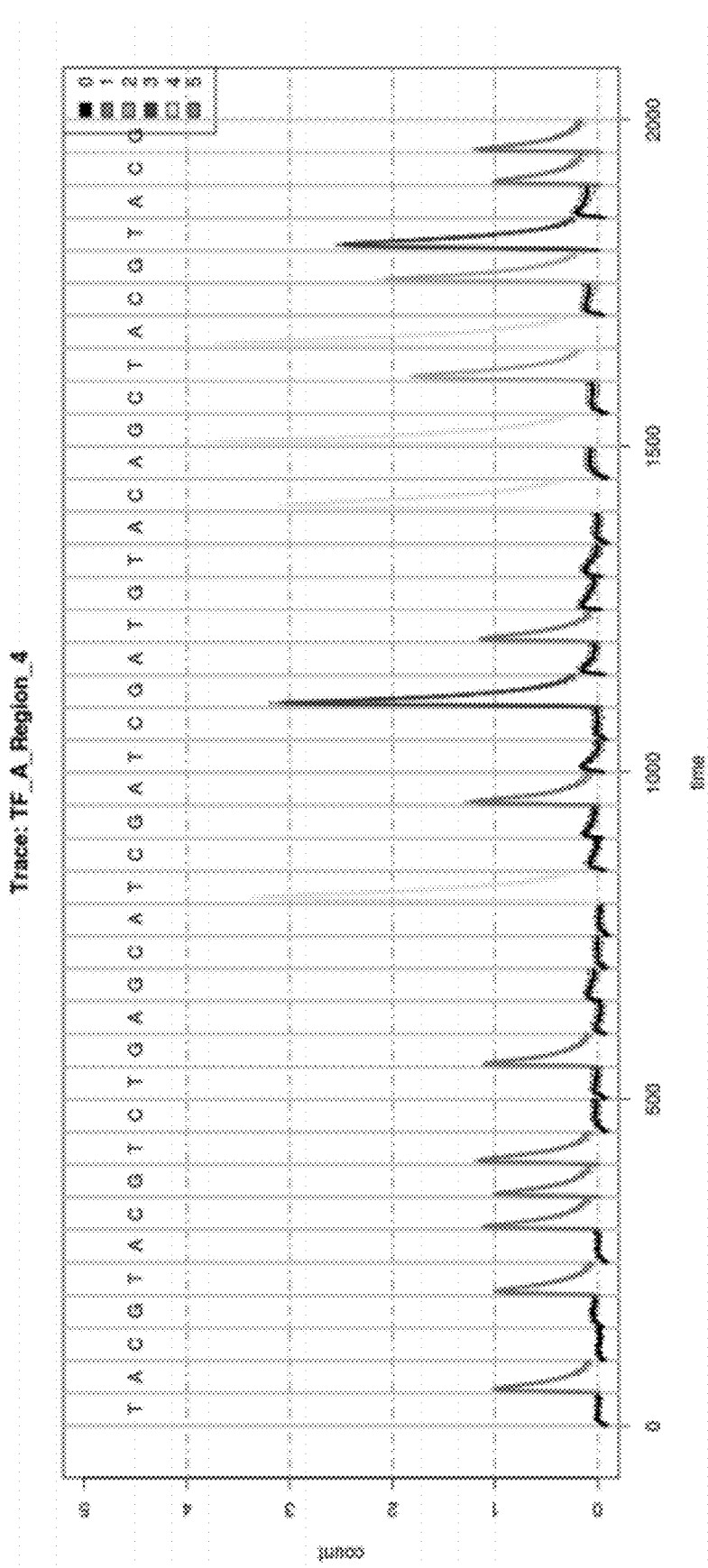

FIG. 4Q illustrates exemplary raw pH-based sequencing data corresponding to counts associated with a plurality of nucleotide flows. In this example, the reagent flow ordering is "TACG TACG TCTG AGCA TCGA TCGA TGTA CAGC" (SEQ ID NO: 7) (flowed in whole once and then followed by its first eight flows). The counts on the y-axis are scaled values that may be viewed as representative of a voltage output signal that should generally be proportional in magnitude to the number of nucleotide incorporations likely to have resulted in response to each of the various nucleotide flows. In other words, the signal should remain close to the baseline for a 0-mer, should attain approximately 1 for a 1-mer, should attain approximately 2 for a 2-mer, should attain approximately 3 for a 3-mer, and so on. The x-axis represents time.

Figure 4R:
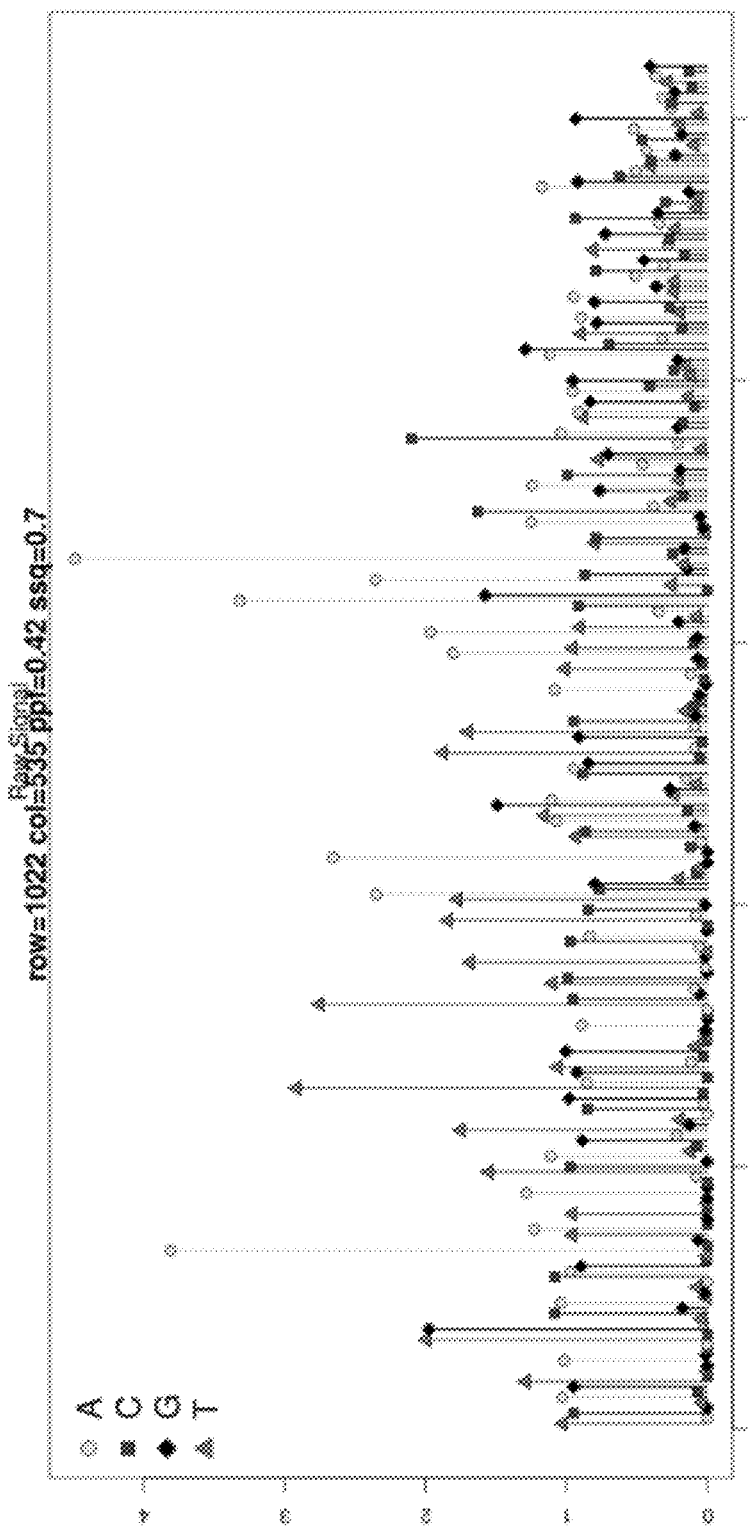

FIG. 4R illustrates exemplary flow-by-flow numerical values corresponding to raw pH-based sequencing data from which homopolymer length predictions can be made. For every particular flow (the type of which is indicated by a circle for A, a square for C, a diamond for G, and a triangle for T), there corresponds a numerical value from which homopolymer length can be determined. In this example, the first flow of T shows a value around 1, suggesting a single incorporation of T; the second flow of A shows a value around 0, suggesting no incorporation of A, and so on. Based on knowledge of such predicted homopolymer lengths having resulted from each flow in the predetermined ordering of flows, a likely sequence of the target may be inferred.

In various embodiments, output signals due to nucleotide incorporation may be processed in various way to improve their quality and/or signal-to-noise ratio, which may include performing or implementing one or more of the teachings disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No 61/428,097, filed Dec. 29, 2010, which are all incorporated by reference herein in their entirety.

In various embodiments, output signals due to nucleotide incorporation may be further processed, given knowledge of what nucleotide species were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal droop (e.g, enzyme efficiency loss) estimations, and signal corrections, and may identify or estimate base calls for each flow for each defined space. Base calling may include performing or implementing one or more of the teachings disclosed in Davey et al., U.S. patent application Ser. No. 13/283,320, filed Oct. 27, 2011, based on U.S. Prov. Pat. Appl. No. 61/407,377, filed on Oct. 27, 2010, which are both incorporated by reference herein in their entirety. Other aspects of signal processing and base calling may include performing or implementing one or more of the teachings disclosed in Davey et al., U.S. patent application Ser. No. 13/340,490, filed on Dec. 29, 2011, based on U.S. Prov. Pat. Appl. No. 61/428,733, filed on Dec. 30, 2010, which are all incorporated by reference herein in their entirety.

The accuracy of sequencing and the efficiency with which sequencing may be performed can be impacted by several types of sequencing errors that may arise when using sequencing-by-synthesis. Some of these errors are related to synchrony issues. Specifically, a large population of substantially identical template strands (e.g., $10^3$ to $10^7$ molecules) may be analyzed substantially simultaneously in a given sequencing reaction to obtain sufficiently distinct and resolvable signals for reliable detection in sequencing-by-synthesis, and it is desirable that synthesis for the strands proceed in step or in phasic synchrony with each other. Signal-to-noise ratios may be improved when there is homogeneous and/or contemporaneous extension of the complementary strand associated with the template molecules in a population. Each extension reaction associated with the population of template molecules may be described as being generally "in phase" or in "phasic synchrony" with each other when they are performing the same incorporation step at the same sequence position for the associated template molecules in a given reaction step. It has been observed, however, that a relatively small fraction of template molecules in each population may lose or fall out of phasic synchrony (e.g., may become "out of phase") with the majority of the template molecules in the population. That is, the incorporation events associated with a certain fraction of template molecules may either get ahead of or fall behind other similar template molecules in the sequencing run. Such phase loss effects are described in Ronaghi, GENOME RESEARCH, 11:3-11 (2001); Leamon et al., CHEMICAL REVIEWS, 107:3367-3376 (2007); Chen et al., International Publ. No. WO 2007/098049.

One such phase loss effect relates to an "incomplete extension" (IE) event or error. An IE event may occur as a result of a failure of a sequencing reaction to incorporate one or more nucleotide species into one or more nascent molecules for a given extension round of the sequence, for example, which may result in subsequent reactions being at a sequence position that is out of phase with the sequence position for the majority of the population (e.g., certain template extensions fall behind the main template population). IE events may arise, for example, because of a lack of nucleotide availability to a portion of the template/polymerase complexes of a population, or because of a failure of a portion of the polymerase molecules to incorporate a nucleotide into a complementary strand at the appropriate time, because of a loss of polymerase activity, or because of some other relevant cause or factor.

Another such phase loss effect relates to a "carry forward" (CF) event or error. A CF event may occur as a result of an improper extension of a nascent molecule by incorporation of one or more nucleotide species in a sequence or strand position that is ahead and out of phase with the sequence or strand position of the rest of the population. CF events may arise, for example, because of the misincorporation of a nucleotide species, or in certain instances, because of contamination or excess nucleotides remaining from a previous cycle (e.g., which may result from an insufficient or incomplete washing of the reaction chamber). For example, a small fraction of a "T" nucleotide cycle may be present or carry forward to a "C" nucleotide cycle. The presence of both nucleotides may lead to an undesirable extension of a fraction of the growing strands where the "T" nucleotide is incorporated in addition to the "C" nucleotide such that multiple different nucleotide incorporations events take place where only a single type of nucleotide incorporation would normally be expected. CF events may also arise because of a polymerase error (e.g., there may be an improper incorporation of a nucleotide species into the nascent molecule that is not complementary to the nucleotide species on the template molecule).

Figure 5:
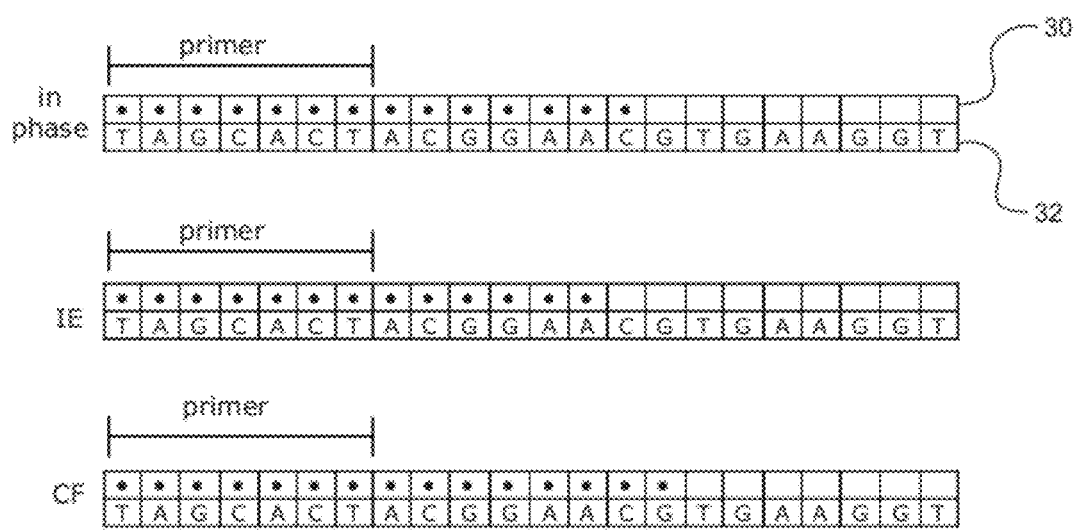
FIG. 5 illustrates exemplary incomplete extension (IE) and carry forward (CF) events that may occur and result in loss of phasic synchrony during sequencing-by-synthesis.

FIG. 5 illustrates exemplary IE and CF events that may occur and result in loss of phasic synchrony during sequencing-by-synthesis. It shows three DNA duplexes. For each duplex, the bottom row of boxes represents the template polynucleotide strand 32 and the top row of boxes represents the complementary extension strand 30 being extended by a polymerase. The extension strand includes the primer portion, as indicated by the bar. The (●)-filled boxes indicate the incorporation of complementary nucleotides. The top DNA duplex (labeled "in-phase") represents members of the population that are in the correct phase. The middle DNA duplex (labeled "IE") represents a portion of the population that has experienced an omission at the C nucleotide (an IE error). The bottom DNA duplex (labeled "CF") represents a portion of the population that has experienced an erroneous incorporation at the G nucleotide (a CF error).

Errors or phasing issues related to IE and CF events may be exacerbated over time because of the accumulation of such events, which may cause degradation of sequence signal or quality over time and an overall reduction in the practical read length of the system (e.g., the number of nucleotides that can be sequenced for a given template). The present teachings reflect the discovery that sequencing performance (e.g., efficiency and/or accuracy of sequencing) may be affected by the particular composition, nature, and sequence of nucleotides delivered to sequencing-by-synthesis reactions.

According to various embodiments, there are provided methods, systems, apparatuses, and computer readable media for performing sequencing-by-synthesis while reducing or minimizing sequencing errors associated with the aforementioned phase loss effects that may occur with sequencing-by-synthesis. The methods, systems, apparatuses, and computer readable media may include steps and/or structural elements for performing sequencing-by-synthesis using reagents that are flowed according to a predetermined ordering. Although the predetermined ordering may be based on a cyclical, repeating pattern consisting of consecutive repeats of a short pre-determined reagent flow ordering (e.g., consecutive repeats of a pre-determined sequences of four nucleotide reagents, for example), the predetermined ordering may advantageously comprise in whole or in part a phase-protecting reagent flow ordering as described herein.

Figure 6A:
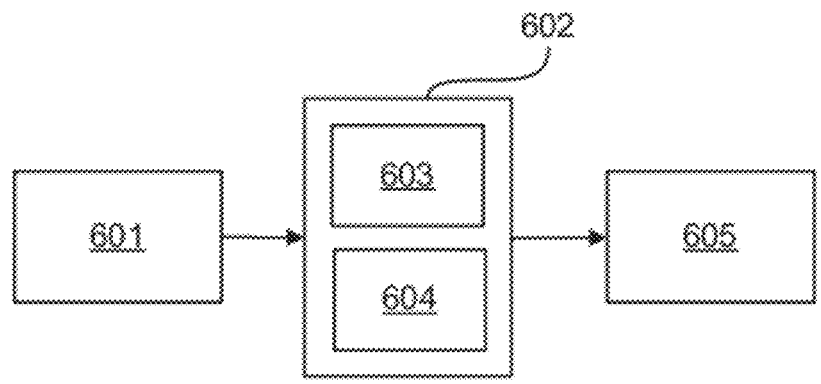
FIG. 6A illustrates an exemplary system for obtaining, processing, and/or analyzing nucleic acid sequencing data.

FIG. 6A illustrates an exemplary system for obtaining, processing, and/or analyzing nucleic acid sequencing data. The system includes a sequencing instrument 601, a server 602 or other computing means or resource, and one or more end user computers 605 or other computing means or resource. The sequencing instrument 601 may be configured to deliver reagents according to a predetermined ordering, which may be based on a cyclical, repeating pattern consisting of consecutive repeats of a short pre-determined reagent flow ordering (e.g., consecutive repeats of pre-determined sequence of four nucleotide reagents such as "TACG TACG . . . "), or may be based on an ordering comprising in whole or in part a phase-protecting reagent flow ordering as described herein, or some combination thereof. The server 602 may include a processor 603 and a memory and/or database 604. The sequencing instrument 601 and the server 602 may include one or more computer readable media for obtaining, processing, and/or analyzing nucleic acid sequencing data. In an embodiment, the instrument and the server or other computing means or resource may be configured as a single component. One or more of these components may be used to perform or implement one or more aspects of the embodiments described herein.

Figure 6B:
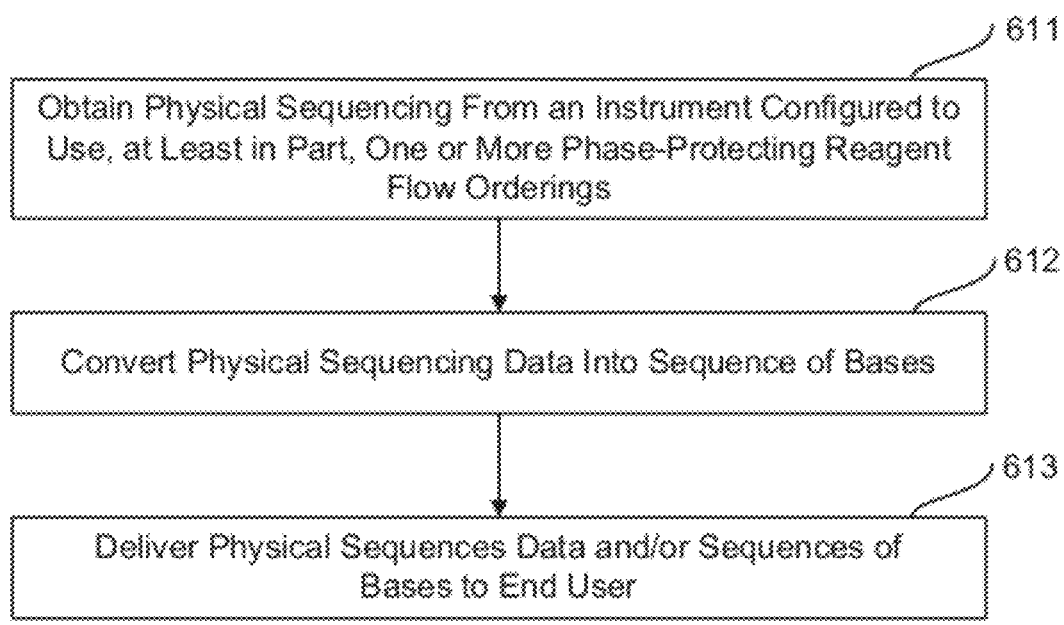
FIG. 6B illustrates an exemplary method for obtaining, processing, and/or analyzing nucleic acid sequencing data.

FIG. 6B illustrates an exemplary method for obtaining, processing, and/or analyzing nucleic acid sequencing data. In step 611, a user obtains physical sequencing data from an instrument configured to use, at least in part, one or more phase-protecting reagent flow orderings. The physical sequencing data may include voltage data indicative of hydrogen ion concentrations, for example, and may be based on a cyclical, repeating pattern consisting of consecutive repeats of a short pre-determined reagent flow ordering (e.g., consecutive repeats of pre-determined sequence of four nucleotide reagents such as "TACG TACG . . . "), or may be based on an ordering comprising in whole or in part a phase-protecting reagent flow ordering as described herein, or some combination thereof, for example. In step 612, a server or other computing means or resource converts the physical sequencing data into sequences of bases. In step 613, the server or other computing means or resource delivers the physical sequencing data and/or sequences of bases to an end user. One or more of these steps and/or components may be used to perform or implement one or more aspects of the embodiments described herein.

In an embodiment, a predetermined permutation of four distinct reagent flows (e.g, any of the possible 4-flow permutations of A, C, T, and G, such as ACTG, CATG, GATC, or CTAG, for example) may be repeatedly delivered (flowed) consecutively and always in the same order. For example, the first nucleotide delivered may be dATP, then dCTP, then dGTP, then dTTP (or a permutation thereof), after which this sequence of four nucleotides (which may be called a "cycle") may be repeated any number of times consecutively. Deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP." In each flow, a polymerase may generally extend the primer by incorporating the flowed dNTP where the next base in the template strand is the complement of the flowed dNTP. When using such cyclical, consecutively repeating flows, however, out-of-sync templates generally will not be given an opportunity to resynchronize with the in-sync population, which may lead to phase-related sequencing errors. Further, while such cyclical, consecutively repeating flows can be generally efficient at extending sequence obtained per flow, as the next unknown base is guaranteed to be resolved within three flows of the present flow, such an approach may be problematic as such flow orders provide no opportunities for phase-protection.

According to various embodiments, sequencing-by-synthesis reactions may be performed using a flow ordering comprising in whole or in part a phase-protecting reagent flow ordering, which may help reduce and/or correct the loss of phasic synchrony in the population of template polynucleotide strands that may result from IE and/or CF events. In particular, such flow orderings may give out-of-sync templates an opportunity to resynchronize (move into the same phase or re-sync) with the in-sync population in order to change the way the template population evolves, which may in turn reduce the fraction of out-of-sync templates in the population and/or counteract the accumulated dephasing of templates. In other words, such flow orderings may at least partially suspend progression of a main population of templates being sequenced and allow at least a portion of the out of phase population to catch up. Likewise, for out of phase sequences that have progressed ahead of the main population such flow orderings may at least partially suspend progression of the out of phase population and allow at least a portion of the main population to catch up. In some embodiments, such flows may be used not to completely remove or alleviate dephasing, but rather as a mechanism to balance or reduce accumulated dephasing effects while at the same time maintaining an efficient or desirable number of flows to achieve a selected/expected throughput (e.g., the flows used to sequence a respective template length). Thus, such flows may result in a reduction and/or correction of CF and/or IE events, improvement in phasic synchrony, increased signal-to-noise ratio, base calling accuracy, and/or overall read length of a sequencing run.

In various embodiments, a phase-protecting reagent flow ordering may be a flow ordering that (1) is not a series of consecutive repeats of a 4-flow permutation of four different reagents (e.g., "ACTG ACTG . . . " or "CAGT CAGT . . . " for example) and (2) is not specifically tailored to a particular combination of a particular template polynucleotide strand to be sequenced and a particular sequencing primer to be used. More specifically, in such embodiments, the flow ordering is not a series of consecutive repeats of any one of the 4!=24 possible 4-flow permutations of four given reagents (e.g., dNTPs or any other relevant reagents for performing sequencing-by-synthesis reactions), is not specifically tailored to a particular template polynucleotide strand to be sequenced, and is not specifically tailored to a particular sequencing primer to be used, so that the phase-protecting reagent flow ordering may have broad applicability to any templates or at least to classes of templates that may share some common properties.

In various embodiments, a phase-protecting reagent flow ordering may be derived from a flow ordering that is a series of consecutive repeats of a 4-flow permutation of four different reagents (e.g., "ACTG ACTG . . . " or "CAGT CAGT . . . " for example) by introducing one or more reagent changes into the sequence (e.g., "AC<u>A</u>G ACTG" or "CA<u>C</u>T CAGT" where one change, shown in boldface and underlining, is made relative to "ACTG ACTG . . . " or "CAGT CAGT . . . "). More generally, 2, 3, 4, 5, 10, 15, 20, or more changes could be made from such consecutive series, and a phase-protecting reagent flow ordering may thus be a substantially non-cyclical, non-repeating pattern of reagents.

In various embodiments, a phase-protecting reagent flow ordering may be "TACT CAGT ATGC AGAC TGCG" (SEQ ID NO: 11), "TACG TACG TACT CAGC TAGC TAGT ATGC ATGC ATGC AGAC TGAC TGAC TGCG" (SEQ ID NO: 12), "TACG TACG TACT CAGC TAGT ATGC ATGC AGAC TGAC TGCG" (SEQ ID NO: 13), "TACG TACG TTAC TCAG CTAA GTAT GCAT GGCA GACT GACC TGCG" (SEQ ID NO: 14), "TACG TACG TCTG AGCA TCGA TCGA TGTA CAGC" (SEQ ID NO: 7), a "TACG TACG TACG TACG TACG TACA TACG CACG TGCG TATG" (SEQ ID NO: 6), "TACG TACG TACG TACG TACG TACAT ACGCA CGTGC GTATG" (SEQ ID NO: 2), and "TACG TACG TAGC TGAC GTAC GTCA TGCA TCGA TCAG CTAG CTGA CGTA GCTA GCAT CGAT CAGT CATG ACTG ACGT AGCT GACT GATC AGTC ATGC ATCG" (SEQ ID NO: 5), for example. Other flow orderings are, of course, possible. (Note: To facilitate readability, lengthy flow orderings may sometimes be listed using groups of flows separated by spaces (e.g., "TACG TACG" rather than "TACGTACG"); however, the presence of the spaces does not have any particular meaning or significance other than to facilitate readability).

In various embodiments, a phase-protecting reagent flow ordering may be derived from a set of k-ary de Bruijn sequences B(k,n), where k denotes a size of an alphabet (e.g., k may be set to 4 for an alphabet comprising the nucleotide species A, C, G, and T), and where n denotes a length of subsequences in the alphabet. The sequence(s) B(k,n) is/are such that every possible subsequence of length n in the alphabet appears exactly once as a sequence of consecutive characters. The de Bruijn approach to flow order determination desirably provides efficient ways to sequence through all four bases while covering potential dimers and generally providing good uncorrelated base flow characteristics. As an example, for an alphabet A={0, 1}, there is a single B(2, 2) sequence, "0011", and there are two distinct B(2, 3) sequences, "00010111" and "11101000," each of which being the reverse and/or negation of the other. More information about de Bruijn sequences and related concepts may be found in Ehrenfest and de Bruijn, CIRCUITS AND TREES IN ORIENTED LINEAR GRAPHS, Simon Stevin, 28:203-217 (1951); de Bruijn, ACKOWLEDGEMENT OF PRIORITY TO C. FLYE SAINTE-MARIE ON THE COUNTING OF CIRCULAR ARRANGEMENTS OF $2^N$ ZEROS AND ONES THAT SHOW EACH N-LETTER WORD EXACTLY ONCE, T.H.-Report 75-WSK-06, Technological University Eindhoven (1975); and Berstel and Perrin, THE ORIGINS OF COMBINATRONICS ON WORDS, European Journal of Combinatronics, 28:996-1022 (2007), which are all incorporated by reference herein in their entirety. In various embodiments, a phase-protecting reagent flow ordering may be a de Bruijn sequence of the nucleotide species A, C, G, and T (an alphabet with four members) where n=2 or where n=3, without any consecutive repeats of the same nucleotide species. In an embodiment, a phase-protecting reagent flow ordering may be an ordering comprising "TACG TCTG AGCA" (SEQ ID NO: 15). In an embodiment, a phase-protecting reagent flow ordering may be a Kautz sequence, which is a de Bruijn sequence that does not have any consecutive repeats of the same character.

In various embodiments, a phase-protecting reagent flow ordering may be derived so as to comprise all possible distinct dimer pairs of four reagents (e.g., nucleotide species A, C, G, and T, where "distinct" with respect to a pair generally refers to the nucleotide species making up the pair being different from each other). For example, the ordering may include the 12 distinct dimer pairs of A, C, G, and T (which are AG, AC, AT, CA, CG, CT, GA, GC, GT, TA, TC, and TG). Although joining each of the 12 distinct dimer pairs together, one after the other, would lead to a 24-flow sequence, constructing a flow sequence containing all 12 distinct pairs does not necessarily require a 24-flow sequence. Shorter flow sequences may be constructed by overlapping at least some of the dimers. For example, the 6-flow sequence AGCATC includes the pairs AG, GC, CA, AT, and TC. In an embodiment, such a flow ordering may be a de Bruijn sequence-based flow ordering that comprises substantially all distinct pairs in 12 bases. For example, the 12-flow sequence "TACG TCTG AGCA" (SEQ ID NO: 15) contains all 12 distinct pairs appearing exactly once (with the AT pair occurring in the wrap-around when the sequence is repeated), and provides the ability to sequence through all four nucleotides while at the same time providing desirable dephasing properties. The 12 distinct pairs may be contained in longer flow sequences. For example, the 32-flow sequence "TACG TACG TCTG AGCA TCGA TCGA TGTA CAGC" (SEQ ID NO: 7) contains each of the 12 distinct dimer pairs. This modification may advantageously be applied in the context of un-terminated sequencing reactions as repeated bases (e.g., homopolymers) will typically not be sequenced in separate sequential flows but rather within the same flow corresponding to the homopolymetric nucleotide.

In various embodiments, a phase-protecting reagent flow ordering may include a flow ordering in which at least one base (e.g., "T") is followed by a different base (e.g., "G", "C", or "A") in at least two different ways in the ordering (e.g., the ordering includes at least two of "TG", "TC", and "TA"). In other words, such a flow ordering may include a flow of N followed immediately by a flow of X, where X and N are variables representing different nucleotide species, while further including, immediately thereafter or elsewhere in the ordering, another flow of N followed immediately by a flow of Y, where Y is a variable representing a nucleotide species different from both X and N. For example, such a flow ordering may contain the following flow sequence: "TG . . . TC . . . TA". In another embodiment, such a flow ordering may include a flow of X followed immediately by a flow of N, where X and N are variables representing different nucleotide species, while further including, immediately thereafter or elsewhere in the ordering, a flow of Y followed immediately by the flow of N, where Y is a variable representing a nucleotide species different from both X and N. For example, such a flow ordering may be "TACG TACG TACG TACG TACG TACG TACG CACGTGCGTATG" (SEQ ID NO: 16) where several cycles of TACG flow orderings are followed by an ordering that includes CG and TG in which the G nucleotide flow is preceded by C and T (note that this ordering also includes AC and GC, GT and AT, and CA and TA, which also follow this pattern).

In various embodiments, a phase-protecting reagent flow ordering may include an ordering in which three of the four nucleotide species A, C, G, and T are flowed at least twice before the fourth nucleotide species is flowed. For example, the flow sequence "TACTACG" repeats each of T, A, and C before the fourth nucleotide species G is flowed. In another example, the flow sequence "TACATACG" repeats T twice, C twice, and A three times before the fourth nucleotide G is flowed. In this approach, the flow ordering starves the template population of the fourth nucleotide species. This starvation of the fourth nucleotide species may result in many or most of the template population awaiting the fourth nucleotide for incorporation, thus giving an opportunity for resynchronization of the template population with the flow of the fourth nucleotide. Other examples of "starvation" flow orderings include (with the starved nucleotides underlined): a 20-flow sequence with a G-starvation, then a C-starvation, and then a T-starvation ("TACTCA<u>G</u>TATG CAGAC<u>T</u>GCG" (SEQ ID NO: 11)); a 40-flow sequence ("TACG TACG TACTCA<u>G</u> CTAGTATG<u>C</u> ATGCAGAC<u>T</u> GACTGCG" (SEQ ID NO: 17)), and a 52-flow sequence ("TACG TACG TACTCA<u>G</u> CTAGC TAGTATG<u>C</u> ATGCAT GCAGAC<u>T</u> GACTGACTGCG" (SEQ ID NO: 12)), for example. Each of the four nucleotide species A, C, G, and T may alternate as the starved nucleotide. For example, the flow sequence "TACATACG" may be used to starve the population of G, followed by the flow sequence "ACGACGT" to starve the population of T, followed by the flow sequence "TAGTAGC" to starve the population of C, and then followed by the flow sequence "CGTCGTA" to starve the population of A. This embodiment in which the template population is starved of each of the four different nucleotides species in turn may be accomplished in any suitable number of flows, including, e.g., a 20-flow sequence (allowing some overlapping of one flow set to another). In an embodiment, such a flow ordering may not include one of each of the four nucleotides in sequential repetition and may include intervening flows where one or more nucleotide flows are delivered multiple times prior to delivery of all four nucleotides in the flow sequence (e.g., such a flow ordering may be "TCTA GACT CGAG" (SEQ ID NO: 18)).

In various embodiments, a phase-protecting reagent flow ordering may include a first set of flows and a second set of flows, with the second set of flows being derived from a remapping of the nucleotide species in the first set of flows. The remapping may involve nucleotides of one particular species in the first set of flows (e.g., all the A's or all the C's) being assigned to a different nucleotide species to generate the flow ordering for the second set of flows. This remapping may involve the reassignment of all or less than all instances of the nucleotide species in the first set of flows. There may be a remapping of two or more of the types of nucleotide species in the first set of flows. Because it is derived from a remapping, such a second set of flows is different from the first set of flows. For example, a first set of flows may be "TACG TCTG AGCA" (SEQ ID NO: 15) and a second set of flows may be created by reassigning nucleotide species as follows: G→A, C→G, and A→C for each instance of the nucleotide species in the first set of flows. By this remapping, the second set of flows becomes "TCGA TGTA CAGC" (SEQ ID NO: 19). In another example, "TACG TACG TCTG AGCA TCGA TCGA TGTA CAGC" (SEQ ID NO: 7) consists of a first set of sixteen flows followed by a second set of sixteen flows, which is generated by the following remapping assignments: G→A, C→G, and A→C. In various embodiments, such flow orderings may contain additional sets of flows based on further remappings. For example, there may be a third set of flows derived from a remapping of the first or second set of flows.

Such embodiments of flow orderings based on flow remapping may be particularly useful when used with flow orderings having resynchronizing properties because the resynchronizing properties are preserved in the second set of flows, but the diversity of the overall flow ordering is increased. For example, if the first set of flows is a de Bruijn sequence having resynchronizing properties, then the second set of flows resulting from a remapping will also be a de Bruijn sequence having resynchronizing properties, but with a different flow order. As a result, repetition of the same flow ordering is reduced and overall diversity of the flow order is increased. Increasing the diversity of the flow ordering may further enhance the resynchronizing properties of the flow ordering. For example, without the additional diversity provided by, e.g., remapping, some fraction of the template population may fall into an out-of-sync phase that is in a stable, offset alignment from the in-sync phase. This stable population of out-of-sync templates may accumulate at offsets that are multiples of the repeating flow ordering cycle. Being in a stable, offset alignment from the in-sync population, this particular out-of-sync population may never have the opportunity to catch up or become synchronized to the in-sync population. But increasing the diversity of the flow ordering, e.g., by remapping, may impede the ability of stable populations of out-of-sync templates to evolve.

According to various embodiments, flow orderings may include one or more of the above-described flow patterns. For example, such a flow ordering may be "TACAT ACGCA CGTGC GTATG" (SEQ ID NO: 20), which has several of the above-described flow patterns. Specifically, this ordering has remapping features: the second 5-flow set is a remapping of the first 5-flow set in which T→A, A→C, and C→G; the third 5-flow set is a remapping of the second 5-flow set with A→C, C→G, and G→T; and the fourth 5-flow set is a remapping of the third 5-flow set with C→G, G→T, and T→A. It also includes subsequences in which a flow of nucleotide species N is followed by a flow of a different nucleotide species X, which is followed by a flow of N again, which is then followed by a flow of Y that is a different nucleotide species from X and N (in particular, the subsequences ACAT, CGCA, GTGC, and TATG follow this pattern). And it also includes a pattern in which the population is starved of the G nucleotide, then starved of the T nucleotide, and then starved of the A nucleotide.

In various embodiments, a phase-protecting reagent flow ordering may be constructed using combinatorial optimization means. For example, one might construct a flow ordering containing all 24 possible 4-flow permutations of nucleotide species A, C, G, and T in succession, with the differences between adjacent permutation 4-flow blocks being minimal in some metric (for example, guaranteeing that no nucleotide species is closer than 3 flows or further than 5 flows away). Such a sample constraint may be achieved by requiring that adjacent permutation blocks differ only by a single transposition of two nucleotide species. Each of the 24 4-flow permutations may be represented by a vertex in a graph, and an edge may be inserted between any two vertices if the corresponding permutations differ by a single transposition. A flow ordering containing these permutation blocks then corresponds to a path in this graph, and a flow ordering containing all 24 permutations exactly once and returning to the starting permutation is then a Hamiltonian path or circuit in this graph. Finding a Hamiltonian circuit, as in this example, allows the construction of a flow order that is highly diverse among permutations, while maintaining good efficiency of extending sequence. The CONTRADANZON flow ordering mentioned herein is an example of an ordering constructed for the most part using such a combinatorial optimization approach (although that particular ordering includes slight modifications allowing use of certain key sequences).

In various embodiments, any phase-protecting reagent flow ordering as described herein may have a minimum length (e.g., in number of flows), which may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, etc., or more generally which may be any positive integer larger than 4. In some embodiments, a flow ordering may be repeated in whole or part to complete a sequencing run and/or attain a desired minimum length.

In various embodiments, flow orderings may include a combination of a plurality of different phase-protecting flow orderings and/or a combination of one or more phase-protecting flow orderings with one or more other flow orderings (e.g., consecutive repeats of a pre-determined permutation of four different reagents) so as to form a longer flow ordering of a desired length and/or to balance properties of different types of flow orderings. Such flow orderings may include a flow of one kind followed by a flow of a different kind, and both flows may have same or different lengths. Such flow orderings may have subsequences of flow orderings that are repeated throughout a run to make up a desired total number of flows. Such a flow ordering may comprise a 20-base flow (e.g., "TACT CAGT ATGC AGAC TGCG" (SEQ ID NO: 11)), for example, which may be repeated one or more times to achieve a desired number of flows, a 40-base flow (e.g., "TACG TACG TACT CAGC TAGT ATGC ATGC AGAC TGAC TGCG" (SEQ ID NO: 13)), or a 52-base flow (e.g., "TACG TACG TACT CAGC TAGC TAGT ATGC ATGC ATGC AGAC TGAC TGAC TGCG" (SEQ ID NO: 12)), for example. Other flow orderings may include flows having a partial cyclical 4-base flow repeated one or more times followed by another flow sequence of a different ordering, such as "TACG TACG TCTGAGCA TCGA TCGA TGTACAGC" (SEQ ID NO: 7), "TACG TACG TACG TACG TACG TACA TACG CACGT-GCGTATG" (SEQ ID NO: 21), and "TACG TACG TACG TACG TACG TACAT ACGCA CGTGC GTATG" (SEQ ID NO: 2), for example. Such mixed flows may help balance efficiency (e.g., in terms of the total number of base flows required to sequence a given length of template) versus the benefit gained (e.g., in terms of correct for or preventing phasing issue). Other flow orderings may include flows that sequentially alternate between two different types of orderings. Other flow orderings may include longer sequence base flows, such as the 96-base flow "TACG TACG TAGC TGAC GTAC GTCA TGCA TCGA TCAG CTAG CTGA CGTA GCTA GCAT CGAT CAGT CATG ACTG ACGT AGCT GACT GATC AGTC ATGC ATCG" (SEQ ID NO: 5), for example. In some embodiments, respective nucleotide flows may have the same duration, relative concentration of nucleotide, and may be followed by an equivalent wash flow. In some embodiments, durations of different nucleotide flows may be different, concentrations of different nucleotide flows may be different, and durations and/or compositions of intervening washes may be different. In some embodiments, the use of phase-protecting flow orderings may be triggered or increased in response to detection of CF and/or IE events (e.g., in real-time, such as when a detected level or frequency of CF and/or IE events has reached a certain threshold). In some embodiments, such a use may be varied according to the position in the sequence read (e.g., use of phase-protecting flow orderings may be triggered or increased after a certain read length of the sequence or may generally be used more frequently at later stages of the sequence read), which may be useful in instances where the CF and/or IE events increase at later stages of the read or in longer reads.

In various embodiments, a phase-protecting reagent flow ordering may be associated or appended to a key sequence, such as TACG. The key sequence may be appended to a de Bruijn sequence, where the key sequence will be expected to demonstrate good signal resolution properties and efficient sequencing while the de Bruijn portion will be expected to provide desirable dephasing properties while sequencing through relatively long portions of a template. Additional details of key sequence usage are described in U.S. Prov. Pat. Appl. No. 61/428,733, filed Dec. 30, 2010, U.S. patent application Ser. No. 13/340,490, filed Dec. 29, 2011, and U.S. Prov. Pat. Appl. No. 61/438,432, filed Feb. 1, 2011, which are all incorporated by reference herein in their entirety.

In various embodiments, a phase-protecting reagent flow ordering may be modified to include one or more contiguous repetitions of the same reagent. For example, a nucleotide species may be flowed twice in immediate succession, e.g., AA, TT, etc. For example, the flow sequence "TACG TACG TTAC TCAG CTAA GTAT GCAT GGCA GACT GACC TGCG" (SEQ ID NO: 14) contains the duplicates TT, AA, GG, and CC (which may be referred to herein as "double-tapped nucleotides"). Although there may be little or no actual incorporation of a nucleotide with an immediate repetition of the same nucleotide flow, the repeated nucleotide flow may be useful for establishing a baseline signal (e.g., noise or background) absent an incorporation event. Further, interposing such repeated nucleotide flows throughout a sequencing run (e.g., every 50 or 100 flows) may further provide the ability to monitor for changes in the reaction conditions (e.g., changes in buffering capacity or baseline, hydrogen ion accumulation, evaluation of "bulk" ion present in solution absent nucleotide incorporation, etc.) over time and to identify sources of systematic error or faults. However, such "double-tapping" orderings may or may not counteract the accumulated dephasing of templates.

It will be appreciated that achieving or improving phasic synchrony desirably enhances the ability to identify nucleotide incorporations and more efficiently and/or accurately sequence templates. Although in many sequencing applications dephasing issues may be relatively small early in the sequencing run, their effects may accumulate as the sequencing progresses and result in degraded sequencing quality for longer templates. In practice, it will be appreciated that the corrective effect of flow orderings described herein will desirably enhance efficiency and/or accuracy of sequencing by helping reduce or eliminate spurious signals associated with out-of-phase templates. Various embodiments of flow orderings described herein may improve the overall quality of a sequencing run by increasing the number of individual reads that achieve a desired sequencing quality, which may be represented as the number of actual or expected errors over a series of bases. For example, error reporting may take the form of a quality scoring metric that indicates the expected number of reads that achieve a desired accuracy or error rate over 50 or 100 base stretches. Flow orderings as described herein may also be used to check or compare system performance and for purposes of evaluating signal processing, base calling, and other algorithms (such as with "double-tapping" flows, for example).

Figure 7A:
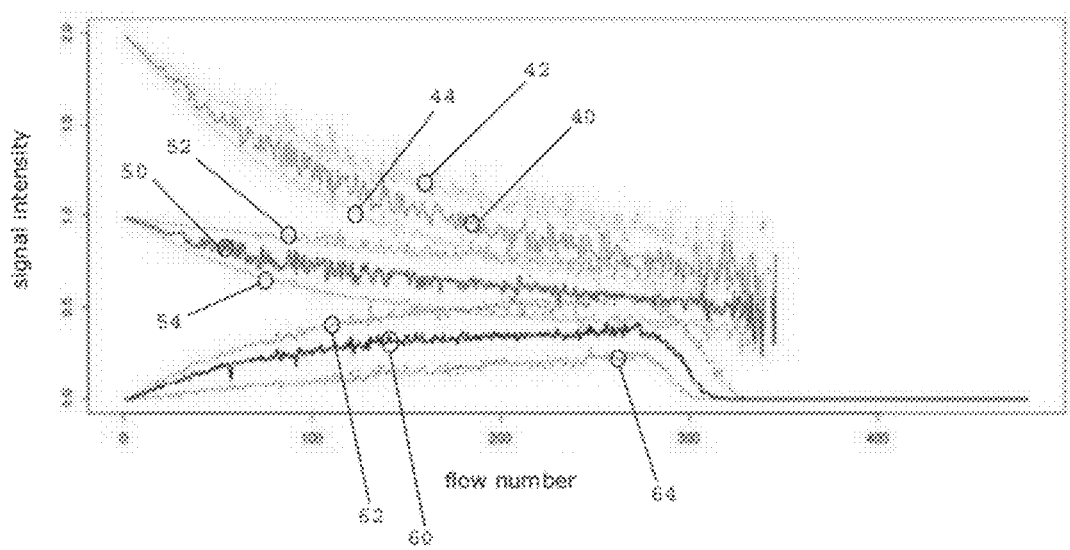
FIG. 7A illustrates exemplary simulation data corresponding to signal response curves for an exemplary cyclical, repeating flow ordering of "GATC GATC . . . ."

FIG. 7A illustrates exemplary simulation data corresponding to signal response curves for an exemplary cyclical, repeating flow ordering of "GATC GATC . . . " It shows signal response curves with signal intensity on the y-axis and the nth flow number (time) on the x-axis, and displays three triplet sets of plot lines, each of the triplet sets having a darker solid line (40, 50, 60) in the middle between two lighter dotted lines (42, 52, 62; 44, 54, 64). The bottom-most triplet set of plot lines (60, 62, 64) show the signal from 0-mer events (non-incorporation); the middle triplet set of plot lines (50, 52, 54) show the signal from 1-mer incorporation events; and the top-most triplet set of plot lines (40, 42, 44) show the signal from 2-mer incorporation events. Within each triplet set, the darker solid line in the middle (40, 50, 60) represents the median signal, the lighter dotted line above (42, 52, 62) represents the 25 percentile signal, and the lighter dotted line below (44, 54, 64) represents the 75 percentile signal. As shown in FIG. 7A, while the signal for the 1-mer and 2-mer incorporation events degrades as the sequencing read progresses, the signal produced by non-incorporation 0-mer events (e.g., the background signal) increases as the sequencing read progresses. Thus, at later portions of the sequencing read, the signal resolution diminishes and it becomes more difficult to distinguish the 0-mer, 1-mer, and 2-mer events from each other. As explained above, the accumulated effects of IE and CF events contribute to this degradation of signal quality.

Figure 7B:
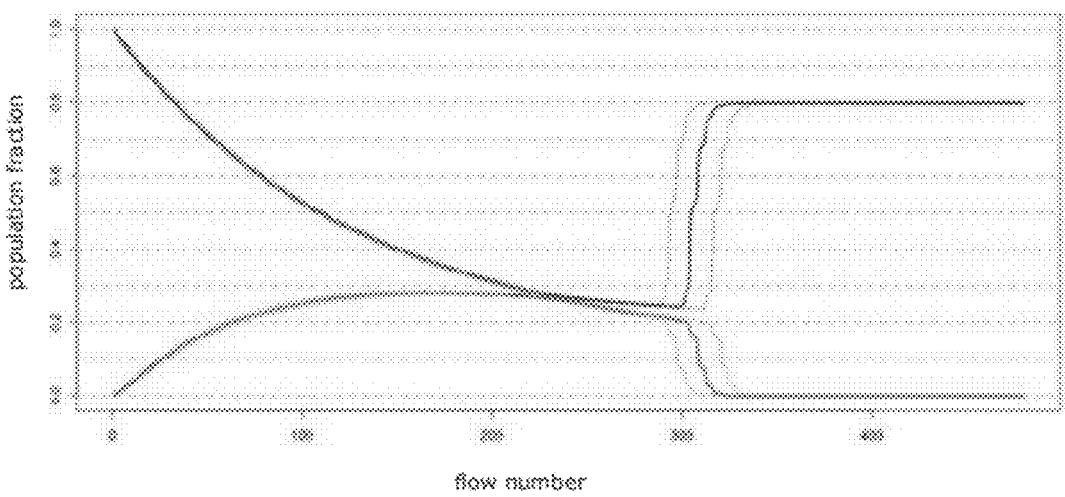
FIG. 7B illustrates exemplary simulation data corresponding to template population evolution as sequencing progresses for the cyclical, repeating flow ordering of FIG. 7A.

FIG. 7B illustrates exemplary simulation data corresponding to template population evolution as sequencing progresses for the cyclical, repeating flow ordering of FIG. 7A. The y-axis represents the population fraction, with the upper plot line representing the largest population (in-sync) and the lower plot line representing the second largest population (out-of-sync). As shown in FIG. 7B, the relative number of in-sync templates decreases while the relative number of out-of-sync templates increases with progression of the sequencing read due to the loss of phase synchrony.

Figure 8A:
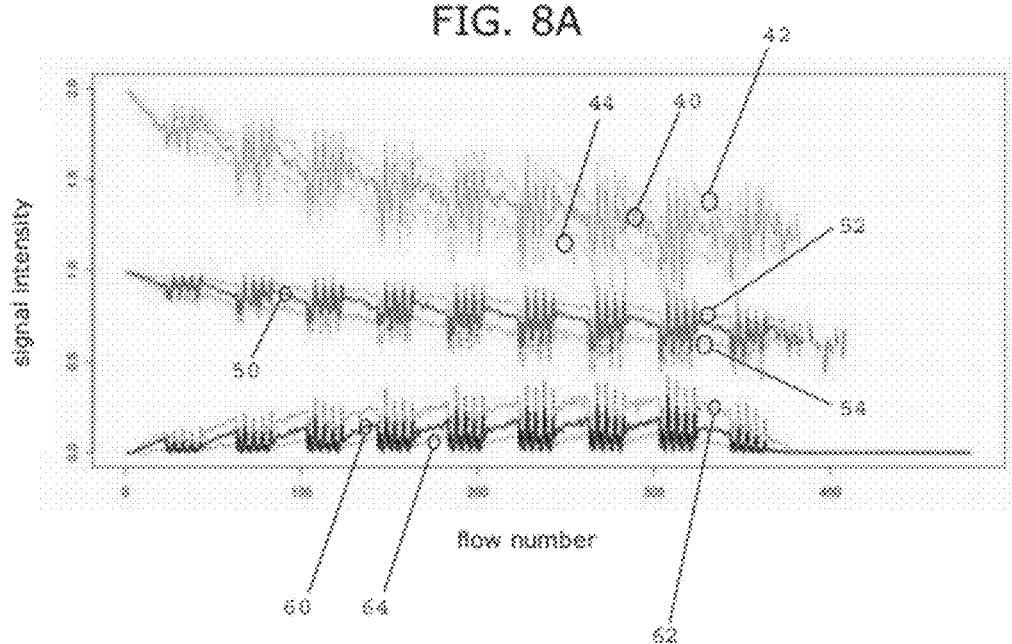
FIG. 8A illustrates exemplary simulation data corresponding to signal response curves for an exemplary flow ordering of "TACG TACG TACG TACG TACG TACAT ACGCA CGTGC GTATG" (SEQ ID NO: 2).
Figure 8B:
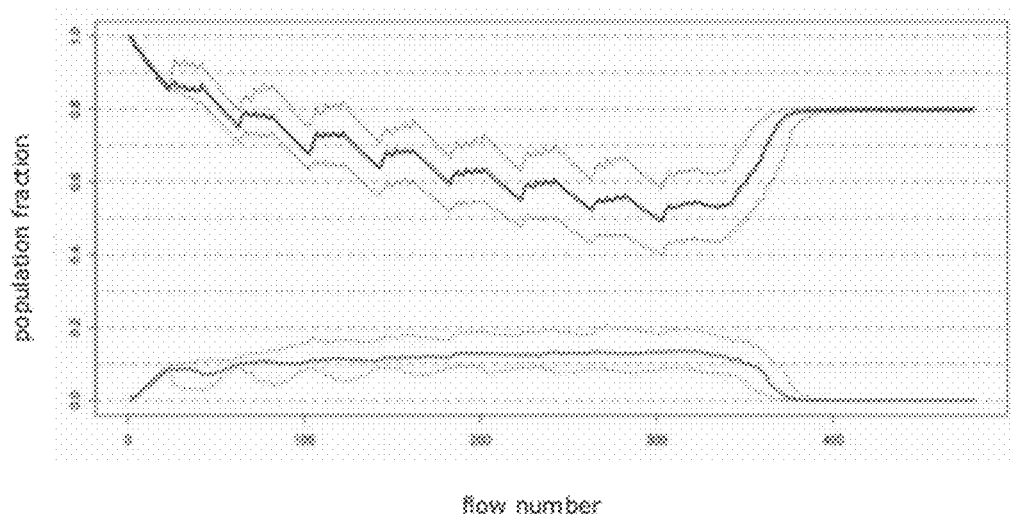
FIG. 8B illustrates exemplary simulation data corresponding to template population evolution as sequencing progresses for the flow ordering of FIG. 8A.
Figure 9A:
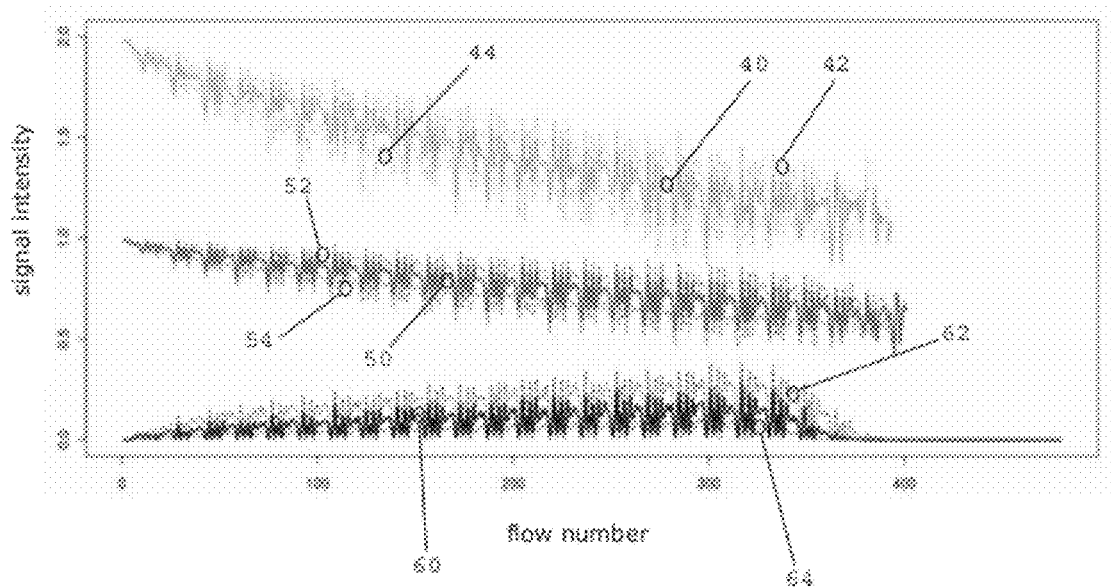
FIG. 9A illustrates exemplary simulation data corresponding to signal response curves for an exemplary flow ordering of "TACG TACG TCTG AGCA" (SEQ ID NO: 3).
Figure 9B:
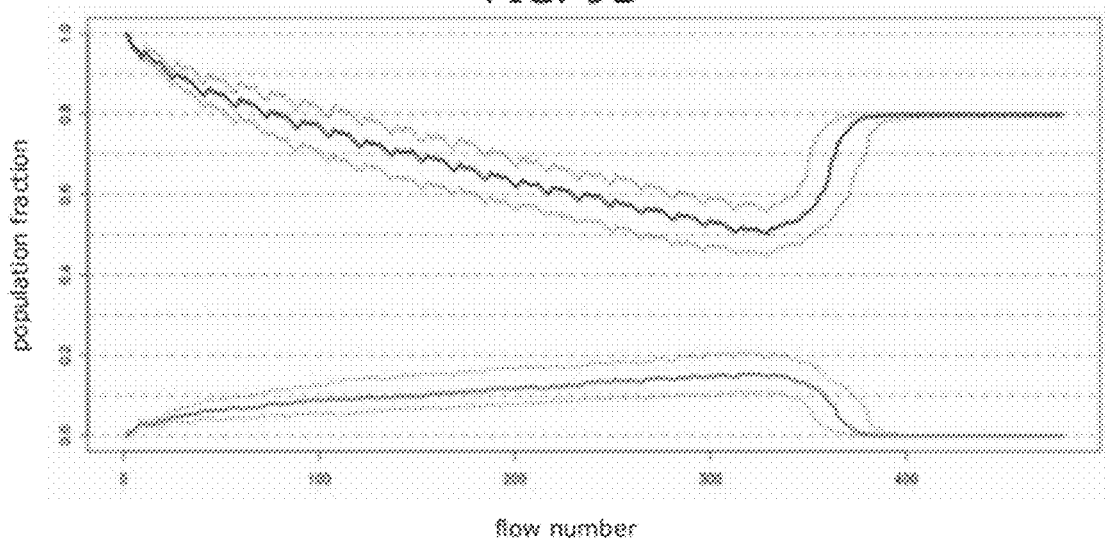
FIG. 9B illustrates exemplary simulation data corresponding to template population evolution as sequencing progresses for the flow ordering of FIG. 9A.

FIGS. 8A and 8B illustrate exemplary simulation data of the same type as in FIGS. 7A and 7B, but corresponding to signal response curves for an exemplary phase-protecting flow ordering of "TACG TACG TACG TACG TACG TACAT ACGCA CGTGC GTATG" (SEQ ID NO: 2). Similarly, FIGS. 9A and 9B illustrate exemplary simulation data of the same type as in FIGS. 7A and 7B, but corresponding to signal response curves for an exemplary phase-protecting flow ordering of "TACG TACG TCTG AGCA" (SEQ ID NO: 3). FIGS. 8A and 9A show that using the phase-protecting flow orderings improves signal resolution/separation and maintains signal intensities in the main population over a greater number of flows, when compared to the flow ordering of FIG. 7A. In turn, FIGS. 8B and 9B show that the phase-protecting flow orderings slow the rate at which the out-of-phase population accumulates, when compared to the flow ordering of FIG. 7B. In other words, the phase-protecting flow orderings help prevent the more rapid convergence of the main population and the two lesser populations associated with an increase in the out of phase population due to accumulated effects of unmitigated IE and/or CF related errors, and help provide better signal separation between the different populations over time/flows and maintain a greater proportion of the main population (in phase) with greater signal intensity over time/flows.

Figure 10A:
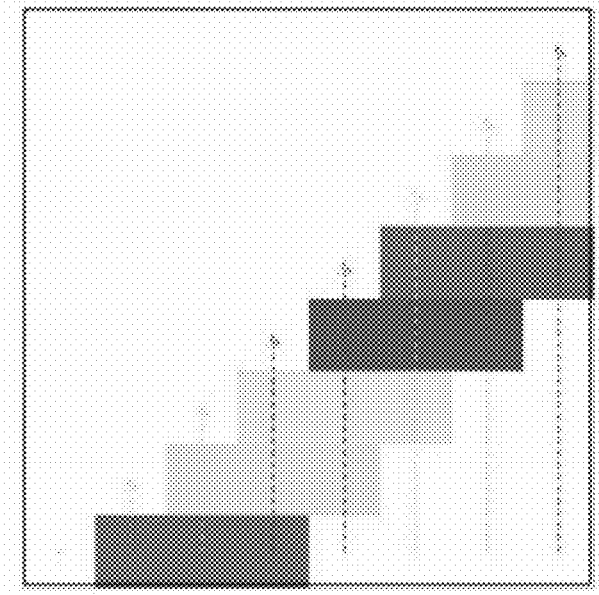
FIG. 10A illustrates an exemplary adjacency matrix representation for an exemplary cyclical, repeating flow ordering of "TACG TACG . . . ."

FIG. 10A illustrates an exemplary adjacency matrix representation for the cyclical, repeating flow ordering of "TACG TACG . . . " The matrix has eight row and eight columns, corresponding to two cycles of TACG. Each row represents the possible flows where a base may incorporate after the flow corresponding to a row. For example, the first row corresponds to the first T in the flow order, and the three colored cells indicate the possible flows (ACG) where a sequence incorporating in flow one may continue. The second row corresponds to the second flow "A", and the colored blocks correspond to flows that may incorporate immediately after incorporating an A in flow 2. Each column represents a flow where a growing sequence may continue to incorporate bases. There are four colors (red, green, blue, and purple) or shades of grey, and each represents the base corresponding to each row (the base a growing sequence just incorporated a homopolymer run). Each vertical arrow represents the possible incorporation of a base at the corresponding flow, which would then be directed to the row where building a sequence may continue. For example, the first vertical arrow in column two represents the fact that if a base were incorporated at the second flow, an "A", the possible flows where the next base may incorporate are in the second row; the second vertical arrow in column three represents the fact that if a base were incorporated at the third flow, a "C", the possible next flows where an incorporation may happen are the colored blocks in the third row; etc. In this way, the color or shade or grey of a block corresponds to the nucleotide previously incorporated in a growing sequence, and the columns of the colored blocks indicate potential other flows where a sequence may continue. Uncolored blocks are impossible to reach as the successor of an incorporation—for example, the fifth flow, a "T", may not be the first base (first row) incorporating after the first "T" flow. The properties of an adjacency matrix are connected with the efficiency and phase-correcting properties of a flow ordering. In an embodiment, such a matrix representation may be used to illustrate the efficiency and phase-correcting properties (or lack thereof) of a flow ordering. In particular, good efficiency and phase-correcting properties may be associated with the presence of at least one color or shade or gray (or corresponding base type) that is repeated in one or more columns of the matrix. Flow orderings possessing this property may recombine out-of-phase molecules (although not all such flow orderings necessarily will recombine out-of-phase molecules). FIG. 10A does not exhibit this property (as every column has at most three bases that are distinct).

Figure 10B:
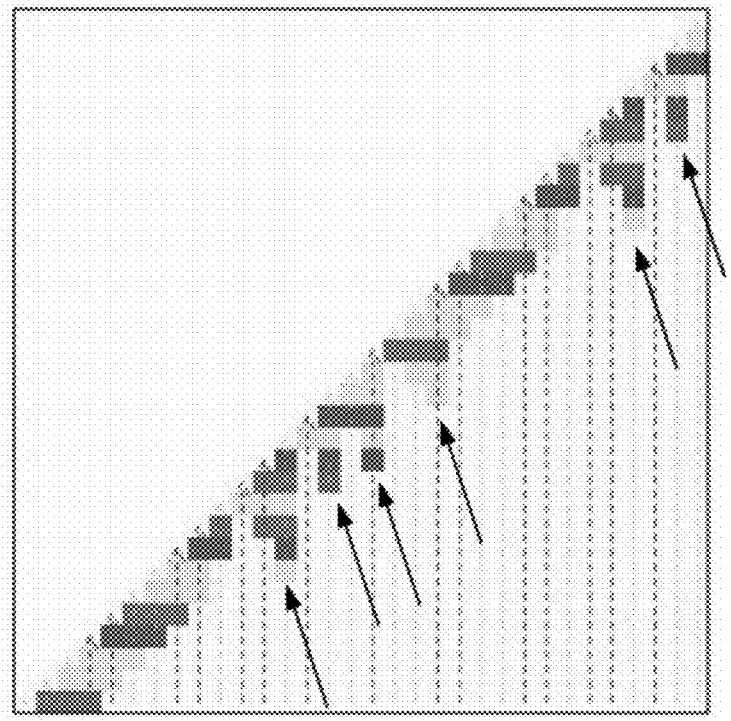
FIG. 10B illustrates an exemplary adjacency matrix representation for the flow ordering of FIG. 9A.

FIG. 10B illustrates an exemplary adjacency matrix representation for the flow ordering of FIG. 9A. The matrix has thirty-two rows and thirty-two columns, corresponding to two repetitions of flow ordering "TACG TACG TCTG AGCA" (SEQ ID NO: 3). It shows six columns with repeats (see arrows) at a relatively high frequency and separated by relatively small gaps. For example, column 13 shows that there are two different ways of reaching this flow (an "A") from a previous incorporation containing each of the other three bases; column 15 shows that there are two different ways of reaching this flow (a "C") from previous "G" flows; etc. If there is a sequence with prefix ending in "GC", two populations of molecules that are out of phase—one incorporating the "G" in one flow, one incorporating the "G" in the other, may become in phase at the "C" flow, because both previous "G" flows have this "C" flow as the successor. The corresponding flow ordering is thus likely to have good efficiency and phase-correcting properties.

Figure 10C:
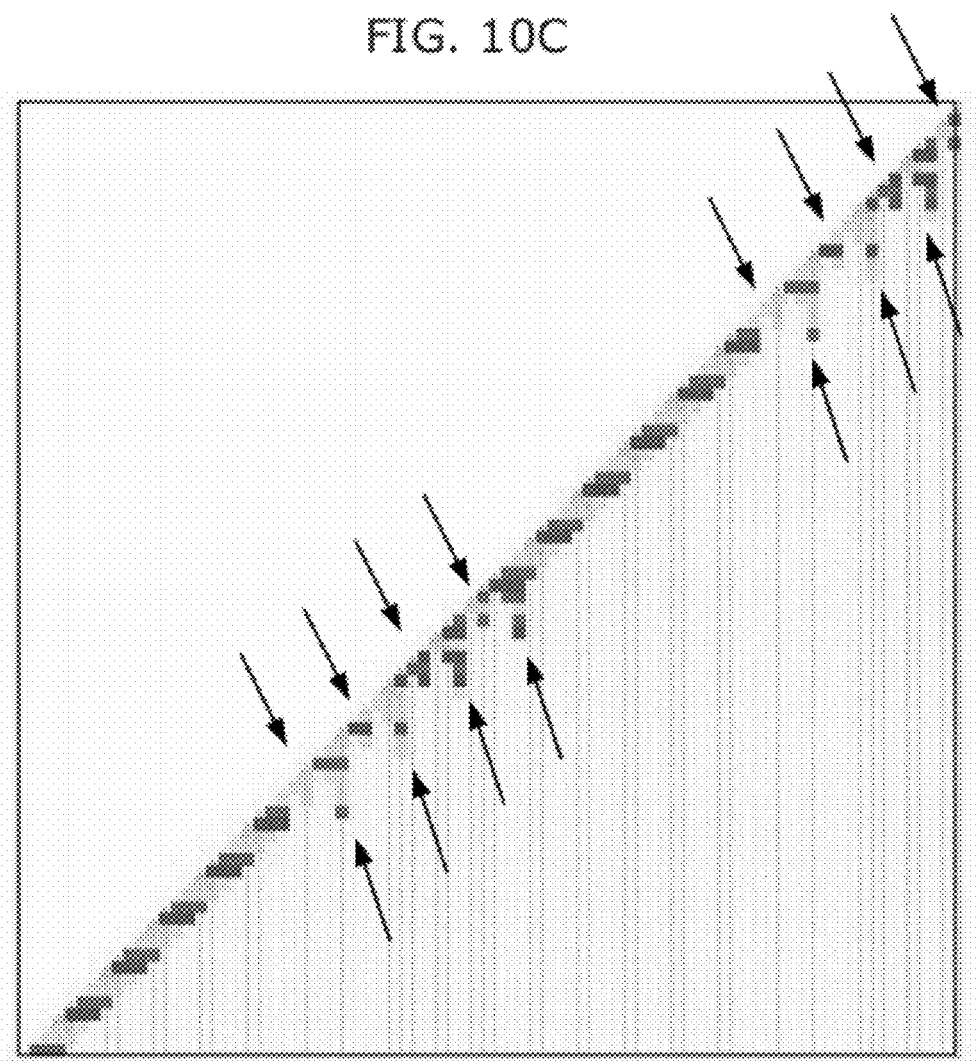
FIG. 10C illustrates an exemplary adjacency matrix representation for the flow ordering of FIG. 8A.

FIG. 10C illustrates an exemplary adjacency matrix representation for the flow ordering of FIG. 8A. The matrix has eighty rows and eighty columns, corresponding to two repetitions of flow ordering "TACG TACG TACG TACG TACG TACAT ACGCA CGTGC GTATG" (SEQ ID NO: 2). It shows eight columns with repeats (see arrows) arranged in two groups separated by a gap of 20 bases. For example, column 25 shows that there are multiple ways of incorporating a base in this flow, no matter what previous base incorporated; column 28 shows that there are two ways of getting to this flow from an "A", etc. The corresponding flow ordering is thus also likely to have good efficiency and phase-correcting properties.

In various embodiments, there are provided methods for evaluating and/or ranking flow orderings (e.g., phase-protecting flow orderings) to identify most suitable ones. In an embodiment, flow orderings may be evaluated and/or ranked based on trade-offs between various characteristics. Two examples of useful characteristics for this purpose are the extension efficiency (that is, some assessment of how rapidly a sequence can be extended by a homopolymer) and the dephasing merit (that is, some estimate of the ability of a particular flow ordering to minimize the effects of phasing issues on sequencing). The extension efficiency may be relatively easy to assess. For example, it could be determined according to the expected number of homopolymers extended in a sequence after performing a given number of flows. For example, if the expected number of homopolymers were 50 at flow 100, the efficiency could be set to 0.5. Various other linear and non-linear approaches could also be used to assign efficiency to extension. A higher efficiency essentially signifies that sequencing may be performed faster and at lower cost. In turn, the dephasing merit may be estimated by looking at the realized separation between signals for a known 1-mer in a flow and signals for a known 0-mer in the flow (which would of course be occurring in different sequences). If these signals are reliably distinct, the potential to reconstruct the sequence may be deemed high. If the distributions for 1-mers and 0-mers overlap, however, the potential to reconstruct the sequence may be deemed low. One way of summarizing this relationship between distributions is to look at the difference in median signal for each distribution, scaled by some measure of the variation (e.g., the interquartile range). This provides a picture of the dephasing effect in a given flow. (Note: to prevent instability when the population interquartile range is very small, a small stabilizing noise estimate of 0.1 may be added, which was done in the plotted figures). Because this measure can be variable per flow, and because the same flow may correspond to different expected sequence lengths given the different efficiencies of extension, it may be advantageous to measure merit over many flows and over flows corresponding to a range of expected sequence lengths. Finally, in various embodiments, because these quantities/characteristics may be difficult to obtain analytically, they may be assessed or examined by simulation to evaluate what flow orders are likely to be most effective.

In various embodiments, phase-protecting reagent flow orderings may be simulated using various models related to IE and/or CF events. For example, such simulations may include one or more aspects described in U.S. patent application Ser. No. 13/283,320, filed Oct. 27, 2011, based on U.S. Prov. Pat. Appl. No. 61/407,377, filed Oct. 27, 2010, which are all incorporated by reference herein in their entirety.

Figure 11:
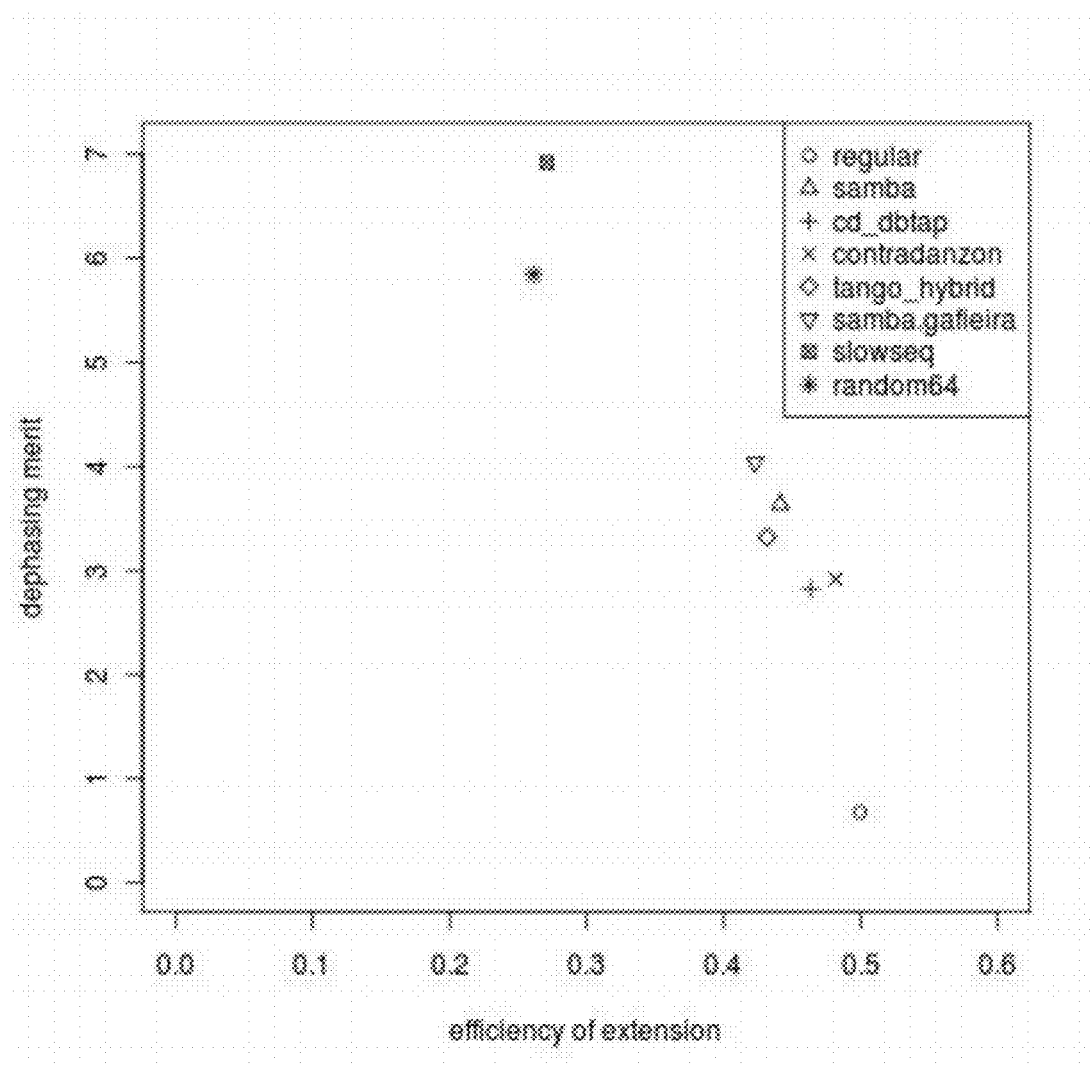
FIG. 11 illustrates an exemplary graph showing trade-offs between efficiency of extension and dephasing merit for eight exemplary flow orderings.

FIG. 11 illustrates an exemplary graph showing trade-offs between efficiency of extension and dephasing merit for eight exemplary flow orderings. It shows simulated performance for eight particular flow orderings (referred to as REGULAR, SAMBA, CD_DBTAP, CONTRADANZON, TANGO_HYBRID, SAMBA.GAFIEIRA, SLOWSEQ, and RANDOM64 herein) used against 500 random sequences of length 300 drawn from a uniform distribution of the four bases. In all cases, the flow orderings are evaluated over a span of 960 flows. The efficiency of extension over the first half of the sequence is evaluated by fitting a linear model and the dephasing merit is computed over flows corresponding to 150 to 200 homopolymer extensions. The SAMBA flow represents a particularly good compromise between dephasing effectiveness and efficiency of extension. Other relatively similar flows are SAMBA.GAFIEIRA, TANGO_HYBRID, CD_DBTAP, and CONTRADANZON. A randomly chosen sequence (RANDOM64) shows that a high degree of randomness is associated with excellent phase-protection (albeit at the cost of relatively low efficiency of extension). A sequence deliberately designed to increase dephasing at the expense of extension efficiency (SLOWSEQ), shows a very high degree of phase-protection. Although a sequence deliberately designed to achieve a high dephasing merit can outperform randomly chosen sequences for a given extension efficiency, generally one must trade off one quality for the other and an analysis of these the dephasing merit and efficiency of extension characteristics provides a useful approach to evaluate and/or rank flow orderings for their suitability. In various embodiments, in order to ensure optimal applicability of phase-protecting flow orderings in as many contexts and applications as possible, the evaluation and/or ranking of flow orderings may be based on a plurality of arbitrary or random test sequences and, in particular, the evaluation and/or ranking of flow orderings may be not tailored to any particular sequence to be sequenced and/or primer to be used in such sequencing.

In various embodiments, the dephasing merit and efficiency of extension characteristics may not be the only criteria, and other desirable properties for flow orderings may be considered. For example, double-tapping flows have the added benefit of allowing direct estimation of buffering in a given flow, as they provide a snapshot of the system without a significant amount of incorporation. In another example, for effective variant detection, it may be desired to maximize flow space diversity, which may be helpful when comparing multiple reads. In other examples, balancing usage of the nucleotide tubes and minimizing the time since a previous flow of a nucleotide can be helpful properties (in this regard, CONTRADANZON, for example, has no repeated nucleotides occurring more than five flows apart). Finally, in other examples specific applications and underlying biologic principles pertaining to certain classes of sequences may be taken into consideration (e.g., organisms with unusual GC content or enzymes with differing behaviors may benefit from use of flow orderings with different likelihoods of sequences for the simulation, which may be factored in this flow ordering selection analysis) although at the cost of some loss in optimally broad applicability. In various embodiments, phase-protecting reagent flow orderings may be selected to have as high a diversity of flows as possible. In various embodiments, phase-protecting reagent flow orderings may be selected to have as low an auto-correlation as possible.

FIG. 12A illustrates exemplary simulation data corresponding to signal response curves for an exemplary cyclical, repeating flow ordering of "TACG TACG . . . " FIG. 12B illustrates exemplary simulation data corresponding to template population evolution as sequencing progresses for the cyclical, repeating flow ordering of FIG. 12A. Except for the change in flow ordering, the curves and plots in FIGS. 12A and 12B are of the same type as in FIGS. 7A and 7B. FIG. 12A shows that while the signal for the 1-mer and 2-mer incorporation events degrades as the sequencing read progresses, the signal produced by non-incorporation 0-mer events (e.g., the background signal) increases as the sequencing read progresses. Thus, at later portions of the sequencing read, the signal resolution diminishes and it becomes more difficult to distinguish the 0-mer, 1-mer, and 2-mer events from each other. FIG. 12B shows that the relative number of in-sync templates decreases while the relative number of out-of-sync templates increases with progression of the sequencing read due to the loss of phase synchrony.

Figures 13A, 13B:
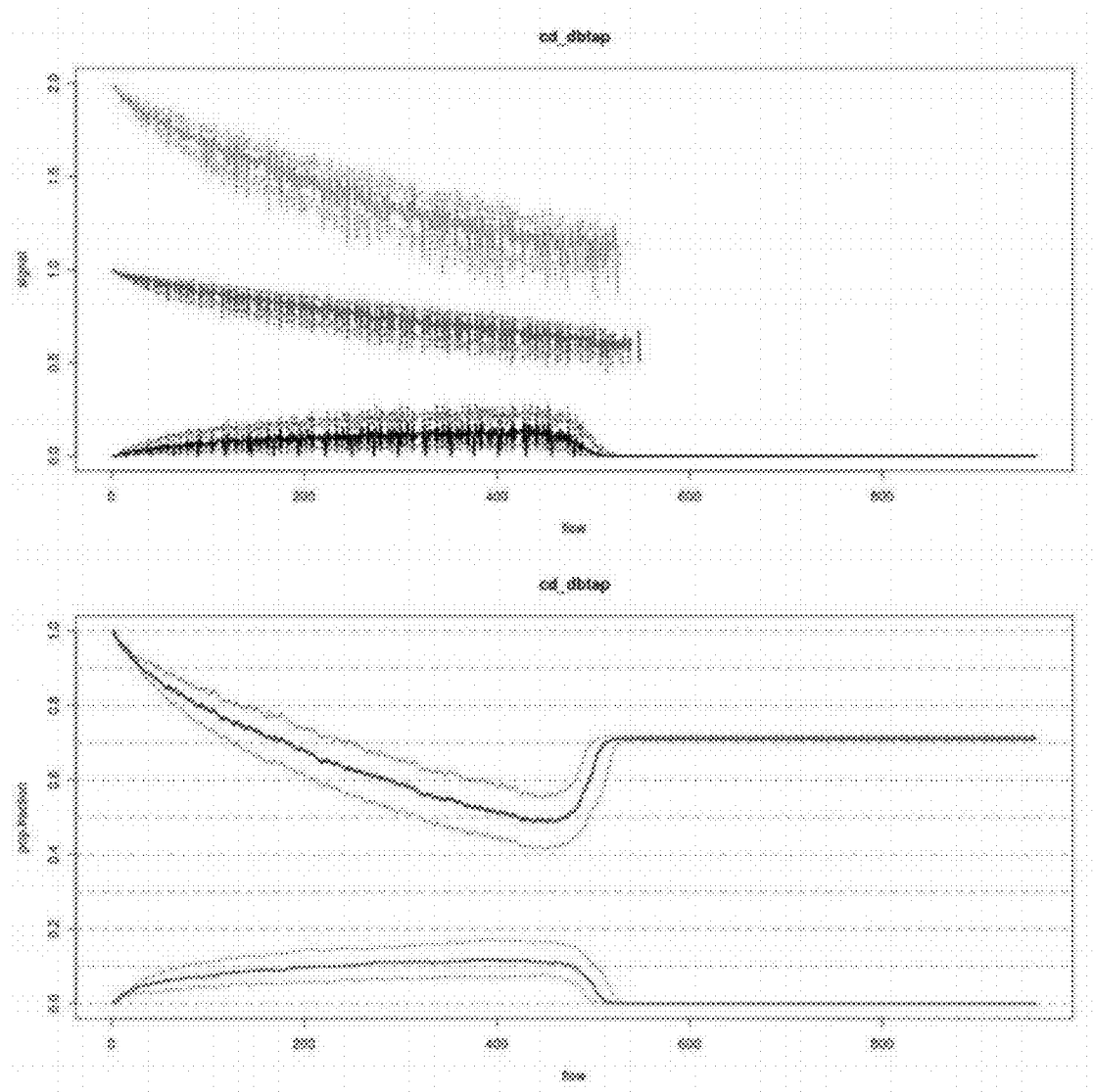
FIG. 13A illustrates exemplary simulation data corresponding to signal response curves for an exemplary flow ordering of "TACG TACG TAGC TTGA CGTA CGTC ATGC ATCG ATCA GCTA AGCT GACG TAGC TAGC ATCG ATCC AGTC ATGA CTGA CGTA GCTG ACTG GATC AGTC ATGC ATCG" (SEQ ID NO: 4).
FIG. 13B illustrates exemplary simulation data corresponding to template population evolution as sequencing progresses for the flow ordering of FIG. 13A.
Figures 14A, 14B:
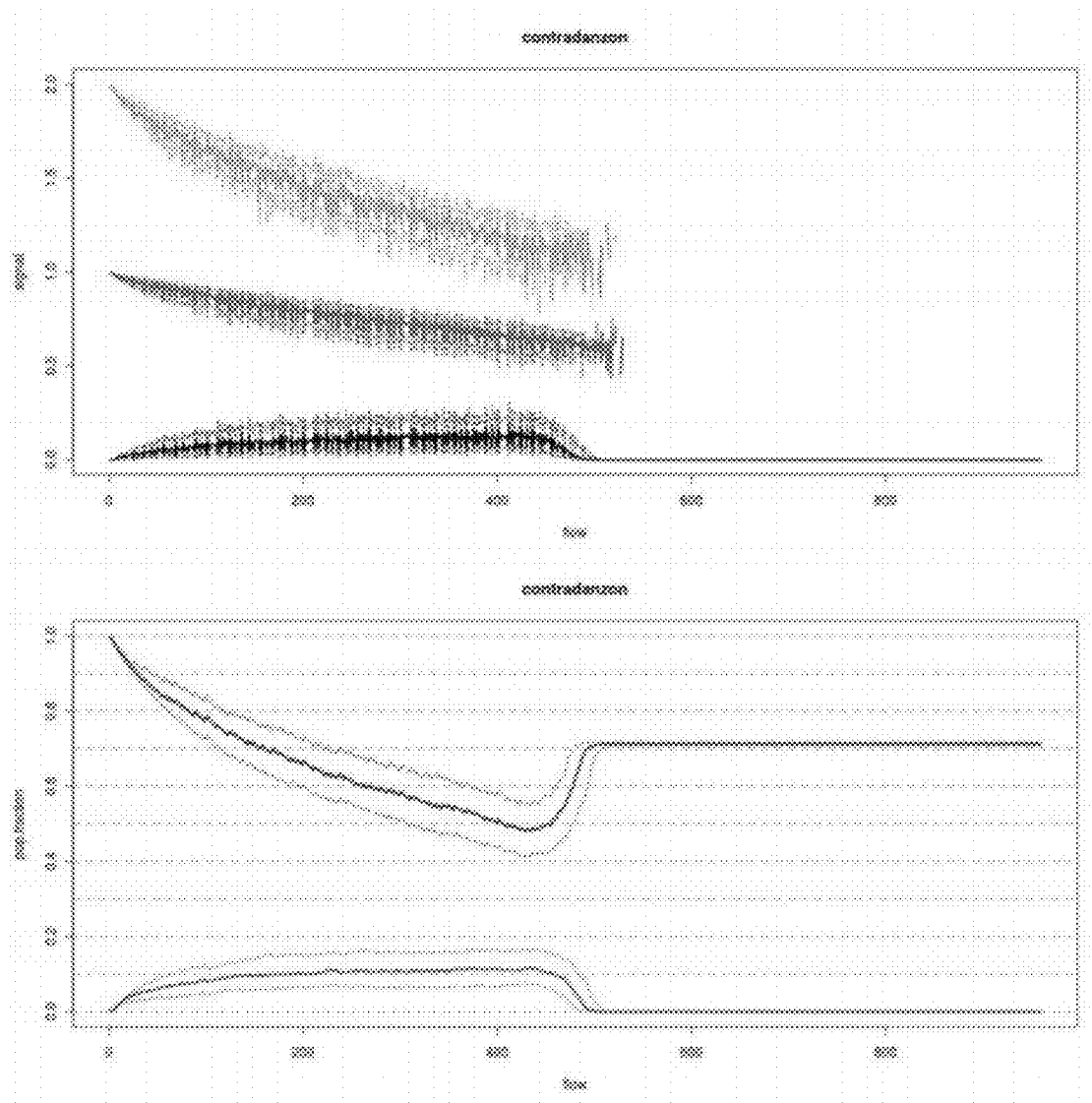
FIG. 14A illustrates exemplary simulation data corresponding to signal response curves for an exemplary flow ordering of "TACG TACG TAGC TGAC GTAC GTCA TGCA TCGA TCAG CTAG CTGA CGTA GCTA GCAT CGAT CAGT CATG ACTG ACGT AGCT GACT GATC AGTC ATGC ATCG" (SEQ ID NO: 5).
FIG. 14B illustrates exemplary simulation data corresponding to template population evolution as sequencing progresses for the flow ordering of FIG. 14A.
Figures 15A, 15B:
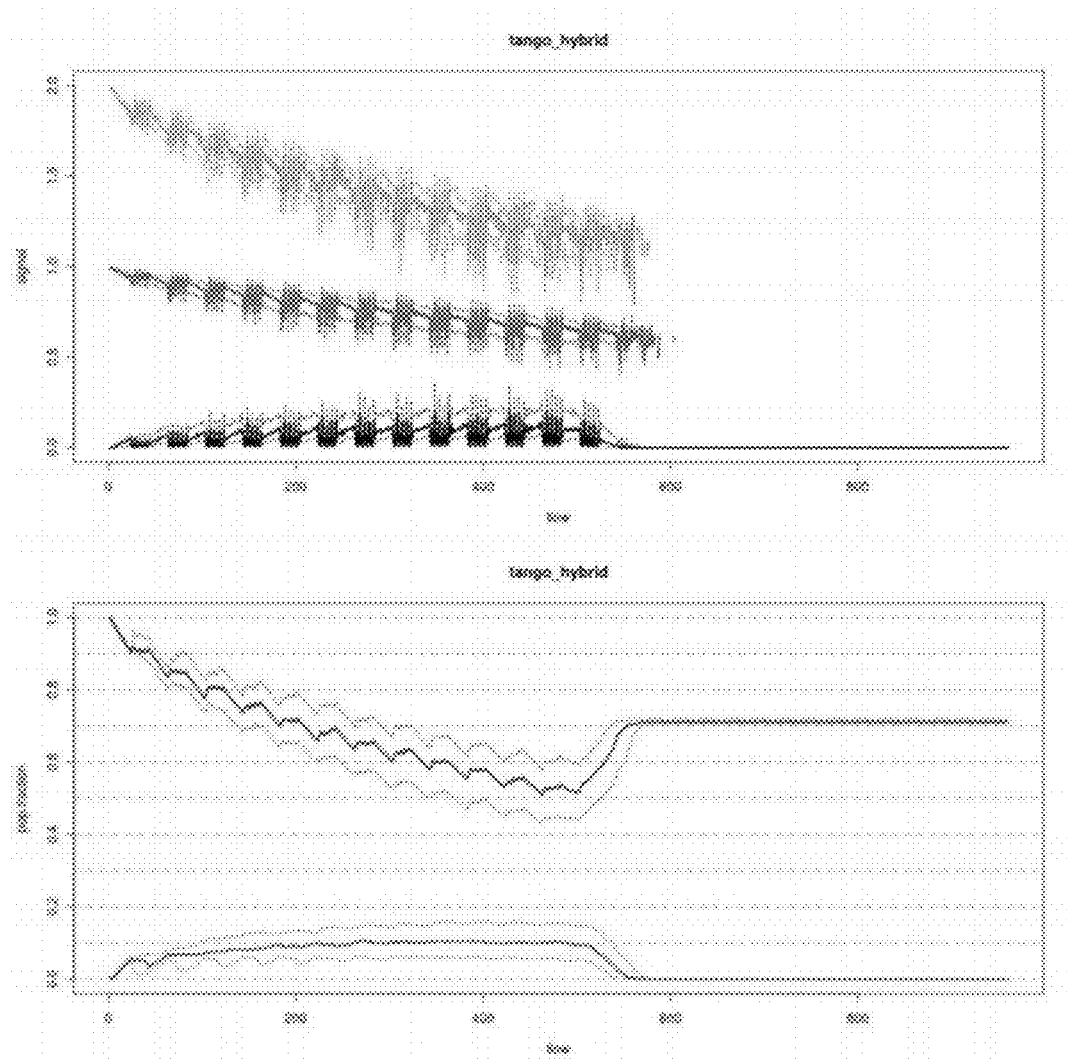
FIG. 15A illustrates exemplary simulation data corresponding to signal response curves for an exemplary flow ordering of "TACG TACG TACG TACG TACG TACA TACG CACG TGCG TATG" (SEQ ID NO: 6).
FIG. 15B illustrates exemplary simulation data corresponding to template population evolution as sequencing progresses for the flow ordering of FIG. 15A.

FIG. 13A illustrates exemplary simulation data corresponding to signal response curves for an exemplary flow ordering of "TACG TACG TAGC TTGA CGTA CGTC ATGC ATCG ATCA GCTA AGCT GACG TAGC TAGC ATCG ATCC AGTC ATGA CTGA CGTA GCTG ACTG GATC AGTC ATGC ATCG" (SEQ ID NO: 4) (CD_D-BTAP). FIG. 13B illustrates exemplary simulation data corresponding to template population evolution as sequencing progresses for the flow ordering of FIG. 13A. FIG. 14A illustrates exemplary simulation data corresponding to signal response curves for an exemplary flow ordering of "TACG TACG TAGC TGAC GTAC GTCA TGCA TCGA TCAG CTAG CTGA CGTA GCTA GCAT CGAT CAGT CATG ACTG ACGT AGCT GACT GATC AGTC ATGC ATCG" (SEQ ID NO: 5) (CONTRADANZON). FIG. 14B illustrates exemplary simulation data corresponding to template population evolution as sequencing progresses for the flow ordering of FIG. 14A. FIG. 15A illustrates exemplary simulation data corresponding to signal response curves for an exemplary flow ordering of "TACG TACG TACG TACG TACG TACA TACG CACG TGCG TATG" (SEQ ID NO: 6) (TANGO_HYBRID). FIG. 15B illustrates exemplary simulation data corresponding to template population evolution as sequencing progresses for the flow ordering of FIG. 15A. FIG. 16A illustrates exemplary simulation data corresponding to signal response curves for an exemplary flow ordering of "TACG TACG TCTG AGCA TCGA TCGA TGTA CAGC" (SEQ ID NO: 7) (SAMBA). FIG. 16B illustrates exemplary simulation data corresponding to template population evolution as sequencing progresses for the flow ordering of FIG. 16A. FIG. 17A illustrates exemplary simulation data corresponding to signal response curves for an exemplary flow ordering of "TACG TACG TCTG AGCA TCGA TCGA TGTA CAGC TGAC TGAC TATC GCAG AGCT AGCT ACAT GTCG ACTG ACTG ATAG CGTC ATGC ATGC AGAC TCGT CGTA CGTA CTCA GATG CTAG CTAG CACG TGAT CAGT CAGT CGCT ATGA GTCA GTCA GCGA TACT GCAT GCAT GAGT CTAC GATC GATC GTGC ACTA" (SEQ ID NO: 8) (SAMBA.GAFIEIRA). FIG. 17B illustrates exemplary simulation data corresponding to template population evolution as sequencing progresses for the flow ordering of FIG. 17A. FIG. 18A illustrates exemplary simulation data corresponding to signal response curves for an exemplary random flow ordering of "CTTG CTTA CAAC TCTC ATAT CGGT ATCC TGTG GAAA CTCC GTTA TCAG CATC CTCT CATG TTAG" (SEQ ID NO: 9) (RANDOM64). FIG. 18B illustrates exemplary simulation data corresponding to template population evolution as sequencing progresses for the random flow ordering of FIG. 18A. FIG. 19A illustrates exemplary simulation data corresponding to signal response curves for an exemplary flow ordering of "TACA CTCT AGTA TAGA GTCG TGTC TCGA CGCG AGAC" (SEQ ID NO: 10) (SLOWSEQ). FIG. 19B illustrates exemplary simulation data corresponding to template population evolution as sequencing progresses for the flow ordering of FIG. 19A. Except for the change in flow ordering, the curves and plots in FIGS. 13A-19B are of the same type as in FIGS. 7A and 7B. These figures, when considered in comparison with the cyclical, repeating flow ordering of FIGS. 12A and 12B, show how phase-protecting flow orderings facilitate signal resolution/separation and help enhance accuracy of sequencing, especially with increasing numbers of flows.

In various embodiments, phase-protecting flow orderings may be used in the context of paired-end sequencing. For example, a template sequence might be sequenced twice, e.g., once in the forward direction and once in the reverse, and may undergo incorporation for certain flows in the flow order in the forward direction (e.g., base 13 and base 14 might undergo incorporation in flows 25 and 26). In such a case, it may be impossible for a different base to be inserted between these two flows, which may provide strong evidence that there is no such insertion in the sequence. In the reverse direction, these two bases may be in flows that are separated (e.g., say in flows 175 and 179), in which case the reverse read may be reconstructed to have an insertion between those two flows. The forward read can correct such an error, however, because it eliminates certain classes of errors. It is therefore advantageous to have the maximum number of opportunities where the successive flows incorporating in the forward sequencing pass and the successive flows incorporating in the reverse sequencing pass are different. Because the sequence cannot be known ahead of time, it is advantageous to select a flow ordering that maximizes the diversity of flows between a sequence and the reverse complement of a sequence. One way of doing this is to engineer a flow ordering having many locally diverse patches, such as the SAMBA.GAFIEIRA flow ordering, for example, to make it unlikely that a sequence being read in the forward and reverse directions will encounter similar succeeding flows.

Figure 20:
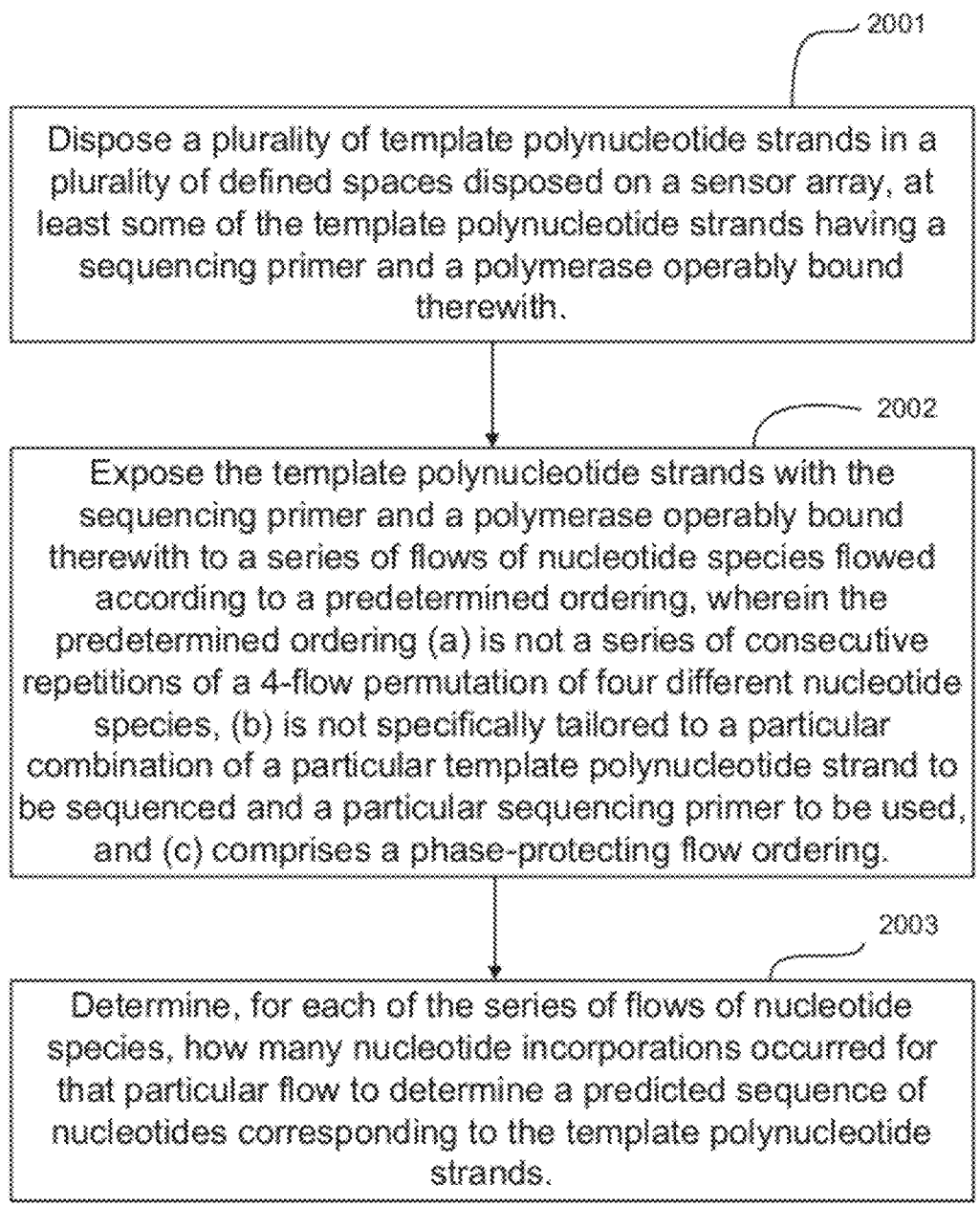
FIG. 20 illustrates an exemplary method for sequencing a nucleic acid using phase-protecting flows.

FIG. 20 illustrates an exemplary method for sequencing a nucleic acid using phase-protecting flows according to an embodiment. In step 2001, a plurality of template polynucleotide strands are disposed in a plurality of defined spaces disposed on a sensor array, at least some of the template polynucleotide strands having a sequencing primer and a polymerase operably bound therewith. In step 2002, the template polynucleotide strands with the sequencing primer and a polymerase operably bound therewith are exposed to a series of flows of nucleotide species flowed according to a predetermined ordering, wherein the predetermined ordering (a) is not a series of consecutive repetitions of a 4-flow permutation of four different nucleotide species, (b) is not specifically tailored to a particular combination of a particular template polynucleotide strand to be sequenced and a particular sequencing primer to be used, and (c) comprises a phase-protecting flow ordering. In step 2003, it is determined, for each of the series of flows of nucleotide species, how many nucleotide incorporations occurred for that particular flow to determine a predicted sequence of nucleotides corresponding to the template polynucleotide strands.

Figure 21:
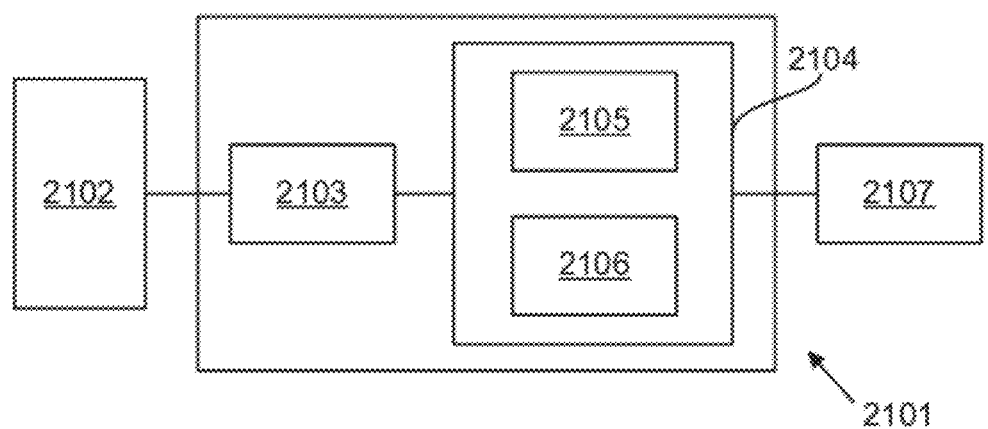
FIG. 21 illustrates an exemplary system for nucleic acid sequencing.

FIG. 21 illustrates a system 2101 for nucleic acid sequencing according to an exemplary embodiment. The system includes a reactor array 2102; a reader board 2103; a computer and/or server 2104, which includes a CPU 2105 and a memory 2106; and a display 2107, which may be internal and/or external. One or more of these components may be used to perform or implement one or more aspects of the exemplary embodiments described herein.

According to an embodiment, there is provided a method for nucleic acid sequencing, comprising: (1) disposing a plurality of template polynucleotide strands in a plurality of defined spaces disposed on a sensor array, at least some of the template polynucleotide strands having a sequencing primer and a polymerase operably bound therewith; (2) exposing the template polynucleotide strands with the sequencing primer and a polymerase operably bound therewith to a series of flows of nucleotide species flowed according to a predetermined ordering; and (3) determining, for each of the series of flows of nucleotide species, how many nucleotide incorporations occurred for that particular flow to determine a predicted sequence of nucleotides corresponding to the template polynucleotide strands, wherein the predetermined ordering (a) is not a series of consecutive repetitions of a 4-flow permutation of four different nucleotide species, (b) is not specifically tailored to a particular combination of a particular template polynucleotide strand to be sequenced and a particular sequencing primer to be used, and (c) comprises a phase-protecting flow ordering.

In such a method, the phase-protecting flow ordering may comprise a de Bruijn sequence of four predetermined nucleotide species having a de Bruijn subsequence length parameter of two or three and without any consecutive repeats of the same nucleotide species. The de Bruijn subsequence length parameter may be two. The de Bruijn subsequence length parameter may be three. The predetermined ordering may comprise a portion that is a de Bruijn sequence and a portion that is not a de Bruijn sequence. The four nucleotide species may be A, C, G, and T, and the predetermined ordering may consist of only the phase-protecting flow ordering. The de Bruijn subsequence ordering may be "TACG TCTG AGCA" (SEQ ID NO: 15). The phase-protecting flow ordering may comprise a flow ordering that includes all possible distinct dimer pairs of four nucleotide species. The phase-protecting flow ordering may comprise a flow of N followed immediately by a flow of X, where X and N represent different nucleotide species, and further comprise, immediately thereafter or elsewhere in the ordering, a flow of N followed immediately by a flow of Y, where Y represents a nucleotide species different from both X and N. The phase-protecting flow ordering may comprise a flow of X followed immediately by a flow of N, where X and N represent different nucleotide species, and further comprise a flow of Y followed immediately by a flow of N, where Y represents a nucleotide species different from both X and N. The phase-protecting flow ordering may comprise a first flow ordering in which a first nucleotide species, a second nucleotide species, and a third nucleotide species are flowed at least twice before a fourth nucleotide species is flowed. The phase-protecting flow ordering may further comprise a second flow ordering in which the second nucleotide species, the third nucleotide species, and the fourth nucleotide species are flowed at least twice before the first nucleotide species is flowed. The phase-protecting flow ordering may further comprise a third flow ordering in which the first nucleotide species, the third nucleotide species, and the fourth nucleotide species are flowed at least twice before the second nucleotide species is flowed. The phase-protecting flow ordering may further comprise a fourth flow ordering in which the first nucleotide species, the second nucleotide species, and the fourth nucleotide species are flowed at least twice before the third nucleotide species is flowed. The phase-protecting flow ordering may comprise a first set of flows and a second set of flows, the second set of flows being derived from a remapping of two or more of four nucleotide species flowed in the first set of flows. The second set of flows may be derived from a remapping of all four of the nucleotide species in the first set of flows. The phase-protecting flow ordering may comprise a flow ordering in which at least one given nucleotide species is contiguously flowed two or more times. The predetermined ordering may be selected based on an assessment of dephasing merit and efficiency of extension calculated for a plurality of candidate flow orderings using simulation sequencing data obtained for a plurality of random test sequences. The sensor array may be configured to detect hydrogen ions released by incorporation of nucleotides. The sensor array may be configured to detect inorganic pyrophosphate released by incorporation of nucleotides.

According to an embodiment, there is provided a system for nucleic acid sequencing, comprising: a machine-readable memory; and a processor configured to execute machine-readable instructions, which, when executed by the processor, cause the system to perform steps including: exposing a plurality of template polynucleotide strands in a plurality of defined spaces disposed on a sensor array, at least some of the template polynucleotide strands having a sequencing primer and a polymerase operably bound therewith, to a series of flows of nucleotide species flowed according to a predetermined ordering; and determining, for each of the series of flows of nucleotide species, how many nucleotide incorporations occurred for that particular flow to determine a predicted sequence of nucleotides corresponding to the template polynucleotide strands, wherein the predetermined ordering (a) is not a series of consecutive repetitions of a 4-flow permutation of four different nucleotide species, (b) is not specifically tailored to a particular combination of a particular template polynucleotide strand to be sequenced and a particular sequencing primer to be used, and (c) comprises a phase-protecting flow ordering.

In such a system, the phase-protecting flow ordering may comprise a de Bruijn sequence of four predetermined nucleotide species having a de Bruijn subsequence length parameter of two or three and without any consecutive repeats of the same nucleotide species. The phase-protecting flow ordering may comprise a flow ordering that includes all possible distinct dimer pairs of four nucleotide species. The phase-protecting flow ordering may comprise a flow of N followed immediately by a flow of X, where X and N represent different nucleotide species, and further comprise, immediately thereafter or elsewhere in the ordering, a flow of N followed immediately by a flow of Y, where Y represents a nucleotide species different from both X and N. The phase-protecting flow ordering may comprise a flow of X followed immediately by a flow of N, where X and N represent different nucleotide species, and further comprise a flow of Y followed immediately by a flow of N, where Y represents a nucleotide species different from both X and N. The phase-protecting flow ordering may comprise a first flow ordering in which a first nucleotide species, a second nucleotide species, and a third nucleotide species are flowed at least twice before a fourth nucleotide species is flowed. The phase-protecting flow ordering may further comprise a second flow ordering in which the second nucleotide species, the third nucleotide species, and the fourth nucleotide species are flowed at least twice before the first nucleotide species is flowed. The phase-protecting flow ordering may further comprise a third flow ordering in which the first nucleotide species, the third nucleotide species, and the fourth nucleotide species are flowed at least twice before the second nucleotide species is flowed. The phase-protecting flow ordering may further comprise a fourth flow ordering in which the first nucleotide species, the second nucleotide species, and the fourth nucleotide species are flowed at least twice before the third nucleotide species is flowed. The phase-protecting flow ordering may comprise a first set of flows and a second set of flows, the second set of flows being derived from a remapping of two or more of four nucleotide species flowed in the first set of flows. The phase-protecting flow ordering may comprise a flow ordering in which at least one given nucleotide species is contiguously flowed two or more times. The predetermined ordering may be selected based on an assessment of dephasing merit and efficiency of extension calculated for a plurality of candidate flow orderings using simulation sequencing data obtained for a plurality of random test sequences. The sensor array may be configured to detect hydrogen ions released by incorporation of nucleotides. The sensor array may be configured to detect inorganic pyrophosphate released by incorporation of nucleotides.

According to an embodiment, there is provided a non-transitory machine-readable storage medium comprising instructions which, when executed by a processor, cause the processor to perform a method for nucleic acid sequencing comprising: exposing a plurality of template polynucleotide strands in a plurality of defined spaces disposed on a sensor array, at least some of the template polynucleotide strands having a sequencing primer and a polymerase operably bound therewith, to a series of flows of nucleotide species flowed according to a predetermined ordering; and determining, for each of the series of flows of nucleotide species, how many nucleotide incorporations occurred for that particular flow to determine a predicted sequence of nucleotides corresponding to the template polynucleotide strands, wherein the predetermined ordering (a) is not a series of consecutive repetitions of a 4-flow permutation of four different nucleotide species, (b) is not specifically tailored to a particular combination of a particular template polynucleotide strand to be sequenced and a particular sequencing primer to be used, and (c) comprises a phase-protecting flow ordering.

According to an embodiment, there is provided a method for performing template-based extension of primers, comprising: (a) providing at least one template having a primer and polymerase operably associated thereto; and (b) successively exposing the templates to nucleotides in a plurality of flows such that nucleotides are not flowed in a strictly sequential and successive four nucleotide ordering (e.g., "TACG TACG . . . " or "GATC GATC . . . " or "ACTC ACTC . . . " etc.).

According to an embodiment, there is provided an apparatus for sequencing a polynucleotide strand, comprising: a flow chamber configured to receive flows of different nucleotide species; a plurality of reservoirs that each contain a different nucleotide species; a plurality of flow paths from each of the reservoirs to the flow chamber; and a fluidics controller configured to control the flow from the reservoirs to the flow chamber so as to flow nucleotide species from the reservoirs to the flow chamber according to a predetermined ordering of nucleotide species comprising a phase-protecting flow ordering. In various embodiments, the apparatus may comprise a flow cell loaded into the flow chamber, and the flow cell may comprise a microwell array containing multiple copies of the polynucleotide strand with a primer annealed thereto. The flow cell may comprise a chemFET sensor array for detecting the reaction of the nucleotides with the contents of the microwell array. The polynucleotide strand may be attached to a bead contained in a microwell.

According to an embodiment, there is provided a method for sequencing a polynucleotide strand, comprising: (a) disposing a plurality of template nucleic acids into a plurality of reaction chambers disposed on a sensor array, the sensor array comprising a plurality of sensors and each reaction chamber being disposed on and in a sensing relationship with at least one sensor configured to provide at least one output signal representing a sequencing reaction by-product proximate thereto, and wherein each of the template nucleic acids is hybridized to a sequencing primer and is bound to a polymerase; (b) introducing a known dNTP into the reaction chambers where such known dNTP is selected from a predetermined ordering of dNTP flows; (c) detecting incorporation at a 3' end of the sequencing primer of one or more dNTPs by a sequencing reaction by-product if such one or more dNTPs are complementary to corresponding nucleotides in the template nucleic acid; (d) washing unincorporated dNTPs from the reaction chambers; and (e) repeating steps (b) through (d) until the plurality of template nucleic acids have been sequenced.

According to an embodiment, there is provided a method of performing template-based extension of a primer, comprising: (a) providing at least one template having a primer and polymerase operably associated thereto; and (b) successively exposing the at least one template to nucleotides flowed according to a flow ordering that is not a sequential and successive four nucleotide ordering. The flow ordering may comprise "TACG TACG TAGC TGAC GTAC GTCA TGCA TCGA TCAG CTAG CTGA CGTA GCTA GCAT CGAT CAGT CATG ACTG ACGT AGCT GACT GATC AGTC ATGC ATCG" (SEQ ID NO: 5), "TACT CAGT ATGC AGAC TGCG" (SEQ ID NO: 11), "TACG TACG TACT CAGC TAGC TAGT ATGC ATGC ATGC AGAC TGAC TGAC TGCG" (SEQ ID NO: 12), "TACG TACG TACT CAGC TAGT ATGC ATGC AGAC TGAC TGCG" (SEQ ID NO: 13), "TACG TACG TCTG AGCA TCGA TCGA TGTA CAGC" (SEQ ID NO: 7), "TACG TACG TACG TACG TACA TACG CACG TGCG TATG" (SEQ ID NO: 6), or "TACG TACG TACG TACG TACG TACAT ACGCA CGTGC GTATG" (SEQ ID NO: 2), for example.

According to an embodiment, there is provided a method of determining a sequence of a nucleic acid by template-based extension of a primer, comprising: (a) delivering a known nucleoside triphosphate precursor to a template-based primer extension reaction, the known nucleoside triphosphate precursor being selected from a predetermined ordering of dNTP flows; (b) detecting incorporation of the known nucleoside triphosphate whenever its complement is present in the template adjacent to the primer; and (c) repeating steps (a) and (b) until the sequence of the nucleic acid has been determined, wherein the predetermined ordering of dNTP flows is adapted to improve phase synchronicity. The predetermined ordering of dNTP flows may be further adapted to reduce and/or at least partially corrects phasing effects associated with incomplete extension events. The predetermined ordering of dNTP flows may be further adapted to reduce and/or at least partially corrects phasing effects associated with carry forward events. The predetermined ordering of dNTP flows may be further adapted to reduce and/or at least partially corrects phasing effects associated with polymerase efficiency.

According to an embodiment, there is provided a method for sequencing a nucleic acid, comprising: (a) disposing a plurality of templates into a plurality of reaction chambers, each reaction chamber comprising a template having a sequencing primer hybridized thereto and a polymerase operably bound thereto; (b) introducing a known nucleoside triphosphate into each reaction chamber selected from a predetermined ordering of dNTP flows; (c) detecting sequential incorporation at the 3' end of the sequencing primer of one or more nucleoside triphosphates if the known nucleoside triphosphate is complementary to corresponding nucleotides in the template nucleic acid; (d) washing unincorporated nucleoside triphosphates from the reaction chamber; and (e) repeating steps (b) through (d) until the nucleic acid has been sequenced, wherein the predetermined ordering of dNTP flows is defined by a plurality of flows such that nucleotides are not flowed in a series of consecutive repeats of a predetermined four nucleotide ordering. The predetermined ordering may comprise "TACT CAGT ATGC AGAC TGCG" (SEQ ID NO: 11), "TACG TACG TACT CAGC TAGC TAGT ATGC ATGC ATGC AGAC TGAC TGAC TGCG" (SEQ ID NO: 12), "TACG TACG TACT CAGC TAGT ATGC ATGC AGAC TGAC TGCG" (SEQ ID NO:

13), "TACG TACG TCTG AGCA TCGA TCGA TGTA CAGC" (SEQ ID NO: 7), "TACG TACG TACG TACG TACG TACA TACG CACG TGCG TATG" (SEQ ID NO: 6), or "TACG TACG TACG TACG TACG TACAT ACGCA CGTGC GTATG" (SEQ ID NO: 2), for example.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of the four nucleotide species A, C, G, and T according to a predetermined ordering, wherein the predetermined ordering comprises a de Bruijn sequence ordering of the four nucleotide species A, C, G, and T with a de Bruijn subsequence length parameter of two or three and without any consecutive repeats of the same nucleotide species. The de Bruijn subsequence length parameter may be two. The de Bruijn subsequence length parameter may be three. The predetermined ordering may consist of only the de Bruijn sequence ordering, or it may include a portion that is a de Bruijn sequence ordering and a portion that is not a de Bruijn sequence ordering. The method may further comprise detecting hydrogen ions released by incorporation of the nucleotides. The method may further comprise detecting inorganic pyrophosphate released by incorporation of the nucleotides. The inorganic pyrophosphate may be detected by light emitted from an enzyme cascade initiated by the inorganic pyrophosphate.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of the four nucleotide species A, C, G, and T according to a predetermined ordering, wherein the predetermined ordering comprises a flow ordering that includes all possible distinct dimer pairs of the four nucleotide species. The possible distinct dimer pairs include AG, AC, AT, CA, CG, CT, GA, GC, GT, TA, TC, and TG.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of the four nucleotide species A, C, G, and T according to a predetermined ordering, wherein the predetermined ordering comprises a flow of N followed immediately by a flow of X, where X and N represent different nucleotide species, and further comprises, immediately thereafter or elsewhere in the ordering, a flow of N followed immediately by a flow of Y, where Y represents a nucleotide species different from both X and N. In an embodiment, the flows of N and Y may immediately follow the flows of N and X. In another embodiment, the flows of N and Y may not immediately follow the flows of N and X.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of the four nucleotide species A, C, G, and T according to a predetermined ordering, wherein the predetermined ordering comprises a flow of X followed immediately by a flow of N, where X and N represent different nucleotide species, and further comprises a flow of Y followed immediately by a flow of N, where Y represents a nucleotide species different from both X and N. In an embodiment, the flows of Y and N may immediately follow the flows of X and N. In another embodiment, the flows of Y and N may not immediately follow the flows of X and N.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of four different nucleotide species according to a predetermined ordering, wherein the predetermined ordering comprises a flow ordering in which a first nucleotide species, a second nucleotide species, and a third nucleotide species are flowed at least twice before a fourth nucleotide species is flowed. In an embodiment, the flow ordering may be a first flow ordering and the predetermined ordering may further comprise a second flow ordering in which the second nucleotide species, the third nucleotide species, and the fourth nucleotide species are flowed at least twice before the first nucleotide species is flowed. In an embodiment, the predetermined ordering may further comprise a third flow ordering in which the first nucleotide species, the third nucleotide species, and the fourth nucleotide species are flowed at least twice before the second nucleotide species is flowed. In an embodiment, the predetermined ordering may further comprise a fourth flow ordering in which the first nucleotide species, the second nucleotide species, and the fourth nucleotide species are flowed at least twice before the third nucleotide species is flowed.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of the four nucleotide species A, C, G, and T according to a predetermined ordering, wherein the predetermined ordering comprises a first set of flows and a second set of flows, the second set of flows being derived from a remapping of two or more of the nucleotide species in the first set of flows. In an embodiment, the second set of flows may be derived from a remapping of all four of the nucleotide species in the first set of flows. The remapping may involve a reassignment of each instance of the two or more nucleotide species in the first set of flows.

According to an embodiment, there is provided a method of sequencing a polynucleotide strand, comprising: providing the polynucleotide strand with a primer annealed thereto and a polymerase operably bound to the polynucleotide strand; and successively exposing the polynucleotide strand to the flow of the four nucleotide species A, C, G, and T according to a predetermined ordering, wherein the predetermined ordering comprises a flow ordering in which the same nucleotide species is contiguously flowed two or more times.

According to various embodiments, one or more features of any one or more of the above-discussed teachings and/or embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of any one or more of the above-discussed teachings and/or embodiments may be performed or implemented using appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or rewriteable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various embodiments, one or more features of any one or more of the above-discussed teachings and/or embodiments may be performed or implemented at least partly using a distributed, clustered, remote, or cloud computing resource.

According to various embodiments, one or more features of any one or more of the above-discussed teachings and/or embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various embodiments, one or more of the above-discussed embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional embodiments may be derived by repeating, adding, or substituting any generically or specifically described features and/or components and/or substances and/or steps and/or operating conditions set forth in one or more of the above-described embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed embodiments may be considered to be a potential optional feature, component, aspect, step, or other characteristic of any other of the above-discussed embodiments so long as the objective of such any other of the above-discussed embodiments remains achievable, unless specifically stated otherwise.

Although various embodiments of the present teachings may advantageously be used with sequencing-by-synthesis approaches, as described herein and in Rothberg et al., U.S. Pat. Publ. No. 2009/0026082; Anderson et al., SENSORS AND ACTUATORS B CHEM., 129:79-86 (2008); Pourmand et al., PROC. NATL. ACAD. SCI., 103:6466-6470 (2006), which are all incorporated by reference herein in their entirety, for example, the present teachings may also be used with other approaches, such as variants of sequencing-by-synthesis including methods where the nucleotides or nucleoside triphosphate precursors are modified to be reversible terminators (sometimes referred to as cyclic reversible termination (CRT) methods) and methods where the nucleotides or nucleoside triphosphate precursors are unmodified (sometimes referred to as cyclic single base delivery (CSD) methods), for example, or more generally methods that comprise repeated steps of delivering (or extending in response to delivering) nucleotides (to the polymerase-primer-template complex) and collecting signals (or detecting the incorporation either directly or indirectly).

Although various embodiments of the present teachings may advantageously be used in connection with pH-based sequence detection, as described herein and in Rothberg et al., U.S. Pat. Appl. Publ. Nos. 2009/0127589 and 2009/0026082 and Rothberg et al., U.K. Pat. Appl. Publ. No. GB2461127, which are all incorporated by reference herein in their entirety, for example, the present teachings may also be used with other detection approaches, including the detection of pyrophosphate (PPi) released by the incorporation reaction (see, e.g., U.S. Pat. Nos. 6,210,891; 6,258,568; and 6,828,100); various fluorescence-based sequencing instrumentation (see, e.g., U.S. Pat. Nos. 7,211,390; 7,244,559; and 7,264,929); some sequencing-by-synthesis techniques that can detect labels associated with the nucleotides, such as mass tags, fluorescent, and/or chemiluminescent labels (in which case an inactivation step may be included in the workflow (e.g., by chemical cleavage or photobleaching) prior to the next cycle of synthesis and detection); and more generally methods where an incorporation reaction generates or results in a product or constituent with a property capable of being monitored and used to detect the incorporation event, including, for example, changes in magnitude (e.g., heat) or concentration (e.g., pyrophosphate and/or hydrogen ions), and signal (e.g., fluorescence, chemiluminescence, light generation), in which cases the amount of the detected product or constituent may be monotonically related to the number of incorporation events, for example. Such other approaches may likewise benefit from the phase correction, signal enhancement, improved accuracy, and/or noise reduction features of the nucleotide flows approaches described herein.

Although the present description described in detail certain embodiments, other embodiments are also possible and within the scope of the present invention. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

The invention claimed is:

1. A method for nucleic acid sequencing, comprising:
disposing a plurality of template polynucleotide strands in a plurality of defined spaces disposed on a sensor array, at least some of the template polynucleotide strands having a sequencing primer and a polymerase operably bound therewith;
exposing the template polynucleotide strands with the sequencing primer and the polymerase operably bound therewith to a series of flows of nucleotide species flowed according to a predetermined ordering; and
determining, for each of the series of flows of nucleotide species, how many nucleotide incorporations occurred for that particular flow to determine a sequence of nucleotides corresponding to the template polynucleotide strands,
wherein the predetermined ordering:
(a) is not a series of consecutive repetitions of a 4-flow permutation of four different nucleotide species,
(b) is not specifically tailored to a particular combination of a particular template polynucleotide strand to be sequenced and a particular sequencing primer to be used, and
(c) comprises a phase-protecting flow ordering that comprises a de Bruijn sequence of nucleotide species A, C, G, and T such that:
(i) every possible subsequence of two of the nucleotide species A, C, G, and T appears once as a sequence of consecutive nucleotide species in the de Bruijn sequence or
(ii) every possible subsequence of three of the nucleotide species A, C, G, and T appears once as a sequence of consecutive nucleotide species in the de Bruijn sequence.

2. The method of claim 1, wherein the de Bruijn sequence does not include any consecutive repeats of the same nucleotide species.

3. The method of claim 1, wherein the de Bruijn sequence is such that every possible subsequence of two of the nucleotide species A, C, G, and T appears once as a sequence of consecutive nucleotide species in the de Bruijn sequence.

4. The method of claim 1, wherein the de Bruijn sequence is such that every possible subsequence of three of the nucleotide species A, C, G, and T appears once as a sequence of consecutive nucleotide species in the de Bruijn sequence.

5. The method of claim 1, wherein the predetermined ordering comprises a portion that is a de Bruijn sequence and a portion that is not a de Bruijn sequence.

6. The method of claim 1, wherein the predetermined ordering consists of only the phase-protecting flow ordering.

7. The method of claim 1, wherein the phase-protecting flow ordering comprising the de Bruijn sequence comprises a flow of T, followed by a flow of A, followed by a flow of C, followed by a flow of G, followed by a flow of T, followed by a flow of C, followed by a flow of T, followed by a flow of G, followed by a flow of A, followed by a flow of G, followed by a flow of C, followed by a flow of A.

8. The method of claim 1, wherein the phase-protecting flow ordering comprises a first set of flows and a second set of flows, the second set of flows being derived from a remapping of two or more of four nucleotide species flowed in the first set of flows.

9. The method of claim 8, wherein the second set of flows is derived from a remapping of all four of the nucleotide species in the first set of flows.

10. The method of claim 1, wherein the phase-protecting flow ordering comprises a flow ordering in which at least one given nucleotide species is contiguously flowed two or more times.

11. The method of claim 1, wherein the predetermined ordering is selected based on an assessment of dephasing merit and efficiency of extension calculated for a plurality of candidate flow orderings using simulation sequencing data obtained for a plurality of random test sequences.

12. The method of claim 1, wherein the sensor array is configured to detect hydrogen ions released by incorporation of nucleotides.

13. The method of claim 1, wherein the sensor array is configured to detect inorganic pyrophosphate released by incorporation of nucleotides.

* * * * *

SEQUENCE LISTING

```
<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Exemplary Strand

<400> SEQUENCE: 1
tagcactacg gaacgtgaag gt                                          22

<210> SEQ ID NO 2
<211> LENGTH: 40
<212> TYPE: DNA
<213> ORGANISM: Artificial Sequence
<220> FEATURE:
<223> OTHER INFORMATION: Ordering of Nucleotide Species Flows

<400> SEQUENCE: 2
tacgtacgta cgtacgtacg tacatacgca cgtgcgtatg                       40

<210> SEQ ID NO 3
<211> LENGTH: 16
<212> TYPE: DNA
<213> ORGANISM: Artificial Sequence
<220> FEATURE:
<223> OTHER INFORMATION: Ordering of Nucleotide Species Flows

<400> SEQUENCE: 3
```

```
tacgtacgtc tgagca                                                         16

<210> SEQ ID NO 4
<211> LENGTH: 104
<212> TYPE: DNA
<213> ORGANISM: Artificial Sequence
<220> FEATURE:
<223> OTHER INFORMATION: Ordering of Nucleotide Species Flows

<400> SEQUENCE: 4
tacgtacgta gcttgacgta cgtcatgcat cgatcagcta agctgacgta gctagcatcg         60
atccagtcat gactgacgta gctgactgga tcagtcatgc atcg                         104

<210> SEQ ID NO 5
<211> LENGTH: 100
<212> TYPE: DNA
<213> ORGANISM: Artificial Sequence
<220> FEATURE:
<223> OTHER INFORMATION: Ordering of Nucleotide Species Flows

<400> SEQUENCE: 5
tacgtacgta gctgacgtac gtcatgcatc gatcagctag ctgacgtagc tagcatcgat         60
cagtcatgac tgacgtagct gactgatcag tcatgcatcg                             100

<210> SEQ ID NO 6
<211> LENGTH: 40
<212> TYPE: DNA
<213> ORGANISM: Artificial Sequence
<220> FEATURE:
<223> OTHER INFORMATION: Ordering of Nucleotide Species Flows

<400> SEQUENCE: 6
tacgtacgta cgtacgtacg tacatacgca cgtgcgtatg                              40

<210> SEQ ID NO 7
<211> LENGTH: 32
<212> TYPE: DNA
<213> ORGANISM: Artificial Sequence
<220> FEATURE:
<223> OTHER INFORMATION: Ordering of Nucleotide Species Flows

<400> SEQUENCE: 7
tacgtacgtc tgagcatcga tcgatgtaca gc                                      32

<210> SEQ ID NO 8
<211> LENGTH: 192
<212> TYPE: DNA
<213> ORGANISM: Artificial Sequence
<220> FEATURE:
<223> OTHER INFORMATION: Ordering of Nucleotide Species Flows

<400> SEQUENCE: 8
tacgtacgtc tgagcatcga tcgatgtaca gctgactgac tatcgcagag ctagctacat         60
gtcgactgac tgatagcgtc atgcatgcag actcgtcgta cgtactcaga tgctagctag        120
cacgtgatca gtcagtcgct atgagtcagt cagcgatact gcatgcatga gtctacgatc        180
gatcgtgcac ta                                                           192

<210> SEQ ID NO 9
<211> LENGTH: 64
<212> TYPE: DNA
<213> ORGANISM: Artificial Sequence
<220> FEATURE:
```

-continued

<223> OTHER INFORMATION: Ordering of Nucleotide Species Flows

<400> SEQUENCE: 9
cttgcttaca actctcatat cggtatcctg tggaaactcc gttatcagca tcctctcatg    60
ttag    64

<210> SEQ ID NO 10
<211> LENGTH: 36
<212> TYPE: DNA
<213> ORGANISM: Artificial Sequence
<220> FEATURE:
<223> OTHER INFORMATION: Ordering of Nucleotide Species Flows

<400> SEQUENCE: 10
tacactctag tatagagtcg tgtctcgacg cgagac    36

<210> SEQ ID NO 11
<211> LENGTH: 20
<212> TYPE: DNA
<213> ORGANISM: Artificial Sequence
<220> FEATURE:
<223> OTHER INFORMATION: Ordering of Nucleotide Species Flows

<400> SEQUENCE: 11
tactcagtat gcagactgcg    20

<210> SEQ ID NO 12
<211> LENGTH: 52
<212> TYPE: DNA
<213> ORGANISM: Artificial Sequence
<220> FEATURE:
<223> OTHER INFORMATION: Ordering of Nucleotide Species Flows

<400> SEQUENCE: 12
tacgtacgta ctcagctagc tagtatgcat gcatgcagac tgactgactg cg    52

<210> SEQ ID NO 13
<211> LENGTH: 40
<212> TYPE: DNA
<213> ORGANISM: Artificial Sequence
<220> FEATURE:
<223> OTHER INFORMATION: Ordering of Nucleotide Species Flows

<400> SEQUENCE: 13
tacgtacgta ctcagctagt atgcatgcag actgactgcg    40

<210> SEQ ID NO 14
<211> LENGTH: 44
<212> TYPE: DNA
<213> ORGANISM: Artificial Sequence
<220> FEATURE:
<223> OTHER INFORMATION: Ordering of Nucleotide Species Flows

<400> SEQUENCE: 14
tacgtacgtt actcagctaa gtatgcatgg cagactgacc tgcg    44

<210> SEQ ID NO 15
<211> LENGTH: 12
<212> TYPE: DNA
<213> ORGANISM: Artificial Sequence
<220> FEATURE:
<223> OTHER INFORMATION: Ordering of Nucleotide Species Flows

<400> SEQUENCE: 15
tacgtctgag ca    12

<210> SEQ ID NO 16
<211> LENGTH: 40
<212> TYPE: DNA
<213> ORGANISM: Artificial Sequence
<220> FEATURE:
<223> OTHER INFORMATION: Ordering of Nucleotide Species Flows

<400> SEQUENCE: 16
tacgtacgta cgtacgtacg tacgtacgca cgtgcgtatg                          40

<210> SEQ ID NO 17
<211> LENGTH: 40
<212> TYPE: DNA
<213> ORGANISM: Artificial Sequence
<220> FEATURE:
<223> OTHER INFORMATION: Ordering of Nucleotide Species Flows

<400> SEQUENCE: 17
tacgtacgta ctcagctagt atgcatgcag actgactgcg                          40

<210> SEQ ID NO 18
<211> LENGTH: 12
<212> TYPE: DNA
<213> ORGANISM: Artificial Sequence
<220> FEATURE:
<223> OTHER INFORMATION: Ordering of Nucleotide Species Flows

<400> SEQUENCE: 18
tctagactcg ag                                                        12

<210> SEQ ID NO 19
<211> LENGTH: 12
<212> TYPE: DNA
<213> ORGANISM: Artificial Sequence
<220> FEATURE:
<223> OTHER INFORMATION: Ordering of Nucleotide Species Flows

<400> SEQUENCE: 19
tcgatgtaca gc                                                        12

<210> SEQ ID NO 20
<211> LENGTH: 20
<212> TYPE: DNA
<213> ORGANISM: Artificial Sequence
<220> FEATURE:
<223> OTHER INFORMATION: Ordering of Nucleotide Species Flows

<400> SEQUENCE: 20
tacatacgca cgtgcgtatg                                                20

<210> SEQ ID NO 21
<211> LENGTH: 40
<212> TYPE: DNA
<213> ORGANISM: Artificial Sequence
<220> FEATURE:
<223> OTHER INFORMATION: Ordering of Nucleotide Species Flows

<400> SEQUENCE: 21
tacgtacgta cgtacgtacg tacatacgca cgtgcgtatg                          40

<210> SEQ ID NO 22
<211> LENGTH: 13
<212> TYPE: DNA
<213> ORGANISM: Artificial Sequence
<220> FEATURE:

```
<223> OTHER INFORMATION: Exemplary Strand

<400> SEQUENCE: 22
gatctaagca tct                                                          13

<210> SEQ ID NO 23
<211> LENGTH: 16
<212> TYPE: DNA
<213> ORGANISM: Artificial Sequence
<220> FEATURE:
<223> OTHER INFORMATION: Ordering of Nucleotide Species Flows

<400> SEQUENCE: 23
tacgtacgta cgtacg                                                       16
```